(12) United States Patent
Wager et al.

(10) Patent No.: US 8,389,743 B2
(45) Date of Patent: *Mar. 5, 2013

(54) HISTAMINE-3 RECEPTOR ANTAGONISTS

(75) Inventors: Travis T. Wager, New London, CT (US); Ramalakshmi Yegna Chandrasekaran, Gales Ferry, CT (US); Todd William Butler, Salem, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/415,944

(22) Filed: Mar. 9, 2012

(65) Prior Publication Data

US 2012/0220568 A1   Aug. 30, 2012

Related U.S. Application Data

(63) Continuation of application No. 11/549,175, filed on Oct. 13, 2006, now Pat. No. 8,158,673.

(60) Provisional application No. 60/730,996, filed on Oct. 27, 2005.

(51) Int. Cl.
*C07D 207/09* (2006.01)
*A61K 31/40* (2006.01)

(52) U.S. Cl. ......................... 548/578; 514/428
(58) Field of Classification Search .......... 548/578; 514/428
See application file for complete search history.

(56) References Cited

U.S. PATENT DOCUMENTS

| | | | |
|---|---|---|---|
| 6,559,140 B2 | 5/2003 | Bennani et al. | 514/210.02 |
| 7,456,164 B2 | 11/2008 | Bernardelli et al. | 514/210.19 |
| 7,557,121 B2 | 7/2009 | Lunn et al. | 514/300 |
| 7,671,047 B2 | 3/2010 | Jaehne et al. | 514/210.02 |
| 8,158,673 B2 * | 4/2012 | Wager et al. | 514/428 |
| 2008/0176925 A1 | 7/2008 | Butler et al. | 514/428 |

FOREIGN PATENT DOCUMENTS

| WO | WO 02 076925 | 10/2002 |
|---|---|---|
| WO | WO 2005 080361 | 9/2005 |
| WO | WO 2006 136924 | 12/2009 |

OTHER PUBLICATIONS

Medhurst, et al., "GSK189254, a Novel $H_3$ Receptor Antagonist That Binds to Histamine $H_3$ Receptors in Alzheimer's Disease Brain and Improves Cognitive Performance in Preclinical Models", Journal of Pharmacology and Experimental Therapeutics, Jun. 1, 2007, pp. 1032-1045, 321(3).

Ligneau, X., et al., "Distinct pharmacology of rat and human histamine $H_3$ receptors: role of tow amino acids in the third transmembrane domain", British Journal of Pharmacology, Dec. 2000, pp. 1247-1250, 131(7).

PCT/IB2006/002977 WO 2007/049123, filing dated Oct. 16, 2006, International Search Report, dated Mar. 6, 2007, 3 pages.

* cited by examiner

*Primary Examiner* — Joseph Kosack
(74) *Attorney, Agent, or Firm* — John A. Wichtowski

(57) ABSTRACT

This invention is directed to a compound of formula I,

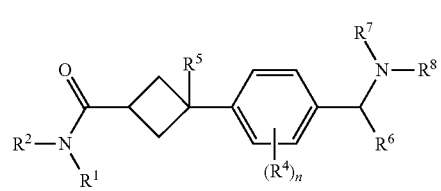

wherein $R^1$, $R^2$, $R^4$, $R^5$, $R^6$, $R^7$, $R^8$ and n are as defined herein, or a pharmaceutically acceptable salt thereof; a pharmaceutical composition containing a compound of formula I, a process of preparation of a compound of formula I, a method of treatment of a disorder or condition such as depression, mood disorders, schizophrenia, anxiety disorders, Alzheimer's disease, attention-deficit hyperactivity disorder (ADHD), psychotic disorders, cognitive disorders, sleep disorders, obesity, dizziness, epilepsy, motion sickness, respiratory diseases, allergy, allergy-induced airway responses, allergic rhinitis, nasal congestion, allergic congestion, congestion, hypotension, cardiovascular disease, diseases of the GI tract, hyper and hypo motility and acidic secretion of the gastro-intestinal tract that may be treated by antagonizing histamine H3 receptors, the method comprising administering to a mammal in need of such treatment a compound of formula I as described above.

24 Claims, No Drawings

HISTAMINE-3 RECEPTOR ANTAGONISTS

This application is a Continuation of application Ser. No. 11/549,175 filed Oct. 13, 2006, which claims the benefit of Provisional Patent Application No. 60/730,996 filed Oct. 27, 2005.

BACKGROUND OF THE INVENTION

This invention is directed to compounds of formula I described herein, to a pharmaceutical composition comprising such compounds, to a process of preparation of such compounds, and to methods of treatment of disorders or conditions that may be treated by antagonizing histamine-3 (H3) receptors using such compounds.

Histamine is a well-known mediator in hypersensitive reactions (e.g. allergies, hay fever, and asthma) that are commonly treated with antagonists of histamine or "antihistamines." It has also been established that histamine receptors exist in at least two distinct types, referred to as H1 and H2 receptors.

A third histamine receptor (H3 receptor) is believed to play a role in neurotransmission in the central nervous system, where the H3 receptor is thought to be disposed presynaptically on histaminergic nerve endings (Nature, 302, S32-837 (1983)). The existence of the H3 receptor has been confirmed by the development of selective H3 receptor agonists and antagonists (Nature, 327, 117-123 (1987)) and has subsequently been shown to regulate the release of the neurotransmitters in both the central nervous system and peripheral organs, particularly the lungs, cardiovascular system and gastrointestinal tract.

A number of diseases or conditions may be treated with histamine-3 receptor ligands wherein the H3 ligand may be an antagonist, agonist or partial agonist, see: (Imamura et al., Circ. Res., (1996) 78, 475-481); (Imamura et. al., Circ. Res., (1996) 78, 863-869); (Lin et al., Brain Res. (1990) 523, 325-330); (Monti et al., Neuropsychopharmacology (1996) 15, 31 35); (Sakai, et al., Life Sci. (1991) 48, 2397-2404); (Mazurkiewiez-Kwilecki and Nsonwah, Can. J. Physiol. Pharmacol. (1989) 67, 75-78); (Panula, P. et al., Neuroscience (1998) 44, 465-481); (Wada et al., Trends in Neuroscience (1991) 14,415); (Monti et al., Eur. J. Pharmacol. (1991) 205, 283); (Mazurkiewicz-Kwilecki and Nsonwah, Can. J. Physiol. Pharmacol. (1989) 67, 75-78); (Haas et al., Behav. Brain Res. (1995) 66, 41-44); (De Almeida and Izquierdo, Arch. Int. Pharmacodyn. (1986) 283, 193-198); (Kamei et al., Psychopharmacology (1990) 102, 312-318); (Kamei and Sakata, Japan. J. Pharmacol. (1991) 57, 437-482); (Schwartz et al., Psychopharmacology; The fourth Generation of Progress, Bloom and Kupfer (eds.), Raven Press, New York, (1995) 3 97); (Shaywitz et al., Psychopharmacology (1984) 82, 73-77); (Dumery and Blozovski, Exp. Brain Res. (1987) 67, 61-69); (Tedford et al., J. Pharmacol. Exp. Ther. (1995) 275, 598-604); (Tedford et al., Soc. Neurosci. Abstr. (1996) 22, 22); (Yokoyama et al., Eur. J. Pharmacol. (1993) 234,129); (Yokoyama and Iinuma, CNS Drugs (1996) 5, 321); (Onodera et al., Prog. Neurobiol. (1994) 42, 685); (Leurs and Timmerman, Prog. Drug Res. (1992) 39,127); (The Histamine H3 Receptor, Leurs and Timmerman (ed.), Elsevier Science, Amsterdam, The Netherlands (1998); (Leurs et al., Trends in Pharm. Sci. (1998) 19, 177-183); (Phillips et al., Annual Reports in Medicinal Chemistry (1998) 33, 31-40); (Matsubara et al., Eur. J. Pharmacol. (1992) 224, 145); (Rouleau et al., J. Pharmacol. Exp. Ther. (1997) 281, 1085); (Adam Szelag "Role of histamine H3-receptors in the proliferation of neoplastic cells in vitro", Med. Sci. Monit., 4(5): 747-755, (1998)); (Fitzsimons, C., H. Duran, F. Labombarda, B. Molinari and E. Rivera, "Histamine receptors signalling in epidermal tumor cell lines with H-ras gene alterations", Inflammation Res., 47 (Suppl. 1): S50-S51, (1998)); (R. Leurs, R. C. Volling a and H. Timmerman, The medicinal chemistry and therapeutic potentials of ligand of the histamine H3 receptor, Progress in Drug Research 45: 170-165, (1995)); (R. Levi and N. C. E. Smith, "Histamine H3-receptors: A new frontier in myocardial ischemia", J. Pharm. Exp. Ther., 292: 825-830, (2000)); (Hatta, E., K Yasuda and R. Levi, "Activation of histamine H3 receptors inhibits carrier-mediated norepinephrine release in a human model of protracted myocardial ischemia", J. Pharm. Exp. Ther., 283: 494-500, (1997); (H. Yokoyama and K. Iinuma, "Histamine and Seizures: Implications for the treatment of epilepsy", CNS Drugs, 5(5); 321-330, (1995)); (K. Hurukami, H. Yokoyama, K. Onodera, K. Iinuma and T. Watanabe, AQ-0 145, "A newly developed histamine H3 antagonist, decreased seizure susceptibility of electrically induced convulsions in mice", Meth. Find. Exp. Clin. Pharmacol., 17(C): 70-73, (1995); (Delaunois A., Gustin P., Garbarg M., and Ansay M., "Modulation of acetylcholine, capsaicin and substance P effects by histamine H3 receptors in isolated perfused rabbit lungs", European Journal of Pharmacology 277(2-3):243-50, (1995)); and (Dimitriadou, et al., "Functional relationship between mast cells and C—sensitive nerve fibres evidenced by histamine H3-receptor modulation in rat lung and spleen", Clinical Science 87(2): 151-63, (1994). Such diseases or conditions include cardiovascular disorders such as acute myocardial infarction; memory processes, dementia and cognitive disorders such as Alzheimer's disease and attention-deficit hyperactivity disorder; neurological disorders such as Parkinson's disease, schizophrenia, depression, epilepsy, and seizures or convulsions; cancer such as cutaneous carcinoma, medullary thyroid carcinoma and melanoma; respiratory disorders such as asthma; sleep disorders such as narcolepsy; vestibular dysfunction such as Meniere's disease; gastrointestinal disorders, inflammation, migraine, motion sickness, obesity, pain, and septic shock.

H3 receptor antagonists have also been previously described in, for example, WO 03/050099, WO 02/0769252, WO 02/12224, and U.S. Patent Publication No. 2005/0171181 A1. The histamine H3 receptor (H3R) regulates the release of histamine and other neurotransmitters, including serotonin and acetylcholine. H3R is relatively neuron specific and inhibits the release of certain monoamines such as histamine. Selective antagonism of H3R receptors raises brain histamine levels and inhibits such activities as food consumption while minimizing non-specific peripheral consequences. Antagonists of the receptor increase synthesis and release of cerebral histamine and other monoamines. By this mechanism, they induce a prolonged wakefulness, improved cognitive function, reduction in food intake and normalization of vestibular reflexes. Accordingly, the receptor is an important target for new therapeutics in Alzheimer disease, mood disorders and cognitive disorders, including attention deficit hyperactive disorder (ADHD), attention deficiet disorder (ADD), cognitive deficiencies, obesity, dizziness, schizophrenia, epilepsy, sleeping disorders, narcolepsy and motion sickness, and various forms of anxiety.

The majority of histamine H3 receptor antagonists to date resemble histamine in possessing an imidazole ring that may be substituted, as described, for example, in WO 96/38142. Non-imidazole neuroactive compounds such as beta histamines (Arrang, Eur. J. Pharm. 1985, 111:72-84) demonstrated some histamine H3 receptor activity but with poor potency. EP 978512 and EP 0982300A2 disclose non-imidazole alkyamines as histamine H3 receptor antagonists. WO 02/12224 (Ortho McNeil Pharmaceuticals) describes non-imidazole bicyclic derivatives as histamine H3 receptor ligands. Other receptor antagonists have been described in WO 02/32893 and WO 02/06233.

The compounds of this invention are highly selective for the H3 receptor (vs. other histamine receptors), and possess remarkable drug disposition properties (pharmacokinetics). In particular, the compounds of this invention selectively distinguish H3R from the other receptor subtypes H1R, H2R. In view of the increased level of interest in histamine H3 receptor agonists, inverse agonists and antagonists in the art, novel compounds that interact with the histamine H3 receptor would be a highly desirable contribution to the art. The present invention provides such a contribution to the art being based on the finding that a novel class of cyclobutyl reverse amides has a high and specific affinity to the histamine H3 receptor and have a superior drug profile.

SUMMARY OF THE INVENTION

This invention is directed to a compound of formula I:

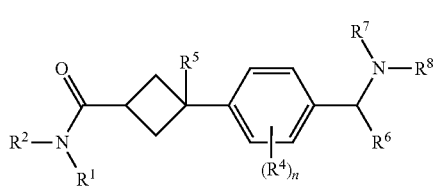

I or a pharmaceutically acceptable salt thereof, wherein:
$R^1$ and $R^2$ are each independently selected from the group consisting of hydrogen;
$C_1$-$C_8$ alkyl optionally substituted with 1 to 4 halogens;
$C_1$-$C_4$ alkyl group optionally substituted with a substituent selected from the group consisting of OH, one to four $C_1$-$C_4$ alkyl, $C_3$-$C_7$ cycloalkyl, $C_1$-$C_4$ dialkylamino, $C_6$-$C_{14}$ aryl optionally substituted with a halogen and optionally substituted with $C_6$-$C_{10}$ aryloxy optionally substituted with one to two halogens, and 5-10-membered heteroaryl optionally substituted with a $C_6$-$C_{10}$ aryl group and optionally substituted with one to three $C_1$-$C_4$ alkyl groups;
$C_3$-$C_7$ cycloalkyl;
$C_6$-$C_{14}$ aryl;
—($C_0$-$C_3$)alkyl-O—($C_1$-$C_3$)alkyl optionally substituted with ($C_1$-$C_3$)alkyl;
—($C_1$-$C_3$)alkyl-C(=O)O—($C_1$-$C_3$)alkyl;
3-8-membered heterocycloalkyl optionally substituted with one or more $C_1$-$C_4$ alkyl-carbonyl groups;
$C_6$-$C_{10}$ arylsulfonyl optionally substituted with one or more $C_1$-$C_2$ alkyl;
5-10-membered heteroaryl; and
$C_6$-$C_{14}$ aryl-$C_0$-$C_4$ alkylene-O—$C_0$-$C_4$ alkyl, wherein each $C_0$-$C_4$ alkyl and each $C_0$-$C_4$ alkylene is optionally substituted with one to four $C_1$-$C_4$ alkyl;
or optionally $R^1$ and $R^2$, together with the nitrogen to which they are attached, form a 4-, 5-, 6-, or 7-membered saturated or unsaturated aliphatic ring, wherein one of the carbons in said aliphatic ring is optionally replaced by O, S, $NR^3$, or CO, and wherein said ring is optionally fused to a $C_6$-$C_{10}$ arylene and is optionally substituted at a ring carbon with a substituent selected from the group consisting of
—OH, 5-10-membered heteroaryl optionally substituted with one or more halogens and optionally substituted with one or more $C_1$-$C_2$ alkyl,
$C_1$-$C_4$ alkoxy optionally substituted with one or more $C_1$-$C_2$ alkoxy and optionally substituted with one or more $C_1$-$C_4$ dialkylaminocarbonyl, and
one or two $C_1$-$C_4$ alkyl optionally and independently substituted with one or more $C_1$-$C_2$ alkoxy;
wherein $R^3$ is
hydrogen;
$C_1$-$C_8$ alkyl optionally substituted with 1 to 4 halogens;
5-10-membered heteroaryl optionally substituted with a substituent selected from the group consisting of halogen, $C_1$-$C_4$ alkyl, $C_1$-$C_2$ alkoxy, $C_6$-$C_{10}$ aryl, $C_1$-$C_4$ alkylaminocarbonyl, and cyano;
$C_1$-$C_4$ alkyl group optionally substituted with a substituent selected from the group consisting of $C_1$-$C_2$ alkoxycarbonyl, 5-10-membered heteroaryl optionally substituted with one or more $C_1$-$C_2$ alkyl, one to four $C_1$-$C_4$ alkyl, $C_3$-$C_7$ cycloalkyl, and $C_6$-$C_{14}$ aryl;
$C_6$-$C_{10}$ aryl optionally substituted with one or two $C_1$-$C_2$ alkyl;
$C_1$-$C_4$ alkylcarbonyl;
or $C_6$-$C_{14}$ aryl-$C_0$-$C_4$ alkylene-O—$C_0$-$C_4$ alkyl, wherein each $C_0$-$C_4$ alkyl and each $C_0$-$C_4$ alkylene is optionally substituted with one to four $C_1$-$C_4$ alkyl;
$R^4$ is independently selected from the group consisting of hydrogen, $C_1$-$C_4$ alkyl, $C_1$-$C_4$ alkoxyl, halogen, nitrile, —$SO_2C_1$-$C_4$, —$SO_2NHC_1$-$C_4$, and —C(=O)$NHC_1$-$C_4$;
n is 0, 1, 2, 3, or 4;
$R^5$ is OH, —O($C_1$-$C_3$)alkyl, halogen or hydrogen;
$R^6$ is hydrogen, $C_1$-$C_4$ alkyl optionally substituted with 1 to 4 halogens, or $C_3$-$C_7$ cycloalkyl-$C_0$-$C_4$ alkyl;
$R^7$ is hydrogen, $C_1$-$C_8$ alkyl optionally substituted with 1 to 4 halogens, or $C_3$-$C_7$ cycloalkyl-$C_0$-$C_4$ alkyl, wherein each $C_0$-$C_4$ is optionally substituted with one to four $C_1$-$C_4$ alkyl and;
$R^8$ is hydrogen, $C_1$-$C_8$ alkyl optionally substituted with 1 to 4 halogens, or $C_3$-$C_7$ cycloalkyl-$C_0$-$C_4$ alkyl;
or optionally $R^7$ and $R^8$, together with the nitrogen to which they are attached, form a 4-, 5-, 6-, or 7-membered heterocyclic ring, wherein said heterocyclic ring is optionally substituted with one or two $C_1$-$C_4$ alkyl; and wherein one of the carbons of said heterocyclic ring that is separated by at least two atoms from said nitrogen in said heterocyclic ring is optionally replaced by O, S, $NR^9$, or C=O, wherein $R^9$ is hydrogen, $C_1$-$C_8$ alkyl optionally substituted with 1 to 4 halogens, or $C_3$-$C_7$ cycloalkyl-$C_0$-$C_4$ alkyl, and wherein each $C_0$-$C_4$ alkyl is optionally substituted with one to four $C_1$-$C_4$ alkyl.

A preferred embodiment of the invention includes those compounds of formula I wherein $R^7$ and $R^8$, together with the nitrogen to which they are attached, form a 4-, 5-, 6-, or 7-membered heterocyclic ring, wherein said heterocyclic ring is optionally substituted with one or two $C_1$-$C_4$ alkyl; and wherein one of the carbons of said heterocyclic ring that is separated by at least two atoms from said nitrogen in said heterocyclic ring is optionally replaced by O, S, $NR^9$, or C=O, wherein $R^9$ is hydrogen, $C_1$-$C_8$ alkyl optionally substituted with 1 to 4 halogens, or $C_3$-$C_7$ cycloalkyl-$C_0$-$C_4$ alkyl, and wherein each $C_0$-$C_4$ alkyl is optionally substituted with one to four $C_1$-$C_4$ alkyl.

A more preferred embodiment of the invention includes those compounds of formula I wherein $R^7$ and $R^8$, together with the nitrogen to which they are attached, form a 5- or 6-membered saturated heterocycle.

The most preferred embodiment of the invention includes those compounds of formula I wherein $R^7$ and $R^8$, together with the nitrogen to which they are attached, form a pyrrolidinyl group.

Another embodiment of the invention includes those compounds of formula I wherein $R^1$ is hydrogen; $R^4$ and $R^5$ are independently hydrogen or F; $R^6$ is hydrogen or $C_1$-$C_6$ alkyl.

Another embodiment of the invention includes those compounds of formula I wherein $R^5$ is H.

Another embodiment of the invention includes those compounds of formula I wherein $R^5$ is F.

Another embodiment of the invention includes the cis cyclobutyl isomers of formula I.

Another embodiment of the invention includes the trans cyclobutyl isomers of formula I.

The most preferred embodiment of the present invention includes both the following cis and trans compounds of formula I:

3-(3-Fluoro-4-pyrrolidin-1-ylmethyl-phenyl)-cyclobutanecarboxylic acid dimethylamide;
[3-(3-Fluoro-4-pyrrolidin-1-ylmethyl-phenyl)-cyclobutyl]-pyrrolidin-1-yl-methanone;
3-(3-Fluoro-4-pyrrolidin-1-ylmethyl-phenyl)-cyclobutanecarboxylic acid ethyl-methyl-amide;
3-(3-Chloro-4-pyrrolidin-1-ylmethyl-phenyl)-cyclobutanecarboxylic acid methylamide;
3-(3-Fluoro-4-pyrrolidin-1-ylmethyl-phenyl)-cyclobutanecarboxylic acid methylamide;
{3-[3-Chloro-4-((R)-2-methyl-pyrrolidin-1-ylmethyl)-phenyl]-cyclobutyl}-pyrrolidin-1-yl-methanone;
3-(2,3-Dichloro-4-pyrrolidin-1-ylmethyl-phenyl)-cyclobutanecarboxylic acid dimethylamide;
3-(3-Fluoro-4-pyrrolidin-1-ylmethyl-phenyl)-cyclobutanecarboxylic acid ethylamide;
3-(3-Fluoro-4-pyrrolidin-1-ylmethyl-phenyl)-cyclobutanecarboxylic acid isobutyl-amide; and
(3-Aza-bicyclo[3.2.2]non-3-yl)-[3-(3-fluoro-4-pyrrolidin-1-ylmethyl-phenyl)-cyclobutyl]-methanone.
[3-Fluoro-3-(3-fluoro-4-pyrrolidin-1-ylmethyl-phenyl)-cyclobutyl]-pyrrolidin-1-yl-methanone;
3-(3-Chloro-4-pyrrolidin-1-ylmethyl-phenyl)-3-fluoro-cyclobutanecarboxylic acid dimethylamide;
[3-(3-Chloro-4-pyrrolidin-1-ylmethyl-phenyl)-3-fluoro-cyclobutyl]-piperidin-1-yl-methanone;
3-(3-Chloro-4-pyrrolidin-1-ylmethyl-phenyl)-3-fluoro-cyclobutanecarboxylic acid isobutyl-methyl-amide;
3-(3-Chloro-4-pyrrolidin-1-ylmethyl-phenyl)-3-fluoro-cyclobutanecarboxylic acid cyclopropylmethyl-amide;
[3-(3,5-Difluoro-4-pyrrolidin-1-ylmethyl-phenyl)-3-fluoro-cyclobutyl]-pyrrolidin-1-yl-methanone;
3-(2,6-Difluoro-4-pyrrolidin-1-ylmethyl-phenyl)-3-fluoro-cyclobutanecarboxylic acid methylamide;
3-(5-Chloro-2-fluoro-4-pyrrolidin-1-ylmethyl-phenyl)-3-fluoro-cyclobutanecarboxylic acid isobutyl-amide;
3-(3-Chloro-4-pyrrolidin-1-ylmethyl-phenyl)-3-fluoro-cyclobutanecarboxylic acid ethylamide;
3-(3-Chloro-4-pyrrolidin-1-ylmethyl-phenyl)-3-fluoro-cyclobutanecarboxylic acid methyl-(tetrahydro-pyran-4-ylmethyl)-amide;
3-Fluoro-3-(3-fluoro-4-pyrrolidin-1-ylmethyl-phenyl)-cyclobutanecarboxylic acid methylamide;
{3-[3-Chloro-4-((R)-2-methyl-pyrrolidin-1-ylmethyl)-phenyl]-3-fluoro-cyclobutyl}-pyrrolidin-1-yl-methanone;
3-(3-Chloro-4-pyrrolidin-1-ylmethyl-phenyl)-3-fluoro-cyclobutanecarboxylic acid cyclopropylmethyl-methyl-amide;
3-Fluoro-3-(3-fluoro-4-pyrrolidin-1-ylmethyl-phenyl)-cyclobutanecarboxylic acid dimethylamide;
3-Fluoro-3-[3-fluoro-4-((S)-2-methyl-pyrrolidin-1-ylmethyl)-phenyl]-cyclobutanecarboxylic acid ethylamide;
[3-(3-Chloro-4-pyrrolidin-1-ylmethyl-phenyl)-3-fluoro-cyclobutyl]-(2,3-dihydro-5H-benzo[f][1,4]oxazepin-4-yl)-methanone;
3-Fluoro-3-(3-fluoro-4-pyrrolidin-1-ylmethyl-phenyl)-cyclobutanecarboxylic acid ethylamide;
3-Fluoro-3-(3-fluoro-4-pyrrolidin-1-ylmethyl-phenyl)-cyclobutanecarboxylic acid ethyl-methyl-amide;
3-(3-Chloro-4-pyrrolidin-1-ylmethyl-phenyl)-3-fluoro-cyclobutanecarboxylic acid methyl-(3-methyl-pyridin-2-ylmethyl)-amide;
3-Fluoro-3-[3-fluoro-4-((R)-2-methyl-pyrrolidin-1-ylmethyl)-phenyl]-cyclobutanecarboxylic acid ethylamide;
3-Fluoro-3-(3-fluoro-4-pyrrolidin-1-ylmethyl-phenyl)-cyclobutanecarboxylic acid isobutyl-amide;
[3-Fluoro-3-(3-fluoro-4-pyrrolidin-1-ylmethyl-phenyl)-cyclobutyl]-pyrrolidin-1-yl-methanone;
[3-Fluoro-3-(3-fluoro-4-pyrrolidin-1-ylmethyl-phenyl)-cyclobutyl]-pyrrolidin-1-yl-methanone; and
3-(2,3-Dichloro-4-pyrrolidin-1-ylmethyl-phenyl)-3-fluoro-cyclobutanecarboxylic acid dimethylamide.

This invention is also directed to pharmaceutical composition for treating a disorder or condition that may be treated by antagonizing histamine-3 receptors, the composition comprising a compound of formula I and optionally a pharmaceutically acceptable carrier.

This invention is also directed to a method of treatment of a disorder or condition that may be treated by antagonizing histamine-3 receptors, the method comprising administering to a mammal in need of such treatment a compound of formula I.

This invention is also directed to a method of treatment of a disorder or condition selected from the group consisting of depression, mood disorders, schizophrenia, anxiety disorders, cognitive disorders, Alzheimer's disease, attention-deficit disorder (ADD), attention-deficit hyperactivity disorder (ADHD), psychotic disorders, sleep disorders, obesity, dizziness, epilepsy, motion sickness, respiratory diseases, allergy, allergy-induced airway responses, allergic rhinitis, nasal congestion, allergic congestion, congestion, hypotension, cardiovascular disease, diseases of the GI tract, hyper and hypo motility and acidic secretion of the gastro-intestinal tract, the method comprising administering to a mammal in need of such treatment a compound of formula I.

This invention is also directed to a pharmaceutical composition for treating allergic rhinitis, nasal congestion or allergic congestion comprising: (a) an H3 receptor antagonist compound of formula I or a pharmaceutically acceptable salt thereof; (b) an H1 receptor antagonist or a pharmaceutically acceptable salt thereof; and (c) a pharmaceutically acceptable carrier; wherein the active ingredients (a) and (b) above are present in amounts that render the composition effective in treating allergy rhinitis, nasal congestion or allergic congestion.

This invention is also directed to a pharmaceutical composition for treating ADD, ADHD, depression, mood disorders, or cognitive disorders comprising: (a) an H3 receptor antagonist compound of Formula I or a pharmaceutically acceptable salt thereof; (b) a neurotransmitter re-uptake blocker or a pharmaceutically acceptable salt thereof; (c) a pharmaceutically acceptable carrier; wherein the active ingredients (a) and (b) above are present in amounts that render the composition effective in treating depression, mood disorders, and cognitive disorders.

This invention is also directed to a process for the preparation of a compound according to formula I, wherein the process comprises the step of reacting a compound of the formula 4,

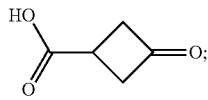

with an organometallic reagent derived from a compound of formula 2,

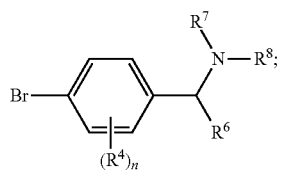

followed by the direct amide formation to yield a compound of the formula I.

In the general formula I according to the present invention, when a radical is mono- or poly-substituted, said substituent(s) can be located at any desired position(s), unless otherwise stated. Also, when a radical is polysubstituted, said substituents can be identical or different, unless otherwise stated.

The histamine-3 (H3) receptor antagonists of the invention are useful for treating, in particular, ADD, ADHD, obesity, anxiety disorders and respiratory diseases. Respiratory diseases that may be treated by the present invention include adult respiratory distress syndrome, acute respiratory distress syndrome, bronchitis, chronic bronchitis, chronic obstructive pulmonary disease, cystic fibrosis, asthma, emphysema, rhinitis and chronic sinusitis.

The pharmaceutical composition and method of this invention may also be used for preventing a relapse in a disorder or condition described in the previous paragraphs. Preventing such relapse is accomplished by administering to a mammal in need of such prevention a compound of formula I as described above.

The disclosed compounds may also be used as part of a combination therapy, including their administration as separate entities or combined in a single delivery system, which employs an effective dose of a histamine H3 antagonist compound of general formula I and an effective dose of a histamine H1 antagonist, such as cetirizine (Zyrtec™) chlorpheniramine (Chlortrimeton™), loratidine (Claritin™), fexofenadine (Allegra™), or desloratadine (Clarinex™) for the treatment of allergic rhinitis, nasal congestion, and allergic congestion.

The disclosed compounds may also be used as part of a combination therapy, including their administration as separate entities or combined in a single delivery system, which employs an effective dose of a histamine H3 antagonist compound of general formula I and an effective dose of a neurotransmitter reuptake blocker. Examples of neurotransmitter reuptake blockers will include the serotonin-selective reuptake inhibitors (SSRI's) like sertraline (Zoloft™), fluoxetine (Prozac™), and paroxetine (Paxil™), or non-selective serotonin, dopamine or norepinephrine reuptake inhibitors for treating ADD, ADHD, depression, mood disorders, or cognitive disorders.

The compounds of the present invention may have optical centers and therefore may occur in different enantiomeric configurations. Formula I, as depicted above, includes all enantiomers, diastereomers, and other stereoisomers of the compounds depicted in structural formula I, as well as racemic and other mixtures thereof. Individual isomers can be obtained by known methods, such as optical resolution, optically selective reaction, or chromatographic separation in the preparation of the final product or its intermediate.

The present invention also includes isotopically labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^{2}H$, $^{3}H$, $^{13}C$, $^{11}C$, $^{14}C$, $^{15}N$, $^{18}O$, $^{17}O$, $^{15}O$, $^{31}P$, $^{32}P$, $^{35}S$, $^{18}F$, and $^{36}Cl$, $^{123}I$ respectively. Compounds of the present invention and pharmaceutically acceptable salts of said compounds which contain the aforementioned isotopes and/or other isotopes of other atoms are within the scope of this invention. Certain isotopically labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Anxiety disorders include, for example, generalized anxiety disorder, panic disorder, PTSD, and social anxiety disorder. Mood disorders include, for example, depressed mood, mixed anxiety and depressed mood, disturbance of conduct, and mixed disturbance of conduct and depressed mood. Cognitive disorders include, for example, in addition to ADHD, attention-deficit disorder (ADD) or other attention adjustment or cognitive disorders due to general medical conditions. Psychotic disorders include, for example, schizoaffective disorders and schizophrenia; sleep disorders include, for example, narcolepsy and enuresis.

Examples of the disorders or conditions which may be treated by the compound, composition and method of this invention are also as follows: depression, including, for example, depression in cancer patients, depression in Parkinson's patients, post-myocardial infarction depression, depression in patients with human immunodeficiency virus (HIV), Subsyndromal Symptomatic depression, depression in infertile women, pediatric depression, major depression, single episode depression, recurrent depression, child abuse induced depression, post partum depression, DSM-IV major depression, treatment-refractory major depression, severe depression, psychotic depression, post-stroke depression, neuropathic pain, manic depressive illness, including manic depressive illness with mixed episodes and manic depressive illness with depressive episodes, seasonal affective disorder, bipolar depression BP I, bipolar depression BP II, or major depression with dysthymia; dysthymia; phobias, including, for example, agoraphobia, social phobia or simple phobias; eating disorders, including, for example, anorexia nervosa or bulimia nervosa; chemical dependencies, including, for example, addictions to alcohol, cocaine, amphetamine and other psychostimulants, morphine, heroin and other opioid agonists, phenobarbital and other barbiturates, nicotine, diazepam, benzodiazepines and other psychoactive substances; Parkinson's diseases, including, for example, dementia in Parkinson's disease, neuroleptic-induced parkinsonism or tardive dyskinesias; headache, including, for example, headache associated with vascular disorders; withdrawal syndrome; age-associated learning and mental disorders; apathy; bipolar disorder; chronic fatigue syndrome; chronic or acute stress; conduct disorder; cyclothymic disorder; somatoform disorders such as somatization disorder, conversion disorder, pain disorder, hypochondriasis, body dysmorphic disorder, undifferentiated disorder, and somatoform NOS; incontinence; inhalation disorders; intoxication disorders; mania; oppositional defiant disorder; peripheral neuropathy; post-traumatic stress disorder; late luteal phase dysphoric disorder; specific developmental disorders; SSRI "poop out" syndrome, or a patient's failure to maintain a satisfactory response to SSRI therapy after an initial period of satisfactory response; and tic disorders including Tourette's disease.

As an example, the mammal in need of the treatment or prevention may be a human. As another example, the mammal in need of the treatment or prevention may be a mammal other than a human.

Pharmaceutically acceptable salts of the compounds of formula I include the acid addition and base salts thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see "Handbook of Pharmaceutical Salts: Properties, Selection, and Use" by Stahl and Wermuth (Wiley-VCH, Weinheim, Germany, 2002).

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of formula I include references to salts, solvates and complexes thereof and to solvates and complexes of salts thereof.

The compounds of the invention include compounds of formula I as hereinbefore defined, including all polymorphs and crystal habits thereof, and isomers thereof (including optical, geometric and tautomeric isomers) as hereinafter defined and isotopically-labeled compounds of formula I.

Compounds of formula I containing one or more asymmetric carbon atoms can exist as two or more stereoisomers. Where structural isomers are interconvertible via a low energy barrier, tautomeric isomerism ('tautomerism') can occur. This can take the form of proton tautomerism in compounds of formula I containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of formula I, including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Unless otherwise indicated, the term "halo", as used herein, includes fluoro, chloro, bromo and iodo.

Unless otherwise indicated, the term "$(C_1\text{-}C_4)$alkyl", as used herein, includes saturated, straight-chain or branched hydrocarbon group having from 1 to 4 carbon atoms and includes for example methyl, ethyl, propyl, i-propyl, n-butyl, i-butyl, sec-butyl and t-butyl.

This also applies if the alkyl group carries substituents or is a substituent for another group, e.g. in —O—$(C_1\text{-}C_4)$alkyl and —C(O)$(C_1\text{-}C_4)$alkyl.

Unless otherwise indicated, the term "$(C_1\text{-}C_4)$alkoxy", as used herein, includes straight-chain and branched alkoxy groups and includes for example methoxy, ethoxy, n-propoxy, i-propoxy, n-butoxy, i-butoxy, sec-butoxy and t-butoxy.

Unless otherwise indicated, the term "$(C_2\text{-}C_6)$alkylene", as used herein, includes a divalent radical derived from straight-chain or branched alkane containing from 2 to 6 carbon atoms. Examples of $(C_2\text{-}C_6)$alkylene radicals are methylene, ethylene (1,2-ethylene or 1,1-ethylene), trimethylene (1,3-propylene), tetramethylene (1,4-butylene), pentamethylene and hexamethylene.

Unless otherwise indicated, the term "$(C_3\text{-}C_6)$cycloalkyl", as used herein, includes saturated monocyclic carbocyclic group having 3 to 6 carbon atoms and includes for example cyclopropyl, cyclobutyl, cyclopentyl and cyclohexyl.

Unless otherwise indicated, the term "saturated heterocycle", as used herein, includes a saturated monocyclic groups having 4 to 7 ring members, which contains 1 nitrogen atom. Examples of saturated heterocycles are azetidinyl, pyrrolidinyl and piperidinyl.

Unless otherwise indicated, the terms "heteroaromatic" as used herein, includes monocyclic or bicyclic heteroaromatic groups having 5 to 9 and 5 to 10 ring members respectively, which contain 1, 2, 3 or 4 heteroatom(s) selected from nitrogen, oxygen and sulphur. The heteroaromatic group can be unsubstituted, monosubstituted or disubstituted. Examples of heteroaryl groups include, but are not limited to thiophenyl, furanyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyranyl, pyridinyl, pyrazinyl, pyrimidinyl, pyridazinyl, triazinyl, thiadiazinyl, isobenzofuranyl, benzofuranyl, chromenyl, indolizinyl, isoindolyl, indolyl, indazolyl, purinyl, quinolinyl, isoquinolyl, cinnolinyl, phthalazinyl, naphthyridinyl, quinazolinyl, quinoxalinyl, benzoxazolyl, benzothiazolyl, benzimidazolyl, benzofuranyl, benzothiophenyl, pyrrolopyrazinyl, pyrrolopyridinyl, and imidazopyridinyl.

DETAILED DESCRIPTION OF THE INVENTION

The compound of formula I according to the invention may be prepared by the general procedure shown in Scheme 1.

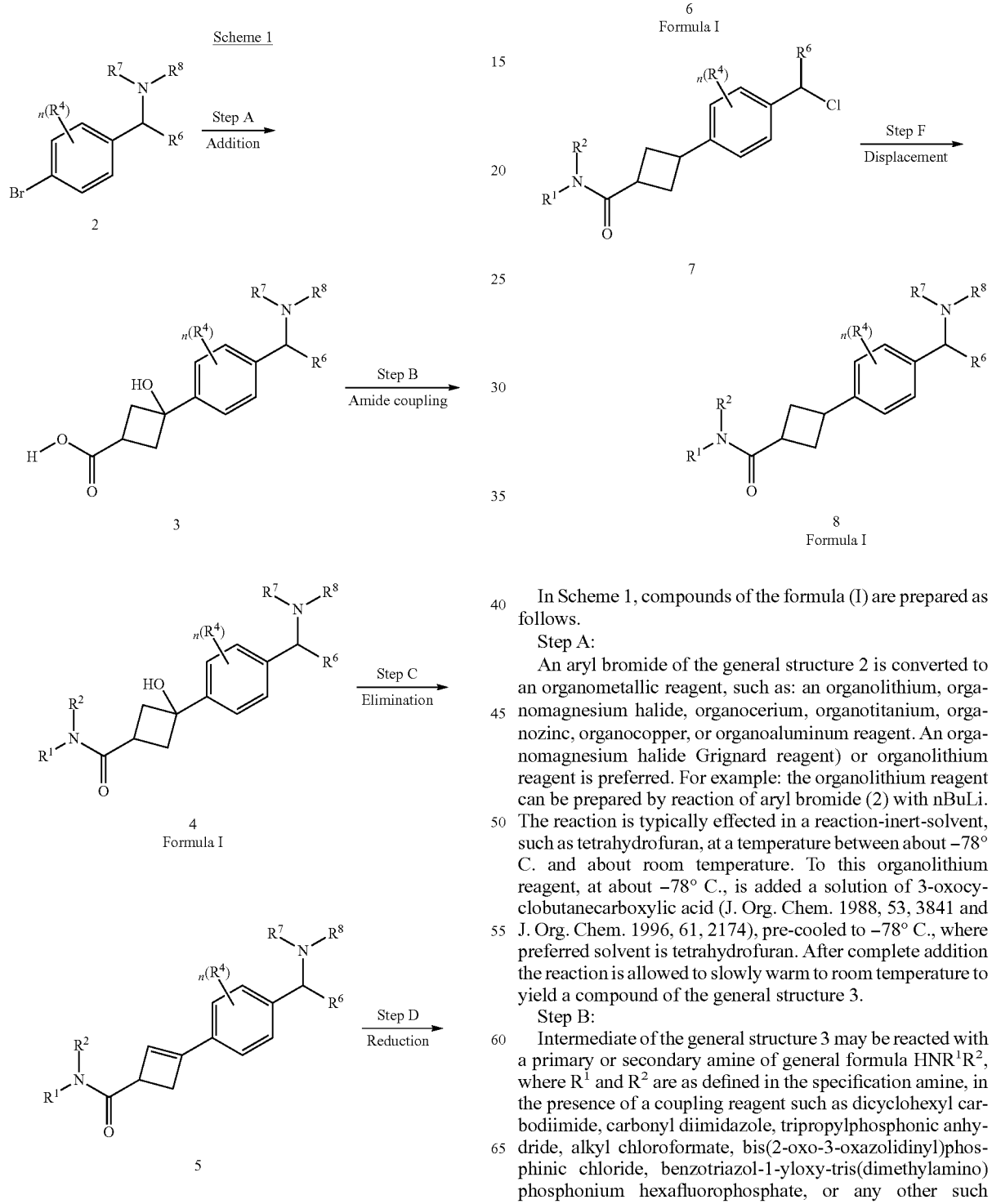

In Scheme 1, compounds of the formula (I) are prepared as follows.

Step A:

An aryl bromide of the general structure 2 is converted to an organometallic reagent, such as: an organolithium, organomagnesium halide, organocerium, organotitanium, organozinc, organocopper, or organoaluminum reagent. An organomagnesium halide Grignard reagent) or organolithium reagent is preferred. For example: the organolithium reagent can be prepared by reaction of aryl bromide (2) with nBuLi. The reaction is typically effected in a reaction-inert-solvent, such as tetrahydrofuran, at a temperature between about −78° C. and about room temperature. To this organolithium reagent, at about −78° C., is added a solution of 3-oxocyclobutanecarboxylic acid (J. Org. Chem. 1988, 53, 3841 and J. Org. Chem. 1996, 61, 2174), pre-cooled to −78° C., where preferred solvent is tetrahydrofuran. After complete addition the reaction is allowed to slowly warm to room temperature to yield a compound of the general structure 3.

Step B:

Intermediate of the general structure 3 may be reacted with a primary or secondary amine of general formula $HNR^1R^2$, where $R^1$ and $R^2$ are as defined in the specification amine, in the presence of a coupling reagent such as dicyclohexyl carbodiimide, carbonyl diimidazole, tripropylphosphonic anhydride, alkyl chloroformate, bis(2-oxo-3-oxazolidinyl)phosphinic chloride, benzotriazol-1-yloxy-tris(dimethylamino) phosphonium hexafluorophosphate, or any other such standard literature reagents in the presence of a trialkyl amine base, such as triethyl amine or diisopropylethyl amine, wherein tripropylphosphonic anhydride and triethylamine are a preferred combination in a reaction-inert-solvent, where ethyl acetate is preferred, from −78° C. to 40° C., where room temperature is preferred, to afford the N-acylated compounds of the general structure 4, a compound of Formula I.

Step C:

Elimination of the benzyl alcohol (4) is accomplished by reaction of (4) with an acid, preferably with trifluoroacetic acid, either neat or in a reaction-inert-solvent, such as methylene chloride or 1,2-dichloroethane at a reaction temperature from about room temperature to the reflux temperature of the solvent employed, where about 75° C. is the preferred reaction temperature, to yield a compound with the general structure 5.

Step D:

Reduction of the cyclobutene, (5) can be accomplished by reaction of (5) in a reaction-inert-solvent, where preferred solvents are ethyl alcohol and ethyl acetate. The reduction can be accomplished using hydrogen gas at about 45 psi and a catalyst, where preferred hydrogenation catalysts are Wilkinson's catalyst [chlorotris(triphenylphosphine)rhodium(I)], or palladium, 5-10 wt % on activated carbon to give (6), a compound of the general Formula I.

Step E:

Conversion of benzyl amines of the general structure (6) to benzyl chlorides of the general structure (7) is accomplished using condition described in the literature, for example (Nevill, C. R.; Fuchs, P. L.; SYNCAV; Synth. Commun.; EN; 20; 5; 1990; 761-772). Reaction of (6) with ethyl chloroformate in a reaction-inert-solvent, where 1,2-dichloroethane, or methylene chloride are preferred at a reaction temperature from about −78° C. to room temperature, where room temperature is preferred, gives benzyl chlorides of the general structure (7).

Step F:

Reaction of the benzyl chloride (7) with a primary or secondary amine of general formula HNR¹R², where R¹ and R² are as defined in the specification amine, in a reaction-inert-solvent, where 1,2-dichlorethane or methylene chloride are preferred, in the presence of a tertiary amine base, where triethylamine is preferred, at a reaction temperature from about room temperature to the reflux temperature of the solvent employed, about 55° C. is preferred, gives (8), a compound of the general formula I.

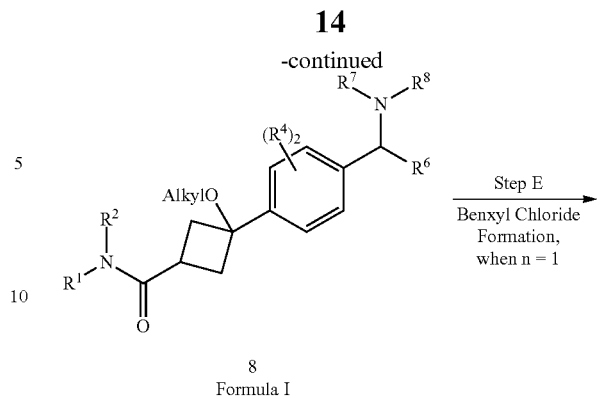

In Scheme 2, compounds of the formula (I) are prepared as follows.

Step G:

Fisher etherification can be accomplished using standard conditions that appear in the literature and known to those skilled in the art. For example: reaction of hydroxyl (4) with an alkyl halide, such as: alkyl chloride, alkyl bromide, or alkyl iodide in the presence of a base where NaH is preferred, and in the presence of NaI or NaBr, in a reaction-inert-solvent, where dimethyl formamide is preferred, at a reaction temperature of room temperature to 100° C., where 65° C. is preferred gives (8), a compound of the formula I.

Step E:
(See Step E above)
Step F:
(See Step F above)

Scheme 3

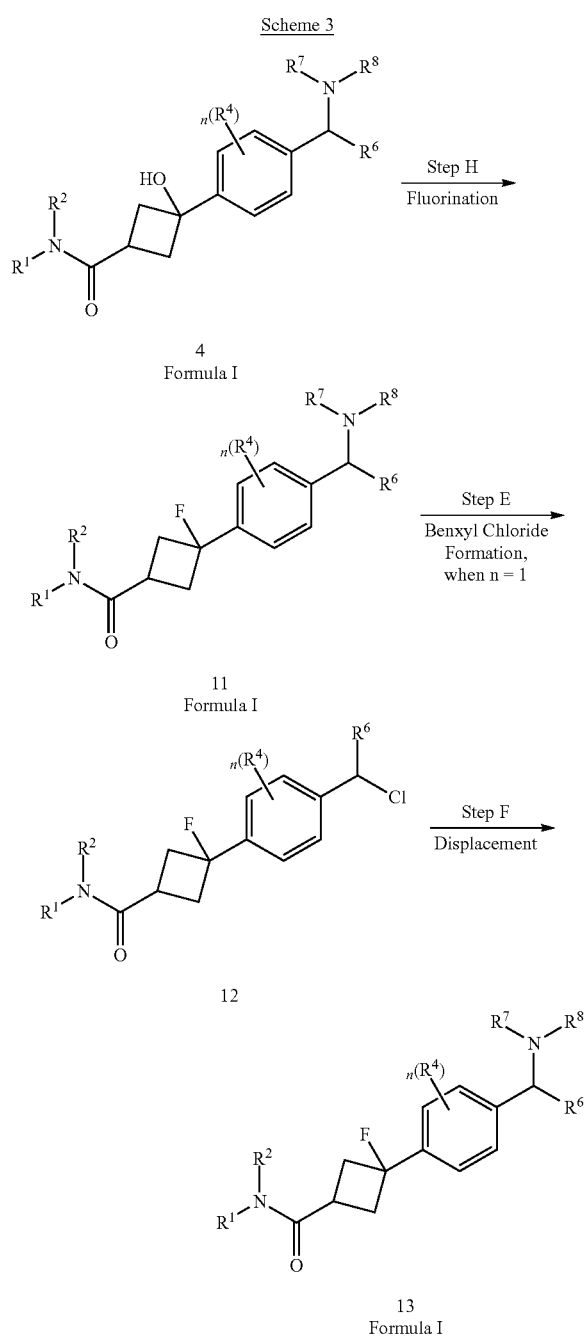

In Scheme 3, compounds of the formula (I) are prepared as follows.

Step H:

Reaction of a compound of the general structure (4) with a fluorinating reagent gives compounds of the general formula 13. Several reagents are available for conversion of alcohols to alkyl fluorides, for example, Caldwell, Charles G; et al (Bioorg. Med. Chem. Lett.; EN; 14; 5; 2004; 1265-1268) utilizes BAST. Other examples in the literature utilize DAST for the direct conversion of alcohols to alkyl fluorides. Reaction of hydroxyl (3) with bis(2-methoxyethyl)aminosulfur trifluoride in a reaction-inert-solvent, where methylene chloride or tetrahydrofuran is preferred, at a reaction temperature from about −78° C. to room temperature gives (11), a compound of the formula I.

Step E:
(see Step E above)
Step F:
(see Step F above)

Exemplary compounds of formula I in accordance with the present invention are the following:

N-Methyl-2-pyridin-3-yl-N-[3-(4-pyrrolidin-1-ylmethyl-phenoxy)-cyclobutylmethyl]-acetamide;

[3-Hydroxy-3-(4-pyrrolidin-1-ylmethyl-phenyl)-cyclobutyl]-morpholin-4-yl-methanone;

3-(3-Chloro-4-pyrrolidin-1-ylmethyl-phenyl)-3-hydroxy-cyclobutanecarboxylic acid methylamide;

3-(3-Chloro-4-pyrrolidin-1-ylmethyl-phenyl)-cyclobutanecarboxylic acid methylamide;

3-(3-Fluoro-4-pyrrolidin-1-ylmethyl-phenyl)-3-hydroxy-cyclobutanecarboxylic acid methylamide;

3-(3-Fluoro-4-pyrrolidin-1-ylmethyl-phenyl)-cyclobutanecarboxylic acid methylamide;

3-(3-Chloro-4-pyrrolidin-1-ylmethyl-phenyl)-3-hydroxy-cyclobutanecarboxylic acid dimethylamide;

[3-(3-Chloro-4-pyrrolidin-1-ylmethyl-phenyl)-3-hydroxy-cyclobutyl]-piperidin-1-yl-methanone;

3-(3-Chloro-4-pyrrolidin-1-ylmethyl-phenyl)-3-hydroxy-cyclobutanecarboxylic acid isobutyl-methyl-amide;

3-(3-Chloro-4-pyrrolidin-1-ylmethyl-phenyl)-3-hydroxy-cyclobutanecarboxylic acid cyclopropylmethyl-amide;

3-(3-Chloro-4-pyrrolidin-1-ylmethyl-phenyl)-3-hydroxy-cyclobutanecarboxylic acid methyl-(tetrahydro-pyran-4-ylmethyl)-amide;

3-(3-Chloro-4-pyrrolidin-1-ylmethyl-phenyl)-3-hydroxy-cyclobutanecarboxylic acid cyclopropylmethyl-methyl-amide;

[3-(3-Chloro-4-pyrrolidin-1-ylmethyl-phenyl)-3-hydroxy-cyclobutyl]-(2,3-dihydro-5H-benzo[f][1,4]oxazepin-4-yl)-methanone;

3-(3-Chloro-4-pyrrolidin-1-ylmethyl-phenyl)-3-hydroxy-cyclobutanecarboxylic acid methyl-(3-methyl-pyridin-2-ylmethyl)-amide;

3-(3-Fluoro-4-pyrrolidin-1-ylmethyl-phenyl)-3-hydroxy-cyclobutanecarboxylic acid dimethylamide;

[3-(3-Fluoro-4-pyrrolidin-1-ylmethyl-phenyl)-3-hydroxy-cyclobutyl]-pyrrolidin-1-yl-methanone;

3-(3-Fluoro-4-pyrrolidin-1-ylmethyl-phenyl)-3-hydroxy-cyclobutanecarboxylic acid isobutyl-amide;

3-(3-Fluoro-4-pyrrolidin-1-ylmethyl-phenyl)-3-hydroxy-cyclobutanecarboxylic acid ethylamide;

3-(3-Fluoro-4-pyrrolidin-1-ylmethyl-phenyl)-3-hydroxy-cyclobutanecarboxylic acid ethyl-methyl-amide;

3-(3-Fluoro-4-pyrrolidin-1-ylmethyl-phenyl)-cyclobutanecarboxylic acid dimethylamide;

3-(3-Chloro-4-pyrrolidin-1-ylmethyl-phenyl)-3-fluoro-cyclobutanecarboxylic acid dimethylamide;

[3-(3-Fluoro-4-pyrrolidin-1-ylmethyl-phenyl)-cyclobutyl]-pyrrolidin-1-yl-methanone;

3-(3-Fluoro-4-pyrrolidin-1-ylmethyl-phenyl)-cyclobutanecarboxylic acid isobutyl-amide;

3-(3-Fluoro-4-pyrrolidin-1-ylmethyl-phenyl)-cyclobutanecarboxylic acid ethylamide;

3-(3-Fluoro-4-pyrrolidin-1-ylmethyl-phenyl)-cyclobutanecarboxylic acid ethyl-methyl-amide;

[3-(3-Chloro-4-pyrrolidin-1-ylmethyl-phenyl)-3-fluoro-cyclobutyl]-piperidin-1-yl-methanone;

3-(3-Chloro-4-pyrrolidin-1-ylmethyl-phenyl)-3-fluoro-cyclobutanecarboxylic acid isobutyl-methyl-amide;

3-(3-Chloro-4-pyrrolidin-1-ylmethyl-phenyl)-3-fluoro-cyclobutanecarboxylic acid cyclopropylmethyl-amide;

3-(3-Chloro-4-pyrrolidin-1-ylmethyl-phenyl)-cyclobutanecarboxylic acid methylamide;
3-(3-Fluoro-4-pyrrolidin-1-ylmethyl-phenyl)-cyclobutanecarboxylic acid methylamide;
3-(2,6-Difluoro-4-pyrrolidin-1-ylmethyl-phenyl)-3-fluoro-cyclobutanecarboxylic acid methylamide;
3-(3-Chloro-4-pyrrolidin-1-ylmethyl-phenyl)-3-fluoro-cyclobutanecarboxylic acid methyl-(tetrahydro-pyran-4-ylmethyl)-amide;
3-(3-Chloro-4-pyrrolidin-1-ylmethyl-phenyl)-3-fluoro-cyclobutanecarboxylic acid cyclopropylmethyl-methyl-amide;
[3-(3-Chloro-4-pyrrolidin-1-ylmethyl-phenyl)-3-fluoro-cyclobutyl]-(2,3-dihydro-5H-benzo[f][1,4]oxazepin-4-yl)-methanone;
3-(3-Chloro-4-pyrrolidin-1-ylmethyl-phenyl)-3-fluoro-cyclobutanecarboxylic acid methyl-(3-methyl-pyridin-2-ylmethyl)-amide;
[3-(3,5-Difluoro-4-pyrrolidin-1-ylmethyl-phenyl)-3-hydroxy-cyclobutyl]-pyrrolidin-1-yl-methanone;
[3-(3,5-Difluoro-4-pyrrolidin-1-ylmethyl-phenyl)-3-fluoro-cyclobutyl]-pyrrolidin-1-yl-methanone;
3-(5-Chloro-2-fluoro-4-pyrrolidin-1-ylmethyl-phenyl)-3-hydroxy-cyclobutanecarboxylic acid isobutyl-amide;
3-(5-Chloro-2-fluoro-4-pyrrolidin-1-ylmethyl-phenyl)-3-fluoro-cyclobutanecarboxylic acid isobutyl-amide;
3-Fluoro-3-(3-fluoro-4-pyrrolidin-1-ylmethyl-phenyl)-cyclobutanecarboxylic acid methylamide;
3-Fluoro-3-(3-fluoro-4-pyrrolidin-1-ylmethyl-phenyl)-cyclobutanecarboxylic acid dimethylamide;
3-Fluoro-3-(3-fluoro-4-pyrrolidin-1-ylmethyl-phenyl)-cyclobutanecarboxylic acid ethylamide;
3-Fluoro-3-(3-fluoro-4-pyrrolidin-1-ylmethyl-phenyl)-cyclobutanecarboxylic acid ethyl-methyl-amide;
3-Fluoro-3-(3-fluoro-4-pyrrolidin-1-ylmethyl-phenyl)-cyclobutanecarboxylic acid isobutyl-amide;
3-(3-Fluoro-4-pyrrolidin-1-ylmethyl-phenyl)-3-methoxy-cyclobutanecarboxylic acid ethyl-methyl-amide;
[3-Fluoro-3-(3-fluoro-4-pyrrolidin-1-ylmethyl-phenyl)-cyclobutyl]-pyrrolidin-1-yl-methanone;
3-(2,3-Dichloro-4-pyrrolidin-1-ylmethyl-phenyl)-3-fluoro-cyclobutanecarboxylic acid dimethylamide;
3-(2,3-Dichloro-4-pyrrolidin-1-ylmethyl-phenyl)-3-hydroxy-cyclobutanecarboxylic acid dimethylamide;
{3-[3-Chloro-4-((R)-2-methyl-pyrrolidin-1-ylmethyl)-phenyl]-3-hydroxy-cyclobutyl}-pyrrolidin-1-yl-methanone;
3-(3-Chloro-4-pyrrolidin-1-ylmethyl-phenyl)-3-hydroxy-cyclobutanecarboxylic acid ethylamide;
3-(3-Chloro-4-pyrrolidin-1-ylmethyl-phenyl)-3-fluoro-cyclobutanecarboxylic acid ethylamide;
{3-[3-Chloro-4-((R)-2-methyl-pyrrolidin-1-ylmethyl)-phenyl]-3-fluoro-cyclobutyl}-pyrrolidin-1-yl-methanone;
{3-[3-Chloro-4-((R)-2-methyl-pyrrolidin-1-ylmethyl)-phenyl]-cyclobutyl}-pyrrolidin-1-yl-methanone;
3-(2,3-Dichloro-4-pyrrolidin-1-ylmethyl-phenyl)-cyclobutanecarboxylic acid dimethylamide;
3-Fluoro-3-[3-fluoro-4-((S)-2-methyl-pyrrolidin-1-ylmethyl)-phenyl]-cyclobutanecarboxylic acid ethylamide;
3-Fluoro-3-[3-fluoro-4-((R)-2-methyl-pyrrolidin-1-ylmethyl)-phenyl]-cyclobutanecarboxylic acid ethylamide;
3-(3-Fluoro-4-pyrrolidin-1-ylmethyl-phenyl)-cyclobutanecarboxylic acid ethylamide;
3-(3-Fluoro-4-pyrrolidin-1-ylmethyl-phenyl)-cyclobutanecarboxylic acid isobutyl-amide; and
3-aza-bicyclo[3.2.2]nonan-3-yl(3-(3-fluoro-4-(pyrrolidin-1-ylmethyl)phenyl)-3-hydroxycyclobutyl)methanone.

In the examples below the following terms are intended to have the following, general meaning:
BAST: [BIS(2-METHOXYETHYL)AMINO]SULFUR TRIFLUORIDE
Deoxo-Fluor: [BIS(2-METHOXYETHYL)AMINO]SULFUR TRIFLUORIDE
$T_3P$: 2,4,6-tripropyl-1,3,5,2,4,6-trioxatriphosphorinane-2,4,6-trioxide
DIPEA: diisopropylethylamine DMF: dimethyformamide
$MgSO_4$: magnesium sulfate DMA: dimethyl acetamide
LRMS: low resolution mass spectrometry ° C.: degrees Celsius
calcd: calculated d: day(s); doublet (spectral) DCE: 1,2-dichloroethane
EtOAc: ethyl acetate g: grams
hr: hours Hz: hertz
J: coupling constant (in NMR) L: liter(s)
LAH: lithium aluminum hydride MHz: megahertz
m/z: mass to charge ratio (mass spectrometry) Min: minute(s)
obsd: observed PPTs: pyridinium p-toluenesulfonate
TsO: p-toluenesulfonate Rf: retention factor (in chromatography) Rt: retention time (in chromatography) rt: room temperature
s: singlet (NMR); second(s) t: triplet
TFA: trifluoroacetic acid TFAA: trifluoroacetic anhydride
THF: tetrahydrofuran TLC: thin layer chromatography
Ts: tosyl, p-toluenesulfonyl TsOH: p-toluenesulfonic acid
apt: apparent triplet Solvents were purchased and used without purification. Yields were calculated for material judged homogenous by thin layer chromatography and NMR. Thin layer chromatography was performed on Merck Kieselgel 60 F 254 plates eluting with the solvents indicated, visualized by a 254 nm UV lamp, and stained with either an aqueous $KMnO_4$ solution or an ethanolic solution of 12-molybdophosphoric acid. Flash column chromatography unless otherwise stated, was performed with using either pre-packed Biotage™ or ISCO™ columns using the size indicated. Nuclear magnetic resonance (NMR) spectra were acquired on a Unity 400 or 500 at 400 MHz or 500 MHz for $^1H$, respectively, and 100 MHz or 125 MHz for $^{13}C$ NMR, respectively. Chemical shifts for proton $^1H$ NMR spectra are reported in parts per million relative to the singlet of $CDCl_3$ at 7.24 ppm. Chemical shifts for $^{13}C$ NMR spectra are reported in parts per million downfield relative to the centerline of the triplet of $CDCl_3$ at 77.0 ppm. Mass spectra analyses were performed on a APCI Gilson 215, micromass ZMD (50% Acetonitrile/50% water) spectrometer.

HPLC was performed according to the following methods:
Method A: Preparative conditions (Waters 600 & Waters 2767 Sample Manager); Column: Waters Symmetry $C_{18}$, 5 µm, 30×150 mm steel column, part # WAT248000, serial # M12921A01; solvent A—0.1% Trifluoroacetic acid/water; solvent B—Acetonitrile; volume of injection: 850 µL; time 0.0, 100% solvent A, 0% solvent B, flow 20; time 2.0, 100% solvent A, 0% solvent B, flow 20; time 12.0, 0% solvent A, 100% solvent B, flow 20; time 15.0, 0% solvent A, 100% solvent B, flow 20; time 15.1, 100% solvent A, 0% solvent B, flow 20; time 20.0, 100% solvent A, 0% solvent B, flow 20.

Mass spectral (micromassZO) conditions; Capillary (kV): 3.0; Cone (V): 20; Extractor (V): 3.0; RF Lens (V): 0.5; Source temp. (° C.): 120; Desolvation temp. (° C.): 360; Desolvation gas flow (Uhr): 450; Cone gas flow (Uhr): 150; LM Resolution: 15; HM Resolution: 15; Ion Energy: 0.2; Multiplier: 550.

Splitter; Acurate by LC Packings, 1/10,000; Upchurch needle valve setting: 14; Make up pump (Waters 515) Flow (ml/min.): 1.

PDA (Waters 996) Settings; Start/End wavelength (nm): 200/600; Resolution: 1.2; Sample Rate: 1; Channels: TIC, 254 nm and 220 nm.

Method B: Preparative conditions (Waters 600 & Waters 2767 Sample Manager); Column: Waters Xterra PrepMS $C_{18}$ column, 5 µm, 30×150 mm steel column, part #186001120, serial # T22881T 09; solvent A—0.1% Trifluoroacetic acid/water; solvent B—

Acetonitrile; volume of injection: 1050 µL; time 0.0, 100% solvent A, 0% solvent B, flow 20;

time 2.0, 100% solvent A, 0% solvent B, flow 20; time 12.0, 0% solvent A, 100% solvent B, flow 20; time 14.0, 0% solvent A, 100% solvent B, flow 20; time 14.1, 100% solvent A, 0% solvent B, flow 20; time 19.1, 100% solvent A, 0% solvent B, flow 20.

Mass spectral (micromassZO) conditions; Capillary (kV): 3.0; Cone (V): 20; Extractor (V): 3.0; RF Lens (V): 0.5; Source temp. (° C.): 120; Desolvation temp. (° C.): 360; Desolvation gas flow (Uhr): 450; Cone gas flow (Uhr): 150; LM Resolution: 15; HM Resolution: 15; Ion Energy: 0.2; Multiplier: 550.

Splitter; Acurate by LC Packings, 1/10,000; Upchurch needle valve setting: 14; Make up pump (Waters 515) Flow (ml/min.): 1.

PDA (Waters 996) Settings; Start/End wavelength (nm): 200/600; Resolution: 1.2; Sample Rate: 1; Channels: TIC, 254 nm and 220 nm.

Method C: Preparative conditions (Waters 600 & Waters 2767 Sample Manager); Column: Waters Symmetry $C_{18}$, 5 µm, 30×150 mm steel column, part # WAT248000, serial # M12921A01; solvent A—0.1% Trifluoroacetic acid/water; solvent B—Acetonitrile; volume of injection: 850 µL; time 0.0, 90% solvent A, 10% solvent B, flow 20; time 10.0, 0% solvent A, 100% solvent B, flow 20; time 12.0, 0% solvent A, 100% solvent B, flow 20.

Mass spectral (micromassZO) conditions; Capillary (kV): 3.0; Cone (V): 20; Extractor (V): 3.0; RF Lens (V): 0.5; Source temp. (° C.): 120; Desolvation temp. (° C.): 360; Desolvation gas flow (Uhr): 450; Cone gas flow (Uhr): 150; LM Resolution: 15; HM Resolution: 15; Ion Energy: 0.2; Multiplier: 550.

Splitter; Acurate by LC Packings, 1/10,000; Upchurch needle valve setting: 14; Make up pump (Waters 515) Flow (ml/min.): 1.

PDA (Waters 996) Settings; Start/End wavelength (nm): 200/600; Resolution: 1.2; Sample Rate: 1; Channels: TIC, 254 nm and 220 nm.

The following intermediates may be prepared by the procedures shown:

Intermediate 1

1-(2,3-Dichlorobenzyl)pyrrolidine

NaHB(OAc)$_3$ (15.1 g, 0.0714 mmol) was added under vigorous stirring in portions to a solution of 2,3-dichlorobenzaldehyde (10 g, 0.057 mmol) and pyrrolidine (5.97 mL, 0.0714 mmol) in CH$_2$Cl$_2$ (200 mL). The reaction mixture was vigorously stirred overnight. Then 5N NaOH (50 mL) was added, and the layers were separated. The product was extracted from the aqueous layer with CH$_2$Cl$_2$ (2×50 mL). The combined extracts were washed with 5N NaOH (50 mL), water, brine, dried with anhydrous Na$_2$SO$_4$, and evaporated. The residue was distilled in vacuum to give title compound (10.5 g, 90%) as a colorless liquid (bp 80-84° C./0.5 mmHg). LC/MS data: 229.9, 230.9, 231.9 (M+H) (calculated for $C_{11}H_{13}Cl_2N$ 230.14). $^1$H NMR data (DMSO-d6): δ 7.52 (dd, 1H, J1=1.5 Hz, J2=7.8 Hz), 7.46 (dd, 1H, J1=1.5 Hz, J2=7.8 Hz), 7.33 (t, 1H, J=7.8 Hz), 3.70 (s, 2H), 2.46-2.52 (m, 4H), 1.66-1.75 (m, 4H).

Example 1

3-[2,3-Dichloro-4-(pyrrolidin-1-ylmethyl)phenyl]-3-hydroxy-N,N-dimethylcyclobutanecarboxamide A 1.3 M solution of s-BuLi in cyclohexane (3.7 mL, 4.8 mmol) was added over 5 min to a solution of Intermediate 1,1-(2,3-dichlorobenzyl)pyrrolidine (1.0 g, 4.4 mmol) and TMEDA (0.73 ml, 4.8 mmol) in absolute THF (10 ml) in a flow of argon at −90 to −100° C. The reaction mixture was stirred at −85 to −90° C. for 30 min. Then a solution of 3-oxocyclobutanecarboxylic acid (250 mg, 2.2 mmol), (J. Org. Chem. 1988, 53, 3841 and J. Org. Chem. 1996, 61, 2174) in THF (2 mL) was added drop wise over 2 min at −100° C. The mixture was then warmed to 0° C. for 30 min and evaporated to dryness. The residue was dissolved in DMF (10 mL), and dimethylamine hydrochloride (410 mg, 5.0 mmol) was added. Then BOP (1.3 g, 3.0 mmol) was added in portions under cooling in an ice bath. The reaction mixture was stirred for 16 h at room temperature. The disappearance of the starting hydroxy acid was monitored by LC/MS. The reaction mass was evaporated to dryness under 1 mmHg. Water (10 mL), Et$_2$O (15 mL), and a saturated solution of K$_2$CO$_3$ (5 mL) were added. The layers were separated, and the aqueous one was subjected to extraction with Et$_2$O (2×20 mL). The combined organic layer was dried with Na$_2$SO$_4$, and evaporated. The residue was purified by chromatography (30 mL of silica gel 63/100 µm, CHCl$_3$/MeOH 100:0→90:10). The product containing fractions were collected, concentrated under reduced pressure to yield the title compound (0.30 g, 37%). LC/MS data: 371.0, 372.0, 373.0 (M+H) (calculated for $C_{18}H_{24}Cl_2N_2O_2$ 371.31); $^1$H NMR data (DMSO-d6): δ 7.57 (d, 1H, ArH, J=8.0 Hz), 7.43 (d, 1H, ArH, J=8.0 Hz), 5.59 (s, 1H, OH), 3.71 (s, 2H, CH2Ar), 2.88-2.97 (m, 2H), 2.86 (s, 3H NMe), 2.82 (s, 3H, NMe), 2.67-2.78 (m, 1H), 2.50-2.57 (m, 6H+DMSO), 1.67-1.77 (m, 4H). The HCl salt was made using HCl, ether. A 8 mL screw cap vial was charged with 3-[2,3-dichloro-4-(pyrrolidin-1-ylmethyl)phenyl]-3-hydroxy-N,N-dimethylcyclobutanecarboxamide (60 mg, 0.161 mmol) and 0.5 mL of MeOH. Then 0.2 mL of 2M HCl in ether was added, evaporated and dried to give oil, which was redissolved in 1 mL of DCM, evaporated and dried to give 62 mg of white hygroscopic solid of HCl salt. LCMS (M+H): 371.1; $^1$H NMR (300 MHz, DMSO-d$_6$): δ 10.57 (br. s, 1H), 7.80 (d, J=8.1 Hz, 1H), 7.73 (d, J=8.2 Hz, 1H), 4.57 (d, J=5.64 Hz, 2H), 3.50-3.70 (m, 3H), 3.40-3.50 (m, 3H), 2.90-2.97 (m, 2H), 2.86 (s, 3H), 2.83 (s, 3H), 2.69-2.75 (m, 1H), 2.03-2.07 (m, 2H), 1.80-1.94 (m, 2H).

Intermediate 2

3-[2,3-dichloro-4-(pyrrolidin-1-ylmethyl)phenyl]-N,N-dimethylcyclobut-2-ene-1-carboxamide, trifluoroacetate A solution of 3-[2,3-dichloro-4-(pyrrolidin-1-ylmethyl)phenyl]-3-hydroxy-N,N-dimethylcyclobutanecarboxamide (250 mg, 0.673 mmol) and TFA (1.04 ml, 13.5 mmol) in 5 ml of DCE was refluxed under argon for 6 h, then additional amount of TFA (1.04 ml, 13.5 mmol) was added and the mixture was refluxed for 20 h. The mixture was evaporated to dryness. According to LCMS data the reaction mixture contained up to 70% of the title compound (353, 354, 355 (M+H) (calculated for $C_{18}H_{22}Cl_2N_2O$ 353.29)). The mixture was used for the next step without additional purification.

Example 2 trans-3-[2,3-Dichloro-4-(pyrrolidin-1-ylmethyl)phenyl]-N,N-dimethylcyclobutanecarboxamide, hydrochloride To a solution of intermediate 2, 3-[2,3-dichloro-4-(pyrrolidin-1-ylmethyl)phenyl]-N,N-dimethylcyclobut-2-ene-1-carboxamide, trifluoroacetate (0.673 mmol) in 5 mL of ethanol was added chlorotris(triphenylphosphine)rhodium(I) (63 mg, 0.0673 mmol). The mixture was hydrogenated (40 psi $H_2$, 50° C.) for 3 h; the reaction was monitored by LCMS. The mixture was evaporated to dryness, then 5 ml of 1N HCl was added to the residue and the solution was extracted with ethyl acetate (2×5 ml), the organic layers were discarded. 10N NaOH (1 mL) was added to the water layer and the water solution was extracted with ethyl acetate (3×5 mL). The organic layers were dried and evaporated in vacuum. The residue was purified by chromatography ($SiO_2$ 63/100 μm, 10 g, $CHCl_3$/hexane 80:20→100:0, $CHCl_3$/MeOH 100:0→90:10). Fractions containing the product were evaporated. The residue was dissolved in 2 ml of ether and 0.1 mL of 4N HCl/dioxane was added under stirring. The mixture was evaporated; the residue was dried in vacuum to afford the title compound (74 mg, 28%) as a white solid. LCMS data: 355, 356, and 357 $(M+H)^+$ (calculated for $C_{18}H_{24}Cl_2N_2O$ 355.31). $^1H$ NMR data ($CD_3OD$): δ 7.69 (d, 1H, J=8.1 Hz), 7.58 (d, 1H, J=8.1 Hz), 4.62 (s, 2H), 3.88-3.98 (m, 1H), 3.54-3.63 (m, 2H), 3.35-3.45 (m, 1H), 3.25-3.34 (m, 2H+MeOH), 2.99 (s, 6H), 2.71-2.79 (m, 2H), 2.42-2.52 (m, 2H), 2.16-2.27 (m, 2H), 1.98-2.12 (m, 2H).

Example 3

3-[2,3-dichloro-4-(pyrrolidin-1-ylmethyl)phenyl]-3-fluoro-N,N-dimethylcyclobutanecarboxamide hydrochloride An 8 mL screw cap vial, equipped with a magnetic stirring bar and septum cap, was charged with Deoxo-Fluor (Aldrich, 85.5 mg, 0.387 mmol) and 3 mL of anhydrous DCM under nitrogen. Then the mixture was cooled to −75° C. and a solution of Example 1,3-[2,3-dichloro-4-(pyrrolidin-1-ylmethyl)phenyl]-3-hydroxy-N,N-dimethylcyclobutanecarboxamide (130 mg, 0.350 mmol) in 2 mL of anhydrous DCM was added. The mixture was stirred for 1 h at −75° C., then sampled for LCMS, which showed 60% conversion. Then another Deoxo-Fluor (Aldrich, 85.5 mg, 0.387 mmol) was added, stirred at −75° C. for 10 min, warmed to 0° C. and quenched with sat. $Na_2CO_3$ (2 mL). LCMS showed complete conversion. Then 1 mL of 2N NaOH was added and the DCM layer was separated, dried over $Na_2SO_4$, and evaporated. The crude oil was purified by column (from DCM 99%, $NH_4OH$ 1% to DCM 98%, MeOH 1%, $NH_4OH$ 1%, Rf=0.51 in DCM 99%, $NH_4OH$ 1%) to give 117 mg (90%) of the product as colorless oil. This material was dissolved in 0.5 mL of MeOH, then 0.3 mL of 2M HCl in ether was added, evaporated and dried to give oil, which was redissolved in 1 mL of DCM, evaporated and dried to give the title compound (118 mg) of a white hygroscopic solid, HCl salt. LCMS (M+H): 373.3; $^1H$ NMR (300 MHz, DMSO-$d_6$): δ 10.27 (br. s, 1H), 7.81 (d, J=7.71 Hz, 1H), 7.65 (dd, J1=8.1 Hz, J2=2.07 Hz, 1H), 4.59 (d, J=5.64 Hz, 2H), 3.62-3.71 (m, 6H), 3.45-3.50 (m, 2H), 2.95 (s, 3H), 2.85-2.88 (m, 1H), 2.80 (s, 3H), 2.00-2.10 (m, 2H), 1.80-1.91 (m, 2H).

Intermediate 3

4-Bromo-1-(bromomethyl)-2-chlorobenzene

4-Bromo-2-chloro-1-methylbenzene (CAS 89794-02-5, 30 g, 0.15 mol) and N-bromosuccinimide (26 g, 0.15 mol) were mixed in $CCl_4$ (300 mL). Azobis(2-methylpropionitrile) (~0.3 g) was added in portions under vigorous stirring and refluxing. The mixture was refluxed for 30 min and cooled. The precipitate was filtered off and discarded. The filtrate was evaporated. The residue was distilled at 1 mmHg, by 75° C. to give the title compound (28 g, 65%). $^1H$ NMR data ($CDCl_3$): δ 7.57 (d, J=1.9 Hz, 1H ArH), 7.39 (dd, 1H, $J_1$=1.9 Hz, $J_2$=8.1 Hz, ArH), 7.31 (d, 1H, J=1.9 Hz, ArH), 4.53 (s, 2H, $ArCH_2$).

Intermediate 4

(2R)-1-(4-bromo-2-chlorobenzyl)-2-methylpyrrolidine

Intermediate 3,4-bromo-1-(bromomethyl)-2-chlorobenzene (15.4 g, 55 mmol) was added to a mixture of (2R)-2-methylpyrrolidine HBr (9.0 g, 55 mmol), potassium carbonate (18 g, 130 mmol), and 150 mL of dimethylformamide under ice cooling. The mixture was allowed to reach room temperature, and the stirring was continued overnight. The mixture was evaporated. Water (400 mL) was added followed by addition of 5M $NaHSO_4$ to attain pH~2. The organic layer was separated. The aqueous phase was extracted with $Et_2O$ (2×200 mL). The organic layers were discarded. The aqueous fraction was alkalized with $K_2CO_3$ to pH~12 and subjected to extraction with $Et_2O$ (2×300 mL). The organic layer was washed with brine, dried over anhydrous $Na_2SO_4$ (100 g), and evaporated in vacuo. The residue was distilled at 1 mmHg, by 95° C. to give the title compound (12.25 g, 79%). LC/MS data: 289.9 and 287.9 $(M)^+$ (calculated for $C_{12}H_{16}BrClN$ 288.6). $^1H$ NMR data (DMSO-d6): δ 7.66 (d, 1H, J=1.9 Hz, Ar—H); 7.52 (dd, 1H, $J_1$=1.9 Hz, $J_2$=8.0 Hz, Ar—H), 7.43 (d, 1H, J=8.1 Hz, Ar—H), 3.91 (d, 1H, J=14.4 Hz), 2.28 (d, 2H, J=8.5 Hz); 2.78-2.85 (m, 1H); 2.42-2.49 (m, 1H); 2.11 (dd, 1H, $J_1$=8.8 Hz, $J_2$=17.6 Hz); 1.87-1.97 (m, 1H); 1.57-1.67 (m, 2H); 1.27-1.39 (m, 1H); 1.08 (d, 3H, J=5.9 Hz).

Intermediate 5

Pyrrolidine Hydrochloride

4N HCl/dioxane (70.5 mL) was added to a solution of pyrrolidine (20 g, 0.28 mol) in dioxane (20 ml). The reaction mixture was evaporated. The residue was recrystallized from $Et_2O$, separated by filtration, washed with ether, and dried to give the title compound (28.5 g, 96%) as white crystals. $^1H$ NMR data (DMSO-d6): δ 9.40 (br.s, 2H, NH'); 3.00-3.13 (m, 4H); 1.77-1.85 (m, 4H).

Example 4

1-(3-Chloro-4-{[(2R)-2-methylpyrrolidin-1-yl]methyl}phenyl)-3-(pyrrolidin-1-ylcarbonyl)cyclobutanol A 2.7 M solution of n-BuLi in heptane (3.6 mL, 9.6 mmol) was added for 5 min to a solution of intermediate 4, (2R)-1-

(4-bromo-2-chlorobenzyl)-2-methylpyrrolidine. (2.52 g, 8.8 mmol) in absolute THF (20 ml) in a flow of argon at −78 to −80° C. The reaction mixture was stirred at −78 to −80° C. for 15 min. Then a solution of 3-oxocyclobutanecarboxylic acid (500 mg, 4.4 mmol) in absolute THF (4 mL) was added drop wise over 5 min at −80° C. The mixture was warmed to 0° C. for 1 h and evaporated to dryness. The residue was dissolved in DMF (10 mL), Intermediate 5, pyrrolidine HCl (520 mg, 4.8 mmol) was added. Then BOP (2.2 g, 4.8 mmol) was added in portions under cooling in an ice bath for 16 h at room temperature. The disappearance of the starting hydroxy acid was monitored by LC/MS. The reaction mass was evaporated to dryness under 1 mmHg. Water (100 mL), EtOAc (50 mL), and a saturated solution of $K_2CO_3$ (to pH 10) were added. The layers were separated, and the aqueous one was subjected to extraction with EtOAc (2×50 mL). The combined organic layer was washed with water (50 mL), brine, dried with $Na_2SO_4$, and evaporated. The residue was purified by chromatography (60 mL of silica gel 63/100 μm, hexane/$CHCl_3$ 20:80→0:100, then $CHCl_3$/MeOH 100:0→90:10). The product-containing fraction were collected and concentrated to give the title compound (1.03 g, 63%). LC/MS data: 377.2 and 379.2 (M)$^+$ (calculated for $C_{21}H_{29}ClN_2O_2$ 376.93). $^1$H NMR data (DMSO-d6): δ 7.51 (s, 1H, Ar—H); 7.42-7.49 (m, 2H, Ar—H), 5.75 (s, 1H, OH); 3.96 (d, 1H, J=13.7 Hz), 3.25-3.35 (m, ?H+$H_2O$); 2.78-2.90 (m, 2H); 2.53-2.60 (m, 2H); 2.43-2.52 (m, ?H+DMSO); 2.06-2.16 (m, 1H); 1.88-1.97 (m, 1H); 1.80-1.87 (m, 2H); 1.72-1.79 (m, 2H); 1.57-1.67 (m, 2H); 1.29-1.40 (m, 1H); 1.11 (d, 3H, J=5.8 Hz, $CH_3$).

Intermediate 6

(2R)-1-{2-chloro-4-[3-(pyrrolidin-1-ylcarbonyl)cy-clobut-1-en-1-yl]benzyl}-2-methylpyrrolidine, trifluoroacetate A solution of Example 4,1-(3-Chloro-4-{[(2R)-2-meth-ylpyrrolidin-1-yl]methyl}phenyl)-3-(pyrrolidin-1-ylcarbo-nyl)cyclobutanol (400 mg, 1.06 mmol) and TFA (1.64 ml, 21.2 mmol) in 4 ml of DCE was refluxed under argon for 6 h, then additional amount of TFA (1.64 ml, 21.2 mmol) was added and the mixture was refluxed for 24 h. The mixture was evaporated to dryness. According to LCMS data the reaction mixture contained up to 80% of the title compound (359, 360, 361 (M+H) (calculated for $C_{21}H_{27}ClN_2O$ 358.92)). The resulting mixture was used for the next step without additional purification.

Example 5

(2R)-1-{2-Chloro-4-[trans-3-(pyrrolidin-1-ylcarbo-nyl)cyclobutyl]benzyl}-2-methylpyrrolidine hydrochloride To a solution of Intermediate 6, (2R)-1-{2-chloro-4-[3-(pyrrolidin-1-ylcarbonyl)cyclobut-1-en-1-yl]benzyl}-2-me-thylpyrrolidine, trifluoroacetate (1.06 mmol) in 5 mL of ethanol was added chlorotris(triphenylphosphine)rhodium(I) (100 mg, 0.106 mmol). The mixture was hydrogenated (40 psi $H_2$, at 50° C.) for 3 h. The reaction was monitored by LCMS. The mixture was evaporated to dryness, then 5 ml of 1N HCl was added to the residue and the solution was extracted with ethyl acetate (2×5 ml), the organic layers were discarded. 10N NaOH (1 mL) was added to the water layer and the water solution was extracted with ethyl acetate (3×5 mL). The organic layers were dried and evaporated in vacuo. The residue was purified by chromatography ($SiO_2$ 63/100 μm, 10 g, $CHCl_3$/hexane 80:20→100:0, $CHCl_3$/MeOH 100:0→90:10). The product containing fractions were collected and concentrated under reduced pressure. The residue was dissolved in 2 ml of ether and 0.1 mL of 4N HCl/dioxane was added under stirring. The solvent was evaporated; the residue was dried in vacuum to afford the HCl salt of the title compound (80 mg, 20%) as a dark yellow amorphous solid. LCMS data: 361 and 363 (M+H)$^+$ (calculated for $C_{21}H_{29}ClN_2O$ 360.93). $^1$H NMR data (CD$_3$OD): δ 7.63 (d, 1H, J=7.5 Hz), 7.50 (s, 1H), 7.39 (d, 1H, J=7.5 Hz), 4.75 (d, 1H, J=13.3 Hz), 4.31 (d, 1H, J=13.3 Hz), 3.63-3.77 (m, 2H), 3.34-3.52 (m, 7H), 2.64-2.75 (m, 2H), 2.33-2.49 (m, 3H), 1.72-2.20 (m, 7H), 1.51 (d, 3H, J=6.3 Hz).

Example 6

(2R)-1-{2-Chloro-4-[cis-1-fluoro-3-(pyrrolidin-1-ylcarbonyl)cyclobutyl]benzyl}-2-methylpyrrolidine HCl A solution of Example 4,1-(3-Chloro-4-{[(2R)-2-meth-ylpyrrolidin-1-yl]methyl}phenyl)-3-(pyrrolidin-1-ylcarbo-nyl)cyclobutanol (250 mg, 0.66 mmol) in 2 ml $CH_2Cl_2$ was added over 5 min to a solution of Deoxo-fluor (282 mg, 1.27 mmol) in $CH_2Cl_2$ (1 ml) in a flow of argon at −78 to −80° C. The reaction mixture was stirred at −78 to −80° C. for 1 h. The mixture was allowed to warm to 0° C. After 2 h, water (50 mL) was added followed by addition of 10 N NaOH, pH~10. The layers were separated, and the aqueous one was subjected to extraction with $CH_2Cl_2$ (2×30 mL). The combined organic layer was washed with brine, dried with $Na_2SO_4$, and evaporated. The residue was purified by chromatography (10 mL of silica gel 63/100 μm, hexane/$CH_2Cl_2$ 20:80→0:100, then $CH_2Cl_2$/i-PrOH 100:0→95:5). The product containing fractions were collected and concentrated. The residue was dissolved in ether (3 mL) and then 4N HCl/dioxane (0.125 mL) was added, evaporated and dried in vacuo to give the HCl salt of the title compound (158 mg, 57%) as a yellow oil. LC/MS data: 379.2 and 381.2 (M+H)$^+$ (calculated for O$_{21}$H$_{28}$ClFN$_2$O 378.92). $^1$H NMR data (DMSO-d6): δ 7.68-7.73 (m, 2H, Ar—H); 7.55-7.60 (m, 1H, Ar—H); 4.34 (d, 1H, J=13.4 Hz), 3.63-3.75 (m, 2H); 3.34-3.53 (m, 7H); 2.77-2.92 (m, 4H); 2.36-2.46 (m, 1H); 2.10-2.19 (m, 1H); 1.96-2.07 (m, 3H); 1.87-1.94 (m, 2H); 1.72-1.84 (m, 1H); 1.52 (d, 3H, J=6.3 Hz, $CH_3$).

Intermediate 7

3-(Morpholin-4-ylcarbonyl)cyclobutanone

CDI (8.1 g, 50 mmol) was added to a solution of 3-oxo-cyclobutanecarboxylic acid (5 g, 44 mmol) under vigorous stirring and cooling with an ice bath at 0° C. for 5 min. The reaction mixture was heated to 25° C., stirred at this temperature for 1 h, cooled to ° C., and morpholine (4.5 mL, 50 mmol) was added. The reaction mixture was heated to 25° C., stirred at this temperature for 3 h, and evaporated in vacuo. The residue was subjected to chromatography on $SiO_2$ (600 mL, 40-63 μm, $CCl_4$→$CHCl_3$→5% i-PrOH) to give compound 4 (6.5 g, 81%) as a colorless oil which solidifed in the refrigerator. LC MS—data: M$^+$ 184.1 and 185.1 (calculated for $C_{19}H_{13}NO_4$ 183.21). $^1$H-NMR (400 MHz)-data (dmso-d6): δ 3.54-3.60 (m, 4H), 3.43-3.52 (m, 5H), 3.16-3.32 (m, 4H).

Example 7

[3-Hydroxy-3-(4-pyrrolidin-1-ylmethyl-phenyl)-cyclobutyl]-morpholin-4-yl-methanone To a stirring solution of 1-(4-bromo-benzyl)-pyrrolidine (1.6 g, 6.5 mmol) in THF (20 mL) at −78° C. (acetone/dry ice bath) was added slowly down the side of the flask a solution of nBuLi (2.6 mL, 6.5 mmol, 2.5 M THF). After 15 minutes a solution of Intermediate 7, 3-(morpholin-4-ylcarbonyl)cyclobutanone (1.0 g, 5.4 mmol, in 7 mL of THF) precooled to −78° C. was added slowly. After 30 minutes the reaction was quenched cold with 1N HCl (20 mL). This mixture was diluted with EtOAc and then the layers were separated and the organic layer was discarded. The aqueous layer was basified with 1N NaOH and extracted with $CHCl_3$/iPrOH (3:1). The organic layer was dried over $MgSO_4$, filtered and concentrated to give a yellow oil. This material was purified by flash column chromatography using a 40 g ISCO™ column, eluting with a gradient of 3%, 5%, 10%, 20%, 30%/0 MeOH/ $CHCl_3$ with 0.1% $NH_4OH$. The product containing fraction were collected and concentrated under reduced pressure to give the title compound (379 mg, 20% yield): $R_f$=0.3 (30% MeOH/$CH_2Cl_2$); LRMS m/z Calcd for $C_{20}H_{28}N_2O_3$, 344.4, found, 345 (M+1) APCI; 400 MHz $^1$H NMR ($CDCl_3$) δ 7.42 (d, J=8.3 Hz, 2H), 7.29 (d, J=8.3 Hz, 2H), 4.58 (brs, 1H), 3.62-3.55 (m, 8H), 3.34-3.32 (m, 2H), 2.87 (dddd, J=8.3, 8.3, 8.3, 8.3 Hz, 1H), 2.77-2.71 (m, 2H), 2.64-2.59 (m, 2H), 2.48-2.45 (m, 4H), 1.75-1.70 (m, 4H); 100 MHz $^{13}$C NMR ($CDCl_3$) δ 173.8, 144.4, 137.8, 129.3, 125.3, 72.9, 67.0, 66.9, 60.3, 54.2, 46.0, 42.6, 40.9, 28.1, 23.5.

Intermediate 8

1-(4-bromo-2-fluorobenzyl)pyrrolidine

A 4-L RB flask, equipped a magnetic stirring bar was charged with pyrrolidine (363 g, 426 mL, 5.1 mol) and acetonitrile (2750 mL). The mixture was cooled with an ice bath to 10° C., then solid 4-bromo-2-fluorobenzylbromide (MATRIX, Cat. #: 1707, 375 g, 1.4 mol) was added in 6 portions, keeping temperature below 20° C. The mixture was stirred at RT for 4 h. The solvent was removed under vacuum. Then 2 L of sat. $Na_2CO_3$ aq. and 500 mL of water was added, and the mixture was extracted with DCM (3×700 mL). The extract was dried over $Na_2SO_4$ and evaporated. The resulting light yellow oil was distilled under vacuum (~1 mm, bp. 125° C.) to give 324.5 g (90%) of the product as a colorless oil. LCMS (M+H): 258.5.

$^1$H NMR (300 MHz, $CDCl_3$): δ 7.19-7.31 (m, 3H), 3.63 (m, 2H), 2.53 (m, 4H), 1.78 (m, 4H).

Intermediate 9

3-[3-fluoro-4-(pyrrolidin-1-ylmethyl)phenyl]-3-hydroxycyclobutanecarboxylic acid A 2-L 3-neck RB flask, equipped a mechanical stirrer, addition funnel, thermometer and nitrogen gas inlet was charged with Intermediate 8,1-(4-bromo-2-fluorobenzyl) pyrrolidine (69.86 g, 0.27 mol) and 700 mL of anhydrous THF. The system was flushed with nitrogen and cooled to −85° C. with liquid nitrogen with an ether/MeOH (1:1) bath. Then n-BuLi (10M in hexane, 30 mL, 0.298 mol) was added dropwise through an addition funnel at T<−80° C. The mixture was stirred at this temperature for an additional 15 min, then a solution of 3-oxocyclobutanecarboxylic acid (dried under vacuum for 2 days, 15.4 g, 0.135 mol) in 300 mL of anhydrous THF was added dropwise through an addition funnel keeping T<−80° C. The mixture was allowed to warm to RT and evaporated. The residue was mixed with 500 mL of water and washed with ether (2×300 mL). Then the aqueous solution was acidified to pH 1 with conc. HCl and washed with ether (2×300 mL). Then the aqueous solution was neutralized to pH 6-5 with NaOH and coevaporated three times with iPrOH (300 mL each time). Then the mixture was coevaporated with THF (200 mL) and dried to give gummy residue containing the product with inorganic salts. LCMS (M+H): 294.4

This material was used directly for the next step.

Example 8

N-{2-fluoro-4-[1-hydroxy-3-(pyrrolidin-1-ylcarbonyl)cyclobutyl]benzyl}-pyrrolidine A 2-L 3-neck RB flask, equipped a mechanical stirrer, addition funnel and nitrogen gas inlet was charged with Intermediate 9, 3-[3-fluoro-4-(pyrrolidin-1-ylmethyl)phenyl]-3-hydroxycyclobutanecarboxylic acid (0.135 mol, crude material from the above intermediate), 500 mL of anhydrous THF and DIEA (34.8 g, 0.27 mol). The initially insoluble mixture was stirred for 1.5 h until a uniform suspension formed. Then 2,4,6-tripropyl-1,3,5,2,4,6-trioxatriphosphorinane-2,4,6-trioxide (50% solution in EtOAc, 104.5 mL, 0.164 mol) was added and stirred for 5 min. (NOTE: exotherm was observed, reached ~45-50° C.). Then pyrrolidine (28.2 mL, 24.0 g, 0.337 mol) was added. (NOTE: more exotherm was observed, reached ~70-80° C.). The mixture was stirring at RT for 12 h, then evaporated. The residue was mixed with 500 mL of sat. $Na_2CO_3$ and 200 mL of water. The mixture was extracted with DCM (5×300 mL), the extract was dried over $Na_2SO_4$, evaporated and dried to give 33.4 g (71% for two steps) of pure title compound (LCMS (M+H): 347.1. $^1$H NMR (300 MHz, $CDCl_3$): δ 7.37 (t, J=7.37 Hz, 1H), 7.17-7.26 (m, 2H), 3.68 (s, 2H), 3.53 (t, J=6.78 Hz, 2H), 3.44 (t, J=6.58 Hz, 2H), 3.03-3.14 (m, 1H), 2.79-2.87 (m, 2H), 2.5-2.6 (m, 6H), 1.87-2.00 (m, 4H), 1.75-1.80 (m, 4H).

Example 9

N-{2-fluoro-4-[1-fluoro-3-(pyrrolidin-1-ylcarbonyl)cyclobutyl]benzyl}-pyrrolidine hydrochloride A 2-L 3-neck RB flask, equipped a magnetic stirring bar, thermometer, addition funnel and nitrogen gas inlet was charged with Example 8, N-{2-fluoro-4-[1-hydroxy-3-(pyrrolidin-1-ylcarbonyl)cyclobutyl]benzyl}-pyrrolidine (43.0 g, 0.124 mol) and 1 L of anhydrous DCM under nitrogen. The mixture was cooled to −75° C. with a dry ice/acetone bath, then Deoxo-Fluor (Aldrich, 33.0 g, 27.5 mL, 0.149 mol) was added dropwise. The mixture was warmed to 0° C. and stirred for 30 min at this temperature. Then the mixture was quenched with 350 mL of sat. $Na_2CO_3$, and extracted with DCM (3×300 mL). The extract was dried over $Na_2SO_4$ and evaporated. The resulting crude oil was purified by column (silica gel, ether 60%, hexane 30%, MeOH 5%, $Et_3N$ 5%, Rf=0.37 in ether 60%, hexane 30%, MeOH 5%, $NH_4OH$ 5%) to give 29.0 g (67%) of the title compound. $^1$H NMR (300 MHz, $CDCl_3$): δ 7.39 (t, J=7.64 Hz, 1H), 7.21 (d, J=7.92 Hz, 1H), 7.14 (d, J=10.9 Hz, 1H), 3.67 (s, 2H), 3.40-3.61 (m, 5H), 2.66-3.00 (m, 4H), 2.50-2.55 (m, 4H), 1.80-2.00 (m, 4H), 1.75-1.80 (m, 4H).

The free base of the product (29.0 g) was dissolved in 500 mL of ether, then 83 mL of 2M HCl/ether was added dropwise, stirred for 30 min, filtered and dried under vacuum to give 32.5 g of hydrochloride salt (NMR: contains approximately 4.5% of cis isomer). Then this material was dissolved in 200 mL of water, basified with NaOH to pH 10, extracted with DCM (3×300 mL) evaporated and purified by column again to give 25.0 g of free base product (NMR: contains approximately 3.5% of cis isomer). Then this 25 g of free base was converted to HCl salt as above. The HCl salt was recrystallized by dissolving in 250 mL of EtOAc/50 mL MeOH at 60° C., cooling down to RT, and stirring for 2 h. The precipitate was collected by filtration and dried to give 8.0 g of first crop (NMR: contains approximately 3% of cis isomer). The remaining mother liquor was concentrated under vacuum to 100 mL, then 100 mL of EtOAc was added and stirred for 30 min. The precipitate was filtered, combined with the first crop and dried under vacuum for 2 days to give 18.86 g of HCl salt (NMR:—contains approximately 3% of cis isomer). (LCMS (M+H): 349.5. $^1$H NMR (300 MHz, CDCl$_3$): δ 12.66 (br. s, 1H), 7.97 (t, J=7.81 Hz, 1H), 7.41 (d, J=8.1 Hz, 1H), 7.32 (d, J=10.9 Hz, 1H), 4.29 (d, J=5.25 Hz, 2H), 3.55-3.70 (m, 3H), 3.45-3.55 (m, 4H), 2.70-3.05 (m, 6H), 2.20-2.30 (m, 2H), 2.03-2.13 (m, 2H), 1.90-2.00 (m, 4H).

Intermediate 10

1-(4-Bromo-2-chloro-5-fluorobenzoyl)pyrrolidine

To a stirring solution of 4-bromo-2-chloro-5-fluorobenzoic acid (50 g, 0.25 mol) in 200 mL of EtOAc at 0° C. (ice/water bath) was added triethyl amine (237 mL, 0.50 mol), pyrrolidine (41.2 mL, 0.5 mol), followed by 2,4,6-tripropyl-1,3,5,2,4,6-trioxatriphosphorinane-2,4,6-trioxide (CAS #68957-94-8) (237 mL, 0.37 mol, 50 wt %, EtOAc). After 1 hr, the reaction was quenched with a saturated solution of NaHCO$_3$, and extracted with EtOAc, and CH$_2$Cl$_2$. The combined organic layers were dried over MgSO$_4$, filtered and concentrated. Purification of this material was accomplished by flash column chromatography using a Biotage™ 75 L column, eluting with a gradient of 2%-50% EtOAc/hexanes. The product containing fractions were collected and concentrated to give the title compound (52 g, 68% yield) as a white solid: R$_f$=0.23 (40% EtOAc/hexanes); LRMS m/z Calcd for C$_{11}$H$_{10}$BrClFNO, 306.6, found, 306, 308, 310 (M+1) APCI; $^1$H NMR (300 MHz, CDCl$_3$): δ 7.53 (d, J=6.2 Hz, 1H), 7.02 (d, J=7.9 Hz, 1H), 3.54 (apt t, J=6.6 Hz, 2H), 3.13 (apt t, J=6.6 Hz, 2H), 1.92-1.83 (m, 4H); 100 MHz $^{13}$C NMR (CDCl$_3$) δ 164.5, 158.1 (d, J$_{C-F}$=249.5 Hz), 138.2, 134.3, 126.0, 115.5 (d, J$_{C-F}$=25.5 Hz), 110.3 (d, J$_{C-F}$=22.5 Hz), 47.0, 45.8, 26.0, 24.6.

Intermediate 11

1-(4-Bromo-2-chloro-5-fluorobenzyl)pyrrolidine

To Intermediate 10, 1-(4-bromo-2-chloro-5-fluorobenzoyl)pyrrolidine (48.0 g, 156.5 mmol) in THF (200 mL) at rt was slowly added a solution of BH$_3$·THF complex (400 mL, 400 mmol, 1M THF). The resulting reaction was heated to 65° C. (oil bath) for 16 hr, and then the reaction was cooled to rt and slowly quenched with MeOH (dropwise addition). The reaction mixture was heated to reflux for 2 hr, cooled to rt, and concentrated under reduced pressure. This material was taken up in EtOAc and further quenched slowly with 6N HCl, then neutralized with aqueous NaOH (15%). The layers were separated and the aqueous layer was back extracted with EtOAc. The combined organic layers were dried over MgSO$_4$, filtered and concentrated under reduced pressure. Purification of this material was accomplished by flash column chromatography using a Biotage™ 75 L column, eluting with a gradient of 5%, 10% MeOH/CH$_2$Cl$_2$. The product containing fractions were collected and concentrated to give the title compound (43 g, 94% yield) as a light yellow oil: R$_f$=0.6 (10% MeOH/CH$_2$Cl$_2$); LRMS m/z Calcd for C$_{11}$H$_{12}$BrClFN, 292.6, found, 292 294, 296 (M+1) APCI; $^1$H NMR (300 MHz, CDCl$_3$): δ 7.51 (d, J=6.6 Hz, 1H), 7.33 (d, J=9.5 Hz, 1H), 3.66 (s, 2H), 2.59-2.55 (m, 4H), 1.82-1.79 (m, 4H); 100 MHz $^{13}$C NMR (CDCl$_3$) δ 158.3 (d, J$_{C-F}$=247.2 Hz), 139.3, 133.3, 128.9, 117.8 (d, J$_{C-F}$=24.9 Hz), 107.3 (d, J$_{C-F}$=22.6 Hz), 56.7, 54.4, 23.9.

Example 10

3-(5-Chloro-2-fluoro-4-pyrrolidin-1-ylmethyl-phenyl)-3-hydroxy-cyclobutanecarboxylic acid isobutylamide To Intermediate 11, 1-(4-Bromo-2-chloro-5-fluorobenzyl) pyrrolidine (4.0 g, 13.7 mmol) in THF (34 mL) at −78° C. (acetone/dry ice bath) was added a solution of nBuLi (5.5 mL, 13.7 mmol, 2.5 M THF). After 15 min, a precooled (−78° C.) solution of 3-oxocyclobutanecarboxylic acid (0.78 g, 6.8 mmol, in 5 mL of THF) was added via cannula. The reaction was allowed to slowly warm to rt overnight. After approximately 16 h, isobutylamine (1.4 mL, 13.7 mmol) was added, followed by 2,4,6-tripropyl-1,3,5,2,4,6-trioxatriphosphorinane-2,4,6-trioxide (50% solution in EtOAc, 6.6 mL, 10.2 mmol). After 1 hr the reaction was diluted with EtOAc and then quenched with 1N NaOH. The layers were separated and the aqueous layer was back extracted with EtOAc. The combined organic layers were dried over MgSO$_4$, filtered and concentrated under reduced pressure. Purification of this material was accomplished by flash column chromatography using a 120 g ISCO™ column, eluting with 5% MeOH/CH$_2$Cl$_2$ with 0.1% NH$_4$OH. The product containing fractions were collected and concentrated to give the title compound (400 mg, 15% yield) as a yellow foam: R$_f$=0.23 (10% MeOH/CH$_2$Cl$_2$); LRMS m/z Calcd for C$_{20}$H$_{28}$Cl FN$_2$O$_2$, 382.9, found, 383, 385 (M+H) APCI; $^1$H NMR (300 MHz, CDCl$_3$): δ 7.37 (d, J=7.0 Hz, 1H), 7.20 (d, J=11.6 Hz, 1H), 6.25-6.22 (bm, 2H), 3.68 (s, 2H), 3.09-2.84 (m, 5H), 2.57 (apt bs, 4H), 2.46-2.43 (m, 2H), 1.79-1.70 (m, 5H); 0.88 (d, J=6.6 Hz, 6H); 100 MHz $^{13}$C NMR (CDCl$_3$) δ 177.5, 159.5 (d, J$_{C-F}$=247.2), 138.3, 132.1, 128.2, 117.9 (d, J$_{C-F}$=24.7 Hz), 73.2, 56.5, 54.3, 47.4, 40.1, 34.6, 28.7, 23.8, 20.3.

Example 11

3-(5-Chloro-2-fluoro-4-pyrrolidin-1-ylmethyl-phenyl)-3-fluoro-cyclobutanecarboxylic acid isobutylamide To 3 mL of CH$_2$Cl$_2$ at −78° C. (acetone/dry ice bath) was added BAST (251 uL, 1.4 mmol), followed by a solution of Example 10, 3-(5-chloro-2-fluoro-4-pyrrolidin-1-ylmethylphenyl)-3-hydroxy-cyclobutanecarboxylic acid isobutylamide (350 mg, 0.91 mmol in 2 mL of CH$_2$Cl$_2$). After 1 hr the reaction was quenched with a saturated solution of sodium bicarbonate and then diluted with EtOAc. The layers were separated and the aqueous layer was back extracted with EtOAc. The combined organic layers were dried over MgSO$_4$, filtered and concentrated under reduced pressure. Purification of this material was accomplished by flash chromatography using a 40 g ISCO™ column, eluting with 5% MeOH/CH$_2$Cl$_2$. The product containing fractions were collected and concentrated to give the title compound as a mixture of isomers (223 mg, 63% yield) as a yellow oil: R$_f$=0.45 (10% MeOH/CH$_2$Cl$_2$); The mono HCl salt was made by dissolving the title compound in EtOAc and adding a 2N HCl ether solution (1.2 eq). The resulting solid was stirred 2 hr and then filtered and dried under reduced pressure to give the HCl salt of the title compound as a yellow solid: LRMS m/z Calcd for $C_{20}H_{27}ClF_2N_2O$, 384.9, found, 386, 388 (M+H) APCI: $^1$H NMR mixture of isomers, diagnostic peaks major isomer (300 MHz, CD$_3$OD): δ 7.62 (dd, J=7.0, 1.6 Hz, 1H), 7.54 (d, J=11.2 Hz, 1H), 4.47 (s, 2H), 3.59-3.47 (m, 2H), 3.43 (apt pent, J=7.3 Hz, 1H), 3.31-3.02 (m) under MeOH, 3.01-2.77 (m, 6H), 2.24-2.20 (m, 2H), 2.06-2.00 (m, 2H), 1.78-1.71 (m, 1H), 0.89 (d, J=7.0 Hz, 6H).

Example 12

3-(3-fluoro-4-pyrrolidin-1-ylmethyl-phenyl)-3-hydroxy-cyclobutanecarboxylic acid ethylamide n-Butyllithium (2.5M/hexanes, 251 mL, 0.628 mol) was added dropwise over 30 min to a −78° C. solution of 1-(4-bromo-2-fluorobenzyl)pyrrolidine (162.0 g, 0.63 mol) in THF (1.8 L). After stirring at −78° C. for 2 h, a −78° C. solution of 3-oxocyclobutanecarboxylic acid (35.8 g, 0.31 mol) in THF (400 mL) was cannulated over 25 min. into the reaction mixture. The resulting dark orange solution was slowly warmed to room temperature over 16 h. LC/MS of the mixture showed the intermediate acid 294.2 (M+H). Ethylamine (2M in THF, 315 mL, 0.630 mol) and T3P (50% wt in EtOAc, 224 mL, 0.376 mol) were added with 200 mL of rinse THF. After stirring for 1 h at room temperature, sat. NaHCO$_3$ (1000 mL) was added followed by water (~500 mL). The phases were separated and the aqueous phase was extracted with EtOAc (2×500 mL). The combined organics were washed with brine and dried over MgSO$_4$. Concentration yielded 161.8 g of orange oil that was split into 2 portions and purified by SiO$_2$ flash chromatography (4"×5.5" columns packed with EtOAc). Each column was flushed with 3 L EtOAc to remove higher Rf material and then the bulk of the desired product was obtained by elution with 3 L 25% MeOH/ EtOAc. Concentration of the product containing fractions from both columns afforded 48.8 g (49% yield) of 3-(3-fluoro-4-pyrrolidin-1-ylmethyl-phenyl)-3-hydroxy-cyclobutanecarboxylic acid ethylamide as a thick light orange oil which slowly crystallized to a waxy solid upon evacuation: $^1$HNMR (CDCl$_3$) δ 7.35 (t, J=7.9 Hz, 1H), 7.20-7.14 (m, 2H), 5.67 (br s, 1H), 5.57 (br s, 1H), 3.66 (d, J=1.3 Hz, 2H) 3.37-3.30 (m 2H), 2.84-2.70 (m, 3H), 2.53-2.44 (m, 6H), 1.83-1.70 (m overlapping water, 4H), 1.16 (t, J=7.3 Hz, 3H); LRMS m/z Calcd for $C_{18}H_{25}FN_2O_2$, 320.4, found, 321.3 (M+H) APCI.

Example 13

3-(3-Fluoro-4-pyrrolidin-1-ylmethyl-phenyl)-cyclobutanecarboxylic acid ethylamide To Example 12, 3-(3-Fluoro-4-pyrrolidin-1-ylmethyl-phenyl)-3-hydroxy-cyclobutanecarboxylic acid ethylamide (17 g, 53.1 mmol) in 200 mL of DCE at rt was added TFA (80.7 mL, 1.1 mol) and then the reaction was heated to 80° C. (oil bath). After 15 h the reaction was concentrated to approximately 45 g and used without further purification. The crude TFA salt from the above reaction was diluted with EtOH (500 mL), placed in a Parr bottle, purged with N$_2$, and then 10% Pd/carbon (2.5 g, 14 wt %) was added. The resulting reaction mixture was hydrogenated with H$_2$ (45 psi) at rt. After 1.5 h the reaction was purged with N$_2$, then filtered through Celite™ and concentrated under reduced pressure. The resulting oil was diluted with EtOAc and then slowly quenched with a saturated solution of sodium bicarbonate. The layers were separated and the aqueous layer was back extracted with EtOAc. The combined organic layers were dried over MgSO$_4$, filtered and concentrated under reduced pressure. Purification of this material was accomplished by re-crystallization. Crude title compound was taken up in a minimal amount of warm EtOAc and allowed to cool to approximately 0° C. (refrigerator). The solid was filtered, dried under reduced pressure to give the title compound (4 g, 24% yield) as a white solid: R$_f$=0.21 (10% MeOH/CH$_2$Cl$_2$); LRMS m/z Calcd for $C_{18}H_{25}FN_2O$, 304.4, found, 305.3; $^1$H NMR (300 MHz, CDCl$_3$): δ 7.30 (apt t, J=7.9 Hz, 1H), 6.98 (dd, J=7.9, 1.6 Hz, 1H), 6.92 (dd, J=12.0, 1.6 Hz, 1H), 5.36 (bs, 1H), 3.67 (s, 2H), 3.42-3.26 (m, 3H), 2.94-2.85 (m, 1H), 2.57-2.50 (m, 6H), 2.42-2.33 (m, 2H), 1.82-1.74 (m, 4H), 1.14 (t, J=7.5 Hz, 3H); structure confirmed by x-ray crystallography and was determined to be cis.

Example 14

3-(3-Fluoro-4-pyrrolidin-1-ylmethyl-phenyl)-3-hydroxy-cyclobutanecarboxylic acid ethyl-methyl-amide n-Butyllithium (2.5M/hexanes, 140 mL, 0.350 mol) was added down the reaction flask walls over 25 min to a −78° C. solution of Intermediate 8,1-(4-bromo-2-fluorobenzyl)pyrrolidine (90.0 g, 0.349 mol) in THF (1 L). After stirring at −78° C. for 2.5 h, a −78° C. solution of 3-oxocyclobutanecarboxylic acid (19.9 g, 174.5 mmol) in THF (200 mL) was cannulated over 15 min. into the reaction mixture. The resulting dark orange solution was slowly warmed to room temperature over 16 h. LC/MS of the mixture showed the intermediate acid 294.2 (M+H). Ethylmethylamine (30 mL, 0.349 mol) and T3P (50% wt in EtOAc, 125 mL, 0.210 mol) were added with 200 mL of rinse THF. After stirring for 1.5 h at room temperature, sat. NaHCO$_3$ (500 mL) was added followed by water (500 mL). The phases were separated and the aqueous phase was extracted with EtOAc (700 mL). The combined organics were washed with brine and dried over MgSO$_4$. Concentration yielded 89.0 g of orange oil that was purified by SiO$_2$ flash chromatography (4"×7" column packed with EtOAc). The column was flushed with 4 L EtOAc to remove higher Rf material and then the bulk of the desired product was obtained by elution with 4 L 25% MeOH/ EtOAc. Concentration of the product containing fractions afforded 35.15 g (60%) of the title compound, 3-(3-fluoro-4-pyrrolidin-1-ylmethyl-phenyl)-3-hydroxy-cyclobutanecarboxylic acid ethyl-methyl-amide as a thick light orange oil which slowly crystallized to a waxy solid upon evacuation: NMR (CDCl$_3$) ~1:1 mixture of rotamers, δ 7.35 (t, J=7.7 Hz, 1H), 7.23-7.15 (m, 2H), 5.08 and 4.84 (broad singlet, 1H total), 3.65 (s, 2H), 3.45 and 3.30 (quartets, J=7.2 Hz, 2H total), 3.21-3.10 (m, 1H), 2.97 and 2.95 (singlet, 3H total), 2.84-2.77 (m, 2H), 2.57-2.52 (m, 6H), 1.79-1.72 (m, 4H), 1.18-1.04 (m, 3H).

Intermediate 12

N-ethyl-3-(3-fluoro-4-(pyrrolidin-1-ylmethyl)phenyl)-N-methylcyclobut-2-enecarboxamide trifluoroacetate salt 3-(3-Fluoro-4-pyrrolidin-1-ylmethyl-phenyl)-3-hydroxy-cyclobutanecarboxylic acid ethyl-methyl-amide (Example 14, 35.15 g, 105.1 mmol) was dissolved in a mixture of 1,2-dichloroethane (1 L) and trifluoroacetic acid (150 mL) and refluxed for 16 h. The resulting dark brown solution was cooled and concentrated to yield a brown oil (94.46) of crude title compound, N-ethyl-3-(3-fluoro-4-(pyrrolidin-1-ylmethyl)phenyl)-N-methylcyclobut-2-enecarboxamide trifluoroacetate salt, with residual TFA, which was used in the next step without purification.

Example 15

3-(3-Fluoro-4-pyrrolidin-1-ylmethyl-phenyl)-cyclobutanecarboxylic acid ethyl-methyl-amide A hydrogenation vessel was rinsed with ethanol, purged with nitrogen and charged with 50 mL ethanol, 10% palladium on carbon (10 g) and a solution of crude Intermediate 12, N-ethyl-3-(3-fluoro-4-(pyrrolidin-1-ylmethyl)phenyl)-N-methylcyclobut-2-enecarboxamide trifluoroacetate salt (182.0 g) in ethanol (1.5 L). This mixture was then shaken under hydrogen (~45 psi) at room temperature for 1.5 h, filtered through a 2" pad of diatomaceous earth and rinsed with ethanol (500 mL). The filtrate was concentrated to give an orange oil which was dissolved in EtOAc (500 mL) and washed with a solution of $K_2CO_3$ (60 g) in water (400 mL) and then brine (200 mL), dried over $MgSO_4$ and concentrated to afford 66.26 g of an orange oil. This material was purified by flash chromatography on a 4"×5.5" silica gel column ($CH_2Cl_2$ packed), flushing first with 2.5 L $CH_2Cl_2$ and then eluting with 3 L 5% MeOH/$CH_2Cl_2$. The clean product fractions were concentrated to afford 41.75 g (58%) of >95% pure title compound. Concentration of the less pure fractions yielded another 9.98 g of ~85-90% pure material: $R_f$=0.17 (20% MeOH/EtOAc); $^1H$ NMR ($CDCl_3$) ~1:1 mixture of rotamers, δ 7.28-7.24 (m partially obscured by $CHCl_3$, 1H), 6.98-6.94 (m, 1H), 6.92-6.88 (m, 1H), 3.62 (d, J=0.8 Hz, 2H), 3.42-3.14 (overlapping multiplets, 4H), 2.92 and 2.89 (singlets, 3H total), 2.58-2.35 (m, 8H), 1.80-1.70 (m, 4H), 1.14 and 1.08 (triplets, J=7.2 Hz, 3H total).

The cleaner material (41.75 g, 131.11 mmol) was dissolved in EtOAc (1 L) and 2N HCl/diethylether (80 mL, 160 mmol) was added over ~1 min with vigorous stirring. After 30 min, the light orange tinged precipitate was collected, rinsed with EtOAc and dried under nitrogen purge to yield the corresponding HCl salt (36.15 g). This material was combined with other lots (39.72 g total weight), and dissolved in a mixture of MeOH (30 mL) and EtOAc (50 mL) with gentle heating. Next, EtOAc (550 mL) was added dropwise over ~15 min to the stirring mixture. After stirring an additional 15 min at room temperature, the solids were filtered, rinsed with 200 mL EtOAc and dried under nitrogen to yield 32.98 g of the hydrochloride salt of the title compound as a white crystalline solid: mp 196-196.5° C.; $^1H$ NMR ($CDCl_3$) ~1:1 mixture of rotamers, δ 12.69 (br s, 1H), 7.79 (t, J=7.9 Hz, 1H), 7.07-7.00 (m, 2H), 4.20 (d, J=5.4 Hz, 2H), 3.64-3.57 (m, 2H), 3.47-3.53 (m, 2H), 3.30-3.16 (m, 2H), 2.91 and 2.88 (singlets, 3H total), 2.85-2.79 (m, 2H), 2.60-2.50 (m, 2H), 2.46-2.34 (m, 2H), 2.26-2.14 (m, 2H), 2.06-1.95 (m, 2H), 1.14 and 1.07 (triplets, J=7.1 Hz, 3H total); $^{13}C$ NMR ($CDCl_3$) δ (mixture of rotamers) 173.29, 162.70, 160.24, 150.57, 150.49, 133.62, 133.59, 123.99, 123.97, 114.44, 114.30, 113.98, 113.77, 52.62, 49.92, 49.90, 44.07, 42.65, 35.33, 34.25, 33.45, 32.77, 32.40, 23.21, 14.07, 12.44; LRMS m/z Calcd for $C_{19}H_{27}FN_2O$, 318.4, found, 319.4 (M+H) APCI; Anal. Calculated for $C_{19}H_{27}FN_2O\cdot HCl$: C, 64.30; H, 7.95; N, 7.89. Found C, 64.36; H, 8.02; N, 7.97.

Example 16

3-Fluoro-3-(3-fluoro-4-pyrrolidin-1-ylmethyl-phenyl)-cyclobutanecarboxylic acid ethylamide A solution of Example 12, 3-(3-fluoro-4-pyrrolidin-1-ylmethyl-phenyl)-3-hydroxy-cyclobutanecarboxylic acid ethylamide (48.7 g, 152.0 mmol) in $CH_2Cl_2$ (450 mL) was added over 50 min down the reaction flask walls to a −78° C. solution of bis(2-methoxyethyl)aminosulfur trifluoride (42.0 mL, 227.8 mmol) in $CH_2Cl_2$ (375 mL). After stirring for 2.5 h at −78° C., the cooling bath was removed and the mixture was stirred for 16 h at room temperature. With stirring, aq. $NaHCO_3$ was carefully added in portions until all foaming subsided. Solid $K_2CO_3$ was then added to ensure that the pH was >8. The phases were separated and the aqueous phase was extracted with two additional 100 mL portions of $CH_2Cl_2$. The organic phases were combined, dried over $MgSO_4$ and concentrated to yield a dark orange-brown oil (50.2 g). This crude material was concentrated onto 100 g silica gel and then purified by flash chromatography on a 4"×6" silica gel column packed with EtOAc. The column was eluted with 3 L each EtOAc and 10% MeOH/EtOAc. The cleanest fractions were concentrated to afford 20.82 g of the title compound as an orange tinged solid which GC/MS showed to be ~94% pure with ~6% of the corresponding trans isomer. Re-purification of this lot and the less pure fractions was achieved by either repeating the MeOH/EtOAc column chromatography or by chromatography on a ChiralcelOD column (10 cm×50 cm) using 93:7 heptane:isopropyl alcohol with a flow rate of 460 mL/min. These re-chromatographed materials were then triturated with 10% ethyl ether/hexanes (~8 mL/gram) to yield 28.21 g (58%) of 95+% pure title compound: $R_f$=0.23 (20% MeOH/EtOAc); $^1H$ NMR ($CDCl_3$) δ 7.38 (t, J=7.7 Hz, 1H), 7.20 (d, J=8.3 Hz, 1H), 7.13 (dd, J=10.8, 1.6 Hz, 1H), 5.43 (br s, 1H), 3.66 (s, 2H), 3.33-3.18 (m, 3H), 2.92-2.78 (m, 2H), 2.76-2.64 (m, 2H), 2.58-2.48 (m, 4H), 1.81-1.70 (m, 4H), 1.13 (t, J=7.3 Hz, 3H).

The hydrochloride salt of the title compound was prepared by addition of 53 mL 2N HCl/ethyl ether to a stirring solution of freebase in 650 mL EtOAc. After stirring for ~2 h, the white precipitate was collected, washed with EtOAc and dried under a stream of nitrogen: mp 196.5-197.5° C.; $^1H$ NMR (MeOH-$d_4$) δ 7.60 (t, J=7.7 Hz, 1H), 7.46-7.40 (m, 2H), 4.46 (s, 2H), 3.56-3.50 (m, 2H), 3.37 (p, J=8.5 Hz, 1H), 3.24-3.17 (m, 4H), 2.86-2.67 (m, 4H), 2.22-2.10 (m, 2H), 2.08-1.95 (m, 2H), 1.10 (t, J=7.3 Hz, 3H); $^{13}C$ NMR ($CDCl_3$) δ 173.6, 161.3 (d, $J_{C-F}$=248.0 Hz), 147.1 (dd, $J_{C-F}$=24.0, 7.7 Hz), 134.0 (d, $J_{C-F}$=2.3 Hz), 121.9 (dd, $J_{C-F}$=8.3, 2.7 Hz), 116.4 (d, $J_{C-F}$=13.2 Hz), 112.6 (dd, $J_{C-F}$=24.1, 8.8 Hz), 96.7 (d, $J_{C-F}$=197.3 Hz), 52.83, 49.9 (d, $J_{C-F}$=3.0 Hz), 38.8 (d, $J_{C-F}$=24.8 Hz), 34.8, 32.9, 23.3, 15.0; Anal. Calculated for $C_{18}H_{24}F_2N_2O\cdot HCl$: C, 60.25; H, 7.02; N, 7.81. Found C, 60.15; H, 7.32; N, 7.60.

Intermediate 13

1-(4-bromo-3,5-difluorobenzyl)pyrrolidine 3,5-Difluorobenzaldehyde (2.0 mL, 18.24 mmol), pyrrolidine (1.8 mL, 21.56 mmol), and sodium triacetoxyborohydride (5.8 g, 27.4 mmol) were stirred in THF (50 mL) for 16 h at room temperature. Saturated aqueous $NaHCO_3$ (30 mL) was added and after stirring for 30 min, EtOAc (50 mL) was added. The organic phase was separated and washed with brine, dried over $MgSO_4$ and concentrated to afford 2.65 g (74%) of 1-(3,5-difluorobenzyl)pyrrolidine as a slightly cloudy oil: $^1H$ NMR ($CDCl_3$) δ 6.88-6.83 (m, 1H), 6.68-6.63 (m, 2H), 3.59 (s, 2H), 2.53-2.48 (m, 4H), 1.80-1.77 (m, 4H).

Intermediate 14

3-(2,6-difluoro-4-(pyrrolidin-1-ylmethyl)phenyl)-3-hydroxy-N-methylcyclobutanecarboxamide 2,2,6,6-Tetramethylpiperidine (1.86 mL, 11.0 mmol) was added to a −78° C. solution of n-butyllithium (2.5 M in hexanes, 4.4 mL, 11.0 mmol) in hexanes (12 mL) and THF (25 mL). The resulting mixture was stirred for 10 min and then intermediate 13, 1-(3,5-difluorobenzyl)pyrrolidine (2.17 g, 11.0 mmol) in 3 mL THF was added down the flask walls over 1 min. After stirring for 2.5 h, a −78° C. solution of 3-oxocyclobutanecarboxylic acid (0.63 g, 5.5 mmol) in THF (10 mL) was cannulated into the reaction mixture. This mixture was allowed to slowly warm to room temperature and was stirred for 16 h. Methylamine (2.0M in THF, 5.5 mL, 11.0 mmol) and T3P (50% wt in EtOAc, 3.9 mL, 6.55 mmol) were then added. After 2 h stirring, saturated aqueous NaHCO$_3$ was added and the mixture was extracted into EtOAc, dried over MgSO$_4$ and concentrated to yield a tan oil. Silica gel flash chromatography using first 3% then 15% MeOH/CH$_2$Cl$_2$ afforded 99 mg (5.5%) of the title compound, 3-(2,6-difluoro-4-(pyrrolidin-1-ylmethyl)phenyl)-3-hydroxy-N-methylcyclobutanecarboxamide as a waxy white solid: R$_f$=0.036 (CH$_2$Cl$_2$); $^1$H NMR (CDCl$_3$) δ 6.84-6.78 (m, 2H), 6.25-6.20 (br m, 1H), 3.52 (s, 2H), 3.01-2.95 (m, 2H), 2.90-2.84 (m, 1H), 2.79 (d, J=5.0 Hz, 3H), 2.58-2.54 (m, 2H), 2.48-2.44 (m, 4H), 1.77-1.73 (m, 4H); $^{13}$C NMR (CDCl$_3$) δ 222.6, 178.5, 161.2 (d, J$_{C-F}$=240.5 Hz), 142.2, 111.9 (dd, J$_{C-F}$=25.6, 6.8 Hz), 73.0, 59.7, 54.2, 40.8, 37.0, 26.8, 23.7.

Example 17

3-(2,6-Difluoro-4-pyrrolidin-1-ylmethyl-phenyl)-3-fluoro-cyclobutanecarboxylic acid methylamide Bis(2-methoxyethyl)aminosulfur trifluoride (0.070 mL, 0.380 mmol) was added to a 0° C. solution of intermediate 14, 3-(2,6-difluoro-4-(pyrrolidin-1-ylmethyl)phenyl)-3-hydroxy-N-methylcyclobutanecarboxamide (0.099 g, 0.305 mmol) in CH$_2$Cl$_2$ (2 mL) and the resulting mixture was allowed to warm to room temperature and stir for 18 h. The reaction was poured into saturated aqueous NaHCO$_3$ and extracted with CH$_2$Cl$_2$ (2×15 mL), dried over MgSO$_4$ and concentrated to yield 92 mg of light yellow oil: R$_f$=0.21 (20% MeOH/EtOAc). Silica gel flash chromatography using EtOAc and then 5% and 10% MeOH/EtOAc for elution afforded 66 mg (67% yield) of the title compound: LRMS m/z Calcd for C$_{17}$H$_{21}$F$_3$N$_2$O, 326.4, found, 327.4 (M+H), 307.4 (M+H−HF) APCI; $^1$H NMR (CDCl$_3$) δ 6.87 (d, J=8.7 Hz, 2H), 5.42 (br s, 1H), 3.56 (m, 2H), 3.32 (p, J=8.5 Hz, 1H), 3.06-2.78 (m, 7H), 2.50 (br s, 4H), 1.79 (br s, 4H).

Intermediate 15

3-(3-fluoro-4-(pyrrolidin-1-ylmethyl)phenyl)-3-hydroxycyclobutanecarboxylic acid n-Butyllithium (2.5M/hexanes, 78 mL, 0.195 mol) was added down the reaction flask walls over 5 min to a −78° C. solution of 1-(4-bromo-2-fluorobenzyl)pyrrolidine (50.0 g, 0.194 mol) in THF (500 mL). After stirring at −78° C. for 1 h, a −78° C. solution of 3-oxocyclobutanecarboxylic acid (11.0 g, 96.4 mmol) in THF (150 mL) was cannulated over 10 min into the reaction mixture. The resulting dark orange solution was slowly warmed to room temperature over 16 h. LC/MS of the mixture showed the title compound 294.2 (M+H). This material was used as a crude solution without work-up, assuming ~0.12 M concentration of the title compound.

Example 18

3-(3-Fluoro-4-pyrrolidin-1-ylmethyl-phenyl)-3-hydroxy-cyclobutanecarboxylic acid methylamide A THF solution of ~0.12M intermediate 15, 3-(3-fluoro-4-(pyrrolidin-1-ylmethyl)phenyl)-3-hydroxycyclobutanecarboxylic acid (160 mL, 19.3 mmol) was combined with methylamine (2.0M in THF, 20 mL, 40 mmol) and T3P (50% wt in EtOAc, 13.8 mL, 23.2 mmol) and stirred at room temperature for 20 h. The mixture was made basic with saturated aqueous NaHCO$_3$ and EtOAc (50 mL) was added. The phases were separated and the aqueous phase was extracted again with EtOAc. The combined organics were washed with brine, dried over MgSO$_4$ and concentrated to yield an orange oil (8.6 g). Flash chromatography on a 2"×4" silica gel column flushing first with EtOAc (1 L) and 10% MeOH/EtOAc (500 mL) to remove higher Rf impurities followed by elution with an additional 500 mL of 10% MeOH/EtOAc and 500 mL 20% MeOH/EtOAc afforded 3.14 g (53%) of the title compound as a thick orange oil which slowly solidified to a waxy solid: R$_f$=0.30, 20% MeOH/EtOAc; $^1$H NMR (CDCl$_3$) δ 7.35 (t, J=7.7 Hz, 1H), 7.21-71.3 (m, 2H), 5.73 (br s, 1H), 3.66 (d, J$_{H-F}$=1.2 Hz, 2H), 2.86 (d, J=4.6 Hz, 3H), 2.85-2.73 (m, 3H), 2.55-2.45 (m, 6H), 1.79-1.60 (m overlapping water, 4H); $^{13}$C NMR (CDCl$_3$) δ 177.5, 161.3 (d, J$_{C-F}$=246.2 Hz), 147.3 (d, J$_{C-F}$=7.1 Hz), 131.6 (d, J$_{C-F}$=4.9 Hz), 124.2 (d, J$_{C-F}$=15.0 Hz), 120.6 (d, J$_{C-F}$=3.3 Hz), 112.3 (d, J$_{C-F}$=23.3 Hz), 74.0 (d, J$_{C-F}$=1.9 Hz), 54.04, 52.6 (d, J$_{C-F}$=1.5 Hz), 41.2, 32.9, 26.8, 23.6; LRMS m/z Calcd for C$_{17}$H$_{23}$FN$_2$O$_2$, 306.4, found, 307.4 (M+H) APCI.

Example 19

3-(3-Fluoro-4-pyrrolidin-1-ylmethyl-phenyl)-3-hydroxy-cyclobutanecarboxylic acid dimethylamide A THF solution of −0.12M intermediate 15, 3-(3-fluoro-4-(pyrrolidin-1-ylmethyl)phenyl)-3-hydroxycyclobutanecarboxylic acid (160 mL, 19.3 mmol) was combined with dimethylamine (2.0M in THF, 20 mL, 40 mmol) and T3P (50% wt in EtOAc, 13.8 mL, 23.2 mmol) and stirred at room temperature for 20 h. The mixture was made basic with saturated aqueous NaHCO$_3$ and EtOAc (50 mL) was added. The phases were separated and the aqueous phase was extracted again with EtOAc. The combined organics were washed with brine, dried over MgSO$_4$ and concentrated to yield an orange oil (8.6 g). Flash chromatography on a 2"×4" silica gel column flushing first with EtOAc (1 L) and 10% MeOH/EtOAc (500 mL) to remove higher Rf impurities followed by elution with an additional 500 mL of 10% MeOH/EtOAc and 500 mL 20% MeOH/EtOAc afforded 3.58 g (58%) of the title compound as a thick orange oil which slowly solidified to a waxy solid: R$_f$=0.17 (20% MeOH/EtOAc); $^1$H NMR (CDCl$_3$) δ 7.36 (t, J=7.9 Hz, 1H), 7.23-7.15 (m, 2H), 4.70 (br s, 1H), 3.66 (s, 2H), 3.21-3.12 (m, 1H), 3.00 (3, 3H), 2.99 (s, 3H), 2.84-2.78 (m, 2H), 2.57-2.43 (m, 6H), 1.80-1.74 (m overlapping water, 4H); $^{13}$C NMR (CDCl$_3$) δ 175.8, 161.3 (d, J$_{C-F}$=246.2 Hz), 147.4 (d, J$_{C-F}$=7.1 Hz), 131.6 (d, J$_{C-F}$=4.5 Hz), 124.3 (d, J$_{C-F}$=15 Hz), 120.7 (d, J$_{C-F}$=3.0 Hz), 112.4 (d, J$_{C-F}$=23.3 Hz), 73.3 (d, J$_{C-F}$=1.1 Hz), 54.03, 52.6 (d, J$_{C-F}$=1.1 Hz), 41.1, 37.4, 36.2, 28.5, 23.6; LRMS m/z Calcd for C$_{18}$H$_{25}$FN$_2$O$_2$, 320.4, found, 321.4 (M+H) APCI.

Example 20

3-(3-Fluoro-4-pyrrolidin-1-ylmethyl-phenyl)-3-hydroxy-cyclobutanecarboxylic acid isobutyl-amide A THF solution of crude ~0.12M intermediate 15, 3-(3-fluoro-4-(pyrrolidin-1-ylmethyl)phenyl)-3-hydroxycyclobutanecarboxylic acid (160 mL, 19.3 mmol) was combined with isobutylamine (3.8 mL, 38.2 mmol) and T3P (50% wt in EtOAc, 13.8 mL, 23.2 mmol) and stirred at room temperature for 20 h. The mixture was made basic with saturated aqueous NaHCO$_3$ and EtOAc (50 mL) was added. The phases were separated and the aqueous phase was extracted again with EtOAc. The combined organics were washed with brine, dried over MgSO$_4$ and concentrated to yield an orange oil. Flash chromatography on a 2"×4" silica gel column flushing first with EtOAc (1 L) and 10% MeOH/EtOAc (500 mL) to remove higher Rf impurities followed by elution with an additional 500 mL of 10% MeOH/EtOAc and 500 mL 20% MeOH/EtOAc afforded 4.22 g (63%) of the title compound as an waxy, orange solid: R$_f$=0.3 (30% MeOH/EtOAc); $^1$H NMR (CDCl$_3$) δ 7.34 (t, J=7.9 Hz, 1H), 7.20-7.13 (m, 2H), 5.84 (br s, 1H), 3.66 (d, J$_{H-F}$=1.3 Hz, 2H), 3.11 (t, J=6.4 Hz, 2H), 2.84-2.76 (m, 3H), 2.55-2.45 (m, 6H), 1.81-1.72 (m, 4H), 0.91-0.87 (d @ 0.90 (J=6.6 Hz, 6H) overlapping m (1H)); LRMS m/z Calcd for C$_{20}$H$_{29}$FN$_2$O$_2$, 348.5, found, 349.4 (M+H) APCI.

Example 21

3-Fluoro-3-(3-fluoro-4-pyrrolidin-1-ylmethyl-phenyl)-cyclobutanecarboxylic acid methylamide Bis(2-methoxyethyl)aminosulfur trifluoride (0.29 mL, 1.57 mmol) was added to a 0° C. solution of Example 18, 3-(3-fluoro-4-pyrrolidin-1-ylmethyl-phenyl)-3-hydroxy-cyclobutanecarboxylic acid methylamide (0.40 g, 1.31 mmol) in CH$_2$Cl$_2$ (8 mL). This mixture was slowly warmed to room temperature and stirred for 18 h and then poured into saturated aqueous NaHCO$_3$. The organic phase was separated, dried over MgSO$_4$ and concentrated to yield an orange oil (0.40 g). Flash chromatography on a 1.5"×2" silica gel column flushing first with 200 mL each EtOAc, 2% and 5% MeOH/EtOAc to remove higher Rf impurities followed by elution with 400 mL of 10% MeOH/EtOAc and 200 mL 20% MeOH/EtOAc afforded 0.244 g (61%) of the title compound as an orange oil: R$_f$=0.11 (20% MeOH/EtOAc).

The HCl salt of the title compound was prepared in EtOAc with 1.5 equivalent of 2N HCl/ethyl ether. The hygroscopic white solid was collected and dried under nitrogen: $^1$H NMR (MeOH-d$_4$) δ 7.60 (t, J=7.9 Hz, 1H), 7.45-7.40 (m, 2H), 4.46 (s, 2H), 3.60-3.45 (m, 2H), 3.37 (p, J=8.7 Hz, 1H), 3.24-3.14 (m, 2H), 2.87-2.67 (s @ 2.72 (3H) overlapping a multiplet (4H)), 2.22-2.10 (m, 2H), 2.02-1.97 (m, 2H); $^{13}$C NMR (MeOH-d$_4$) δ 175.6, 161.5 (d, J$_{C-F}$=248.8 Hz), 147.4 (dd, J$_{C-F}$=24.1, 7.1), 133.1 (d, J$_{C-F}$=2.6 Hz), 121.4 (d, J$_{C-F}$=4.9 Hz), 117.6 (d, J$_{C-F}$=15.8 Hz), 112.4 (dd, J$_{C-F}$=23.3, 8.9 Hz), 96.4 (d, J$_{C-F}$=195.4 Hz), 54.0, 51.0, 38.3 (d, J$_{C-F}$=25.2 Hz), 32.2, 25.3, 22.7; LRMS m/z Calcd for C$_{17}$H$_{22}$F$_2$N$_2$O, 308.4, found, 309.4 (M+H) APCI.

Example 22

3-Fluoro-3-(3-fluoro-4-pyrrolidin-1-ylmethyl-phenyl)-cyclobutanecarboxylic acid dimethylamide A solution of example 19, 3-(3-fluoro-4-pyrrolidin-1-ylmethyl-phenyl)-3-hydroxy-cyclobutanecarboxylic acid dimethylamide (0.40 g, 1.25 mmol) in CH$_2$Cl$_2$ (4 mL) was added to a −78° C. solution of bis(2-methoxyethyl)aminosulfur trifluoride (0.28 mL, 1.52 mmol) in CH$_2$Cl$_2$ (4 mL). After 1 h, an additional portion of bis(2-methoxyethyl)aminosulfur trifluoride (0.050 mL) was added and the solution was stirred for an additional 15 min then saturated aqueous NaHCO$_3$ was added and the mixture was stirred at room temperature for 16 h. The phases were separated and the aqueous layer was extracted with CH$_2$Cl$_2$. The combined organics were dried over MgSO$_4$ and concentrated to yield 296 mg of a light orange oil. Flash chromatography on a 1.5"×1.5" silica gel column flushing first with 200 mL EtOAc to remove higher Rf impurities followed by elution with 200 mL of 20% MeOH/EtOAc afforded 0.244 g (61%) of the title compound as a light yellow oil: R$_f$=0.10 (20% MeOH/EtOAc).

The HCl salt of the title compound was prepared in EtOAc with 1.5 equivalents of 2N HCl/ethyl ether to afford a white solid: $^1$H NMR (MeOH-d$_4$) δ 7.59 (t, J=7.9 Hz, 1H), 7.38-7.32 (m, 2H), 4.44 (s, 2H), 3.75 (p, J=8.7 Hz, 1H), 3.55-3.45 (m, 2H), 3.22-3.15 (m, 2H), 3.01 (s, 3H), 2.92 (s, 3H), 2.84-2.80 (m, 2H), 2.76 (d, J=8.7 Hz, 2H), 2.21-2.09 (m, 2H), 2.05-1.90 (m, 2H); $^{13}$C NMR (MeOH-d$_4$) δ 174.2, 161.5 (d, J$_{C-F}$=248.8 Hz), 147.4 (dd, J$_{C-F}$=24.1, 7.5 Hz), 133.1 (d, J$_{C-F}$=3.0 Hz), 121.3 (dd, J$_{C-F}$=7.9, 3.2 Hz), 117.6 (d, J$_{C-F}$=15.4 Hz), 112.3 (dd, J$_{C-F}$=23.3, 9.0 Hz), 95.9 (dd, J$_{C-F}$=197.3, 2.1 Hz) 53.9, 50.7 (d, J$_{C-F}$=3.0 Hz), 38.1 (d, J$_{C-F}$=24.8 Hz), 36.0, 34.8, 29.8, 22.6; LRMS m/z Calcd for C$_{18}$H$_{24}$F$_2$N$_2$O, 322.4, found, 323.4 (M+H) APCI.

Example 23

3-Fluoro-3-(3-fluoro-4-pyrrolidin-1-ylmethyl-phenyl)-cyclobutanecarboxylic acid ethyl-methyl-amide A solution of example 14, 3-(3-Fluoro-4-pyrrolidin-1-ylmethyl-phenyl)-3-hydroxy-cyclobutanecarboxylic acid ethyl-methyl-amide (0.40 g, 1.20 mmol) in CH$_2$Cl$_2$ (4 mL) was added to a −78° C. solution of bis(2-methoxyethyl)aminosulfur trifluoride (0.27 mL, 1.46 mmol) in CH$_2$Cl$_2$ (4 mL). After 1 h, saturated aqueous NaHCO$_3$ (10 mL) was added and the mixture was stirred at room temperature for 16 h. The phases were separated and the aqueous layer was extracted with CH$_2$Cl$_2$. The combined organics were dried over MgSO$_4$ and concentrated to yield 296 mg of a light orange oil. Flash chromatography on a 1.5"×1.5" silica gel column flushing first with 200 mL EtOAc to remove higher Rf impurities followed by elution with 200 mL each of 10% and 20% MeOH/EtOAc afforded 0.242 g (61%) of the title compound as a light yellow oil: R$_f$=0.24 (20% MeOH/EtOAc); LRMS m/z Calcd for C$_{19}$H$_{26}$F$_2$N$_2$O, 336.4, found, 337.4 (M+H), 317.4 (M+H−HF) APCI.

The HCl salt of the title compound was prepared in EtOAc with 1.5 equivalents of 2N HCl/ethyl ether to afford a light yellow solid: $^1$H NMR (MeOH-d$_4$) δ ~1:1 mixture of rotamers, 7.58 (t, J=7.7 Hz, 1H), 7.40-7.33 (m, 2H), 4.44 (s, 2H), 3.79-3.67 (m, 1H), 3.49 (br s, 2H), 3.42-3.34 (m, 2H), 3.21 (br s, 2H), 2.98 and 2.90 (singlets, 3H total), 2.86-2.74 (m, 4H), 2.23-1.90 (br m, 4H), 1.18 and 1.07 (triplets, J=7.1 Hz, 3H total); $^{13}$C NMR (MeOH-d$_4$) 6 (mixture of rotamers) 173.87, 173.65, 162.73, 160.26, 147.56, 147.49, 147.33, 147.25, 133.11, 133.08, 121.34, 121.31, 121.26, 121.23, 117.74, 117.59, 112.48, 112.39, 112.25, 112.16, 97.12, 96.89, 95.18, 94.93, 53.88, 50.75, 50.72, 44.12, 42.75, 38.55, 38.30, 38.19, 37.94, 33.66, 32.21, 29.97, 29.46, 22.62, 12.86, 11.25; LRMS m/z Calcd for C$_{19}$H$_{26}$F$_2$N$_2$O, 336.4, found, 337.4 (M+H) APCI.

Example 24

3-(3-Fluoro-4-pyrrolidin-1-ylmethyl-phenyl)-3-methoxy-cyclobutanecarboxylic acid ethyl-methyl-amide Sodium hydride (60% wt, 0.040 g, 1.00 mmol) was added to a solution of Example 14, 3-(3-Fluoro-4-pyrrolidin-1-yl-methyl-phenyl)-3-hydroxy-cyclobutanecarboxylic acid ethyl-methyl-amide (0.25 g, 0.748 mmol) in THF (5 mL). After stirring for 15 min, all gas evolution ceased and methyliodide (0.06 mL, 0.96 mmol) was added. The resulting mixture was stirred at room temperature for 16 h then quenched with water and extracted into EtOAc. The extract was washed with brine, dried over MgSO$_4$ and concentrated to give the title compound as a light yellow oil (0.13 g): R$_f$=0.16 (20% MeOH/EtOAc); LRMS m/z Calcd for C$_{20}$H$_{29}$FN$_2$O$_2$, 348.5, found, 349.4 (M+H) APCI.

The HCl salt of the title compound was prepared in EtOAc with 1.5 equivalents of 2N HCl/ethyl ether to afford a white solid: $^1$H NMR (MeOH-d$_4$) δ ~1:1 mixture of rotamers, 7.67 (t, J=7.7 Hz, 1H), 7.46 (d, J=8.3 Hz, 1H), 7.42 (dt, J=11.2, 1.9 Hz, 1H), 4.48 (s, 2H), 3.55 (br s, 2H), 3.42-3.18 (multiplets overlapping with MeOH, 4H), 3.02-2.95 (m, 1H), 2.94-2.90 (overlapping —OCH$_3$ singlet @2.94 and optometric —NCH$_3$ singlets @ 2.94 and 2.90, 6H total), 2.67-2.54 (m, 4H), 2.18 (br s, 2H), 2.03 (br s, 2H), 1.13 and 1.08 (triplets, J=7.3 Hz, 3H total); $^{13}$C NMR (MeOH-d$_4$) 6 (mixture of rotamers) 173.93, 173.84, 163.09, 160.61, 148.64, 148.57, 133.20, 133.18, 123.02, 117.39, 117.20, 114.13, 114.08, 113.91, 133.86, 76.72, 76.63, 53.88, 50.80, 50.77, 49.78, 43.97, 42.76, 36.58, 36.24, 33.64, 32.17, 27.87, 27.32, 22.67, 12.87, 11.28; LRMS m/z Calcd for C$_{20}$H$_{29}$FN$_2$O$_2$, 348.5, found, 349.4 (M+H) APCI.

Intermediate 16

3-(3-fluoro-4-((pyrrolidin-1-yl)methyl)phenyl)-N-isobutylcyclobut-2-enecarboxamide A solution of Example 20, 3-(3-Fluoro-4-pyrrolidin-1-ylmethyl-phenyl)-3-hydroxy-cyclobutanecarboxylic acid isobutyl-amide (3.71 g, 10.64 mmol) in trifluoroacetic acid (20 mL) and 1,2-dichloroethane (120 mL) was refluxed for 21 h and concentrated to give 8.6 g of crude 3-(3-fluoro-4-(pyrrolidin-1-ylmethyl)phenyl)-N-isobutylcyclobut-2-enecarboxamide trifluoroacetate salt and residual TFA as a dark red-brown oil. Diagnostic $^1$H NMR signals: (CDCl$_3$) δ 7.48 (t, J=7.7 Hz, 1H), 7.23 (d, partially obscured by CHCl$_3$ signal, 1H), 7.09 (dd, J=10.3, 1.5 Hz, 1H), 6.38 (d, J=0.8 Hz, 1H), 4.33 (d, J=5.0 Hz, 1H), 3.77 (br s, 2H), 3.68 (d, J=4.6 Hz, 1H), 3.20-3.07 (m, 3 h), 2.98 (br s, 2H), 2.83 (dd, J=13.3, 1.7 Hz, 1H), 2.19-2.07 (m, 4H), 0.90 (d, J=7.1H, 6H).

Example 25

3-(3-Fluoro-4-pyrrolidin-1-ylmethyl-phenyl)-cyclobutanecarboxylic acid isobutyl-amide Crude intermediate 16, 3-(3-fluoro-4-((pyrrolidin-1-yl)methyl)phenyl)-N-isobutylcyclobut-2-enecarboxamide prepared above was dissolved in EtOH (100 mL) and added to a hydrogenation bottle containing 10% palladium on carbon slurried in EtOH (~5 mL). The mixture was shaken at room temperature under 45 psi of hydrogen for 2 h, filtered through diatomaceous earth with an EtOH rinse and concentrated to yield an orange oil. This was dissolved in EtOAc (150 mL) and washed with aqueous K$_2$CO$_3$ and brine, dried over MgSO$_4$ and concentrated to afford 3.29 g of waxy orange solid. Flash chromatography on a 2.5"×4" silica gel column eluting with 1000 mL EtOAc and 500 mL 10% MeOH/EtOAc afforded 1.90 g (54%) of the title compound as a yellow tinged solid: R$_f$=0.26 (20% MeOH/EtOAc).

The HCl salt of the title compound was prepared by addition of ~1.2 eq. of 2N HCl/ethyl ether to the free base in EtOAc solution. The resulting hygroscopic, glassy, light orange solid had: $^1$H NMR (MeOH-d$_4$) δ 7.49 (t, J=8.1 Hz, 1H), 7.20-7.17 (m, 2H), 4.41 (s, 2H), 3.55-3.45 (m, 3H), 3.21-3.15 (m, 2H), 3.09 (p, 8.7 Hz, 1H), 2.98 (d, J=6.6 Hz, 2H), 2.57-2.50 (sym. mult., 2H), 2.31 (dq, J=9.7, 2.5 Hz, 2H), 2.22-2.10 (m, 2H), 2.05-1.95 (m, 2H), 1.75 (hept, J=6.8 Hz, 1H), 0.88 (d, J=6.6 Hz, 6H); $^{13}$C NMR (CDCl$_3$) δ 176.1, 161.64 (d, J$_{C-F}$=248.1 Hz), 150.7 (d, J$_{C-F}$=7.9 Hz), 132.8 (d, J$_{C-F}$=3.4 Hz), 123.2 (d, J$_{C-F}$=3.0 Hz), 115.7 (d, J$_{C-F}$=5.4 Hz), 113.8 (d, J$_{C-F}$=21.8 Hz), 53.73, 50.9, 50.8, 35.2, 34.9, 32.5, 28.4, 22.6, 19.3; LRMS m/z Calcd for C$_{20}$H$_{29}$FN$_2$O, 332.5, found, 333.5 (M+H) APCI.

Example 26

3-aza-bicyclo[3.2.2]nonan-3-yl(3-(3-fluoro-4-(pyrrolidin-1-ylmethyl)phenyl)-3-hydroxycyclobutyl)methanone A THF solution of crude intermediate 15, 3-(3-fluoro-4-(pyrrolidin-1-ylmethyl)phenyl)-3-hydroxycyclobutanecarboxylic acid (~5.3 mmol, ~0.12M THF) was combined with 3-aza-bicyclo[3.2.2]nonane (1.00 g, 7.99 mmol) and T3P (50% wt in EtOAc, 3.8 mL, 6.38 mmol) and stirred at room temperature for 30 min. The mixture was made basic with saturated aqueous NaHCO$_3$ and then EtOAc (50 mL) was added. The phases were separated and the aqueous phase was extracted again with EtOAc. The combined organic layers were washed with brine, dried over MgSO$_4$ and concentrated to yield a thick orange oil (1.86 g). Flash chromatography on a 2"×5" silica gel column flushing first with EtOAc (500 mL) followed by elution with 500 mL 25% MeOH/EtOAc afforded the title compound (0.59 g 28% yield) as a waxy yellow solid: LRMS m/z Calcd for C$_{24}$H$_{33}$FN$_2$O$_2$, 400.5, found, 401.1 (M+H) APCI; $^1$H NMR (CDCl$_3$) δ 7.40 (t, J=7.5 Hz, 1H), 7.23-7.17 (m, 2H), 3.75 (d, J=4.6 Hz, 2H), 3.69 (s, 2H), 3.29 (d, J=3.7 Hz, 2H), 3.25-3.19 (m, 1H), 2.84-2.78 (m, 2H), 2.62-2.45 (m, 6H), 2.10-2.08 (m, 1H), 2.03-2.00 (m, 1H), 1.93-1.40 (m, 12H).

Example 27

3-aza-bicyclo[3.2.2]nonan-3-yl(3-(3-fluoro-4-(pyrrolidin-1-ylmethyl)phenyl)cyclobutyl)methanone A solution of example 26, 3-aza-bicyclo[3.2.2]nonan-3-yl (3-(3-fluoro-4-(pyrrolidin-1-ylmethyl)phenyl)-3-hydroxycyclobutyl)methanone (0.59 g, 1.48 mmol) in trifluoroaceticacid (2.5 mL) and 1,2-dichloroethane (16 mL) was refluxed for 20 h and concentrated to give crude 3-aza-bicyclo[3.2.2] nonan-3-yl(3-(3-fluoro-4-(pyrrolidin-1-ylmethyl)phenyl)cyclobut-2-enyl)methanone trifluoroacetate salt as a dark purplish-brown oil, with residual TFA. This material was dissolved in EtOH (40 mL) and added to a hydrogenation bottle containing 10% palladium on carbon (93 mg) slurried in EtOH (~3 mL). The mixture was shaken at room temperature under 48 psi of hydrogen for 2 h, filtered through diatomaceous earth with an EtOH rinse and concentrated to yield an orange oil. This was dissolved in EtOAc and washed with aqueous K$_2$CO$_3$ and brine, dried over MgSO$_4$ and concentrated to afford 0.38 g of light orange oil. Flash chromatography on a 2"×3.5" silica gel column flushing with 2% MeOH/EtOAc (500 mL) and then eluting with 500 ml each 5% and 10% MeOH/EtOAc afforded 0.256 g (45%) of the title compound as a light orange oil: R$_f$=0.21 (20% MeOH/EtOAc).

The HCl salt was prepared by addition of ~1.5 eq. of 2N HCl/ethyl ether to the free base in EtOAc solution. The resulting white solid was collected, and dried to give the HCl salt of the title compound: $^1$H NMR (CDCl$_3$) δ 12.68 (br s, 1H), 7.80 (t, J=7.7 Hz, 1H), 7.19-6.97 (m, 2H), 4.21 (d, J=4.2 Hz, 2H), 3.80-3.56 (m, 4H), 3.55-3.37 (m, 3H), 3.28 (p, J=8.9 Hz, 1H), 2.83 (br s, 2H), 2.61-2.54 (m, 2H), 2.47-2.38 (m, 2H), 2.32-2.12 (m, 2H), 2.12-1.92 (m, 4H), 1.77-1.54 (m, 8H); $^{13}$C NMR (CDCl$_3$) δ 173.4, 161.5 (d, J$_{C-F}$=248.4 Hz), 150.6 (d, J$_{C-F}$=7.5 Hz), 133.6 (d, J$_{C-F}$=2.3 Hz), 124.0 (d, J$_{C-F}$=3.0 Hz), 114.3 (d, J$_{C-F}$=13.9 Hz), 113.8 (d, J$_{C-F}$=21.8 Hz), 54.3, 52.7, 50.3, 50.03, 50.0, 35.2, 33.9, 33.0, 30.4, 30.0, 25.0, 24.7, 23.3; LRMS m/z Calcd for C$_{24}$H$_{33}$FN$_2$O, 384.5, found, 385.5 (M+H) APCI.

Intermediate 17

3-(3-chloro-4-((pyrrolidin-1-yl)methyl)phenyl)-3-hydroxycyclobutanecarboxylic acid A 2.5 M solution of n-BuLi in hexanes (101 mL, 254 mmol) was added over 15 min to a solution of 1-(4-bromo-2-chlorobenzyl)pyrrolidine (69.6 g, 254 mmol) in absolute THF (450 ml) under a flow of nitrogen at −78° C. The reaction mixture was stirred at −78° C. for 30 min. Then a −78° C. chilled solution of 3-oxocyclobutanecarboxylic acid (14.4 g, 126.7 mmol) in absolute THF (150 ml) was added drop wise for 10 min at −78° C. The mixture was warmed to RT slowly and left stirring for 18 hrs and the resulting solution was used. LRMS m/z Calcd for C$_{16}$H$_{20}$NClO$_3$, 309.8, found, 308.1 (M−H) APCI.

Example 28

3-(3-Chloro-4-pyrrolidin-1-ylmethyl-phenyl)-3-hydroxy-cyclobutanecarboxylic acid methylamide To a crude solution of intermediate 17, 3-(3-chloro-4-((pyrrolidin-1-yl)methyl)phenyl)-3-hydroxycyclobutanecarboxylic acid (~666 mL, ~121.5 mmol) was added 2.0 M methylamine (95 mL, 190 mmol, in THF) and T$_3$P (50 wt % solution in EtOAc, 96.6 mL, 152 mmol). The resulting reaction mixture was stirred at RT for 1 hr and then 300 ml of 1N NaOH and 400 mL of EtOAc were added and the layers were separated. The aqueous layer was subjected to EtOAc extraction (2×500 ml) again and the combined organic layers were dried over MgSO$_4$ and evaporated. The residue was purified by flash column chromatography using a 75 L Biotage™ column, eluting with gradients of 5%, 8%, 10%, 15% MeOH/CH$_2$Cl$_2$ with 0.25% NH$_4$OH. The product containing fractions were collected and concentrated under reduced pressure to give the title compound (18.9 g, 48% yield). R$_f$=0.35 (20% MeOH/CH$_2$Cl$_2$+0.2% NH$_4$OH); LRMS m/z Calcd for C$_{17}$H$_{23}$ClN2 O2, 322.2, found, 323.1 (M+1) APCI; 400 MHz $^1$H NMR (CDCl$_3$) δ 7.47-7.45 (m, 2H), 7.33 (dd, J=7.9, 1.7 Hz, 1H), 5.94 (brs, 1H), 5.67 (brs, 1H), 3.75 (s, 3H), 2.85 (d, J=4.9 Hz, 3H), 2.86-2.73 (m, 3H), 2.62-2.56 (m, 4H), 2.54-2.47 (m, 2H), 1.84-1.76 (m 4H); 100 MHz $^{13}$C NMR (CDCl$_3$) δ 177.6, 146.0, 135.5, 134.0, 130.8, 126.3, 123.6, 74.3, 56.8, 54.3, 41.1, 33.3, 26.9, 23.7.

Example 29 and Example 30

Trans-3-(3-Chloro-4-pyrrolidin-1-ylmethyl-phenyl)-cyclobutanecarboxylic acid methylamide and Cis-3-(3-Chloro-4-pyrrolidin-1-ylmethyl-phenyl)-cyclobutanecarboxylic acid methylamide TFA (48 ml, 627 mmol) was added to a DCE solution (202 ml) of example 28, 3-(3-chloro-4-pyrrolidin-1-ylmethyl-phenyl)-3-hydroxy-cyclobutanecarboxylic acid methylamide (10 g, 31.4 mmol) and the resulting mixture was heated to 75° C. for 18 hrs and concentrated down to obtain the TFA salt of 3-(3-chloro-4-(pyrrolidin-1-yl)methyl)phenyl)-N-methylcyclobut-2-enecarboxamide. This was redissolved in absolute EtOH (130 ml), Wilkinson's catalyst (1.5 g) was then added and the reaction mixture was subjected to hydrogenation at 60° C. using 45 psi H$_2$. After 2 hr reaction time, it was concentrated down and the residue was redissolved into 1N HCl (100 ml) and extracted twice with EtOAc (2×100 ml). The aqueous layer was then basified with 1N NaOH (100 ml) and extracted with EtOAc (2×500 ml). The combined organic phases were dried over MgSO$_4$, and concentrated down to obtain crude material. This was purified by flash chromatography using a 120 g ISCO™ column eluting with a gradient of 5%, 10% and 15% MeOH/CH$_2$Cl$_2$ with 0.25% NH$_4$OH. The product containing fractions were combined and concentrated under reduced pressure to give a mixture of cis and trans isomers (4.6 g, 48% yield). The isomers were separated by preparative chromatography on a Chiralcel OD (10 cm×50 cm) column at a flow-rate of 295 ml/min and using Heptane/IPA (90/10) as eluent to recover trans (3.6 g) and cis (0.52 g) isomers.

Example 29

Trans-3-(3-Chloro-4-pyrrolidi n-1-ylmethyl-phenyl)-cyclobutanecarboxylic acid methylamide: R$_f$=0.50 (20% MeOH/CH$_2$Cl$_2$+0.2% NH$_4$OH); LRMS m/z Calcd for C$_{17}$H$_{23}$Cl N2 O, 306.8, found, 307.4 (M+1) APCI; 400 MHz $^1$H NMR (CDCl$_3$) δ 7.42 (d, J=7.8 Hz, 1H), 7.20 (d, J=1.6 Hz, 1H), 7.09 (dd, J=7.8, 1.2 Hz, 1H), 5.76 (brs, 1H), 3.83 (s, 2H), 3.76-3.67 (m, 1H), 2.98-2.90 (m, 1H), 2.82 (d, J=5.1 Hz, 3H), 2.80-2.62 (m, 6H), 2.36-2.26 (m, 2H), 1.87-1.78 (m, 4H); 100 MHz $^{13}$C NMR (CDCl$_3$) δ 146.7, 134.2, 131.3, 176.1 127.5, 125.3, 56.3, 54.3, 54.1, 36.5, 36.3, 32.1, 26.6, 23.6.

Example 30

Cis-3-(3-Chloro-4-pyrrolidin-1-ylmethyl-phenyl)-cyclobutanecarboxylic acid methylamide: R$_f$=0.50 (20% MeOH/CH$_2$Cl$_2$+0.2% NH$_4$OH); LRMS m/z Calcd for C17H23 Cl N2 O, 306.8, found, 307.4 (M+1) APCI; 400 MHz $^1$H NMR (CDCl$_3$) δ 7.30 (d, J=7.9 Hz, 1H), 7.15 (d, J=1.2 Hz, 1H), 7.03 (dd, J=7.8, 1.2 Hz, 1H), 6.48 (brs, 1H), 3.63 (s, 2H), 3.30-3.19 (m, 1H), 2.94-2.84 (m, 1H), 2.70 (d, J=5.0 Hz, 3H), 2.52-2.26 (m, 8H), 1.74-1.66 (m, 4H).

Example 31

3-(3-Chloro-4-pyrrolidin-1-ylmethyl-phenyl)-3-hydroxy-cyclobutanecarboxylic acid dimethylamide To a solution of crude intermediate 17, 3-(3-chloro-4-((pyrrolidin-1-yl)methyl)phenyl)-3-hydroxycyclobutanecarboxylic acid (~4.3 mL ~0.65 mmol) was added dimethylamine in THF (0.65 ml, 1.29 mmol, 2.0M THF) and T$_3$P (50 wt % solution in EtOAc, 0.62 ml, 0.97 mmol). The resulting reaction mixture was stirred at RT for 1 hr and then 25 ml of 1N NaOH and 100 ml of EtOAc were added and the layers were separated. The aqueous layer was subjected to EtOAc extraction (2×60 ml) again and the combined organic layers were dried over MgSO$_4$ and evaporated. The residue was purified by flash column chromatography using a 40 g ISCO™ column, eluting with 5% MeOH/CH$_2$Cl$_2$ containing 0.25% NH$_4$OH. The product containing fractions were collected and concentrated under reduced pressure to give the title compound (112 mg, 52% yield). $R_f$=0.65 (20% MeOH/ CH$_2$Cl$_2$+0.2% NH$_4$OH); LRMS m/z Calcd for C$_{18}$H$_{25}$Cl N2 O2, 336.8, found, 337.1 (M+1) APCI; 400 MHz $^1$H NMR (CDCl$_3$) δ (d, J=1.7 Hz, 1H), 7.46 7.40 (d, J=7.9 Hz, 1H), 7.33 (dd, J=7.9, 1.7 Hz, 1H), 3.68 (s, 2H), 3.06-2.96 (m, 1H), 2.92 (s, 6H), 2.78-2.68 (m, 2H), 2.62-2.46 (m, 6H), 1.76-1.68 (m, 4H); 100 MHz $^{13}$C NMR (CDCl$_3$) δ 175.5, 146.2, 135.5, 133.9, 130.7, 126.5, 123.7, 72.9, 56.8, 54.3, 40.9, 37.4, 36.1, 28.5, 23.7.

Example 32

[3-(3-Chloro-4-pyrrolidin-1-ylmethyl-phenyl)-3-hydroxy-cyclobutyl]-piperidin-1-yl-methanone To a solution of crude intermediate 17, 3-(3-chloro-4-((pyrrolidin-1-yl)methyl)phenyl)-3-hydroxycyclobutanecarboxylic acid (~4.3 mL ~0.65 mmol) was added piperidine (0.13 ml, 1.29 mmol) and T$_3$P (50 wt % solution in EtOAc, 0.62 ml, 0.97 mmol). The resulting reaction mixture was stirred at RT for 1 hr and then 25 ml of 1N NaOH and 100 ml of EtOAc were added and the layers were separated. The aqueous layer was subjected to EtOAc extraction (2×60 ml) again and the combined organic layers were dried over MgSO$_4$ and evaporated. The residue was purified by flash column chromatography using a 40 g ISCO™ column, eluting with 5% MeOH/CH$_2$Cl$_2$ containing 0.25% NH$_4$OH. The product containing fractions were collected and concentrated under reduced pressure to give the title compound (113 mg, 46% yield). $R_f$=0.80 (20% MeOH/CH$_2$Cl$_2$+0.2% NH$_4$OH); LRMS m/z Calcd for C$_{21}$H$_{29}$Cl N2 O2, 376.9, found, 377.1 (M+1) APCI; 400 MHz $^1$H NMR (CDCl$_3$) δ 7.47 (d, J=2.1 Hz, 1H), 7.42 (d, J=7.9 Hz, 1H), 7.34 (dd, J=7.9, 1.7 Hz, 1H), 3.70 (s, 2H), 3.54-3.48 (m, 2H), 3.32-3.26 (m, 2H), 3.02-2.93 (m, 1H), 2.75-2.67 (m, 2H), 2.65-2.51 (m, 6H), 1.78-1.71 (m, 4H), 1.63-1.44 (m, 6H); 100 MHz $^{13}$C NMR (CDCl$_3$) δ 173.5, 146.3, 135.4, 133.9, 130.8, 126.5, 123.7, 72.9, 56.7, 54.3, 46.8, 43.5, 41.0, 28.4, 26.8, 25.8, 24.7, 23.7.

Example 33

3-(3-Chloro-4-pyrrolidin-1-ylmethyl-phenyl)-3-hydroxy-cyclobutanecarboxylic acid isobutyl-methyl-amide To a solution of crude intermediate 17, 3-(3-chloro-4-((pyrrolidin-1-yl)methyl)phenyl)-3-hydroxycyclobutanecarboxylic acid (~4.3 mL ~0.65 mmol) was added N-methylisobutylamine (0.15 ml, 1.29 mmol) and T$_3$P (50 wt % solution in EtOAc, 0.62 ml, 0.97 mmol). The resulting reaction mixture was stirred at RT for 1 hr and then 25 ml of 1N NaOH and 100 ml of EtOAc were added and the layers were separated. The aqueous layer was subjected to EtOAc extraction (2×60 ml) again and the combined organic layers were dried over MgSO$_4$ and evaporated. The residue was purified by flash column chromatography using a 40 g ISCO™ column, eluting with 5% MeOH/CH$_2$Cl$_2$ containing 0.25% NH$_4$OH. The product containing fractions were collected and concentrated under reduced pressure to give the title compound (108 mg, 44% yield). $R_f$=0.80 (20% MeOH/CH$_2$Cl$_2$+0.2% NH$_4$OH); LRMS m/z Calcd for C$_{21}$H$_{31}$Cl N2 O2, 378.9, found, 379.1 (M+1) APCI; 400 MHz $^1$H NMR (CDCl$_3$) 1:1 mixture of rotomers, δ 7.47-7.45 (m, 1H), 7.42 (d, J=7.9 Hz, 1H), 7.36-7.30 (m, 1H), 3.71 (s, 2H), 3.20-3.02 (m, 3H), 2.92 & 2.90 (2 s, 3H total), 2.80-2.70 (m, 2H), 2.60-2.50 (m, 6H), 1.95-1.80 (m, 1H), 1.78-1.70 (m, 4H), 0.76-0.58 (m, 6H); 100 MHz $^{13}$C NMR (CDCl$_3$) 1:1 mixture of rotomers, line list δ 176.6, 175.8, 146.4, 135.2, 135.1, 134.0, 130.9, 130.8, 126.4, 123.7, 123.6, 73.5, 73.3, 57.9, 56.7, 55.6, 54.3, 41.4, 41.0, 36.1, 35.0, 29.0, 28.2, 27.9, 26.9, 23.7, 20.2, 20.1.

Example 34

3-(3-Chloro-4-pyrrolidin-1-ylmethyl-phenyl)-3-hydroxy-cyclobutanecarboxylic acid cyclopropylmethyl-amide To a solution of crude intermediate 17, 3-(3-chloro-4-((pyrrolidin-1-yl)methyl)phenyl)-3-hydroxycyclobutanecarboxylic acid (~4.3 mL ~0.65 mmol) was added aminomethylcyclopropane (0.112 ml, 1.29 mmol) and T$_3$P (50% solution in EtOAc, 0.62 ml, 0.97 mmol). The resulting reaction mixture was stirred at RT for 1 hr and then 25 ml of 1N NaOH and 100 ml of EtOAc were added and the layers were separated. The aqueous layer was subjected to EtOAc extraction (2×60 ml) again and the combined organic layers were dried over MgSO$_4$ and evaporated. The residue was purified by flash column chromatography using a 40 g ISCO™ column, eluting with 5% MeOH/CH$_2$Cl$_2$ containing 0.25% NH$_4$OH. The product containing fractions were collected and concentrated under reduced pressure to give the title compound (101 mg, 43% yield). $R_f$=0.80 (20% MeOH/CH$_2$Cl$_2$+0.2% NH$_4$OH); LRMS m/z Calcd for C$_{20}$H$_{27}$Cl N2 O2, 362.9, found, 363.2 (M+1) APCI; 400 MHz $^1$H NMR (CDCl$_3$) δ 7.44-7.38 (m, 2H), 7.28 (dd, J=7.9, 2.6 Hz, 1H), 6.40 (br apt t, J=5.4 Hz, 1H), 3.69 (s, 2H), 3.10-3.04 (m, 2H), 2.76-2.68 (m, 3H), 2.57-2.42 (m, 6H), 1.78-1.69 (m, 4H), 0.94-0.84 (m, 1H), 0.48-0.40 (m, 2H), 0.18-0.12 (m, 2H); 100 MHz $^{13}$C NMR (CDCl$_3$) δ 176.7, 146.1, 135.3, 133.9, 130.8, 126.3, 123.6, 74.0, 56.7, 54.3, 44.9, 41.1, 40.7, 33.1, 23.7, 10.8, 3.7.

Example 35

3-(3-Chloro-4-pyrrolidin-1-ylmethyl-phenyl)-3-hydroxy-cyclobutanecarboxylic acid methyl-(tetrahydro-pyran-4-ylmethyl)-amide To a solution of crude intermediate 17, 3-(3-chloro-4-((pyrrolidin-1-yl)methyl)phenyl)-3-hydroxycyclobutanecarboxylic acid (~4.3 mL ~0.65 mmol) was added methyl-(tetrahydro-pyran-4-ylmethyl)-amine hydrochloride (200 mg, 1.21 mmol), triethylamine (0.108 ml, 0.78 mmol) and T$_3$P (50% solution in EtOAc, 0.62 ml, 0.97 mmol). The resulting reaction mixture was stirred at rt for 1 hr and then 25 ml of 1N NaOH and 100 ml of EtOAc were added and the layers were separated. The aqueous layer was subjected to EtOAc extraction (2×60 ml) again and the combined organic layers were dried over MgSO$_4$ and evaporated. The residue was purified by flash column chromatography using a 40 g ISCO™ column, eluting with 5% MeOH/CH$_2$Cl$_2$ containing 0.25% NH$_4$OH. The product containing fractions were collected and concentrated under reduced pressure to give the title compound (87 mg, 32% yield). $R_f$=0.80 (20% MeOH/CH$_2$Cl$_2$+0.2% NH$_4$OH); LRMS m/z Calcd for C$_{23}$H$_{33}$Cl N2 O, 420.9, found, 421.3 (M+1) APCI; 400 MHz $^1$H NMR (CDCl$_3$) mixture of rotomers, diagnostic peaks, δ 3.98-3.88 (m, 2H), 3.73 (s, 2H), 2.95 (s, 3H), 2.62-2.54 (m, 6H), 1.70-1.46 (m, 2H), 1.38-1.17 (m, 2H).

Example 36

3-(3-Chloro-4-pyrrolidin-1-ylmethyl-phenyl)-3-hydroxy-cyclobutanecarboxylic acid cyclopropylmethyl-methyl-amide To a solution of crude intermediate 17, 3-(3-chloro-4-((pyrrolidin-1-yl)methyl)phenyl)-3-hydroxycyclobutanecarboxylic acid (~4.3 mL ~0.65 mmol) was added cyclopropylmethyl-methyl-amine hydrochloride (61 mg, 0.51 mmol), triethylamine (0.18 ml, 1.29 mmol) and $T_3P$ (50% solution in EtOAc, 0.62 ml, 0.97 mmol). The resulting reaction mixture was stirred at RT for 1 hr and then 25 ml of 1N NaOH and 100 ml of EtOAc were added and the layers were separated. The aqueous layer was subjected to EtOAc extraction (2×60 ml) again and the combined organic layers were dried over $MgSO_4$ and evaporated. The residue was purified by flash column chromatography using a 40 g ISCO™ column, eluting with 5% $MeOH/CH_2Cl_2$ containing 0.25% $NH_4OH$. The product containing fractions were collected and concentrated under reduced pressure to give the title compound (71 mg, 29% yield). $R_f$=0.50 (15% $MeOH/CH_2Cl_2$+0.2% $NH_4OH$); LRMS m/z Calcd for $C_{21}H_{29}Cl\,N2\,O2$, 376.9, found, 377.2 (M+1) APCI; 400 MHz $^1H$ NMR ($CDCl_3$) 1:1 mixture of rotomers, diagnostic peaks, δ 3.75 (s, 2H), 3.02 & 3.01 (2 singlets, 3H total), 2.62-2.54 (m, 6H), 1.82-1.74 (m, 4H); 100 MHz $^{13}C$ NMR ($CDCl_3$) 1:1 mixture of rotomers, peak list δ 175.9, 175.7, 146.4, 146.3, 135.2, 134.0, 130.9, 130.8, 126.5, 126.4, 123.7, 73.7, 73.5, 56.7, 54.6, 54.3, 52.4, 41.3, 41.0, 35.5, 34.5, 29.0, 28.5, 23.7, 10.5, 9.5, 3.8, 3.6.

Example 37

[3-(3-Chloro-4-pyrrolidin-1-ylmethyl-phenyl)-3-hydroxy-cyclobutyl]-(2,3-dihydro-5H-benzo[f][1,4]oxazepin-4-yl)-methanone To a solution of crude intermediate 17, 3-(3-chloro-4-((pyrrolidin-1-yl)methyl)phenyl)-3-hydroxycyclobutanecarboxylic acid (~4.3 mL ~0.65 mmol) was added 2,3,4,5-tetrahydro-benzo[f][1,4]oxazepine hydrochloride (239 mg, 1.29 mmol), triethylamine (0.18 ml, 1.29 mmol) and $T_3P$ (50% solution in EtOAc, 0.62 ml, 0.97 mmol). The resulting reaction mixture was stirred at RT for 1 hr and then 25 ml of 1N NaOH and 100 ml of EtOAc were added and the layers were separated. The aqueous layer was subjected to EtOAc extraction (2×60 ml) again and the combined organic layers were dried over $MgSO_4$ and evaporated. The residue was purified by flash column chromatography using a 40 g ISCO™ column, eluting with 5% $MeOH/CH_2Cl_2$ containing 0.25% $NH_4OH$. The product containing fractions were collected and concentrated under reduced pressure to give the title compound 104 mg, 37% yield. $R_f$=0.50 (15% $MeOH/CH_2Cl_2$+0.2% $NH_4OH$); LRMS m/z Calcd for $C_{25}H_{29}Cl\,N2\,O3$, 440.9, found, 441.2 (M+1) APCI; 100 MHz $^{13}C$ NMR ($CDCl_3$) 1:1 mixture of rotomers, diagnostic peaks, δ 175.4, 173.9, 159.5, 159.3, 134.2, 134.1, 131.4, 131.3, 122.0, 121.3, 121.0, 74.9, 72.6, 72.2, 56.3, 54.1, 53.9, 49.3, 48.7, 41.2, 41.0, 28.8, 28.5, 23.7, 23.6.

Example 38

3-(3-Chloro-4-pyrrolidin-1-ylmethyl-phenyl)-3-hydroxy-cyclobutanecarboxylic acid methyl-(3-methyl-pyridin-2-ylmethyl)-amide To a solution of crude intermediate 17, 3-(3-chloro-4-((pyrrolidin-1-yl)methyl)phenyl)-3-hydroxycyclobutanecarboxylic acid (~4.3 mL ~0.65 mmol) was added methyl-(3-methyl-pyridin-2-ylmethyl)-amine (176 mg, 1.29 mmol) and $T_3P$ (50% solution in EtOAc, 0.62 ml, 0.97 mmol). The resulting reaction mixture was stirred at RT for 1 hr and then 25 ml of 1N NaOH and 100 ml of EtOAc were added and the layers were separated. The aqueous layer was subjected to EtOAc extraction (2×60 ml) again and the combined organic layers were dried over $MgSO_4$ and evaporated. The residue was purified by flash column chromatography using a 40 g ISCO™ column, eluting with 5% $MeOH/CH_2Cl_2$ containing 0.25% $NH_4OH$. The product containing fractions were collected and concentrated under reduced pressure to give the title compound 127 mg, 46% yield). $R_f$=0.30 (15% $MeOH/CH_2Cl_2$+0.2% $NH_4OH$); LRMS m/z Calcd for $C_{24}H_{30}Cl\,N3\,O2$, 427.9, found, 428.2 (M+1) APCI; 400 MHz $^1H$ NMR ($CDCl_3$) 2:1 mixture of rotomers, diagnostic peaks, δ 4.72, 4.53 (s, 2H), 3.72 & 3.70 (s, 2H), 2.97, 2.93 (s, 3H), 1.76-1.74 (m, 4H); 100 MHz $^{13}C$ NMR ($CDCl_3$) 2:1 mixture of rotomers, diagnostic peaks δ 177.6, 175.7, 154.7, 153.6, 146.8, 146.6, 126.5, 126.4, 122.8, 122.7, 73.4, 73.2, 56.7, 56.6, 54.3, 54.2, 51.1, 41.4, 40.9, 35.6, 35.4, 28.9, 28.7, 23.7, 23.6, 18.3, 18.2.

Example 39

3-(3-Fluoro-4-pyrrolidin-1-ylmethyl-phenyl)-cyclobutanecarboxylic acid dimethylamide TFA (9.9 ml, 128 mmol) was added to a DCE solution (64 ml) of example 19, 3-(3-fluoro-4-pyrrolidin-1-ylmethyl-phenyl)-3-hydroxy-cyclobutanecarboxylic acid dimethylamide (2.05 g, 6.4 mmol) and the mixture was heated to 75° C. for 18 hrs and concentrated down to obtain TFA salt of intermediate 3-(3-fluoro-4-pyrrolidin-1-ylmethyl-phenyl)-cyclobut-2-enecarboxylic acid dimethylamide. This was redissolved in absolute EtOH (64 ml), Wilkinson's catalyst (296 mg) was then added and this mixture was subjected to hydrogenation at 60° C. using 45 psi $H_2$. After 1 hr 45 min reaction time, it was concentrated down and the residue was redissolved into 1N HCl (50 ml) and extracted twice with EtOAc (2×120 ml). The aqueous layer was then basified with 15% aq. NaOH (40 ml) and extracted with EtOAc (3×200 ml). The combined organic phases were dried over $MgSO_4$, and concentrated down to obtain crude material. This was purified by flash chromatography using a 120 g ISCO™ column and 4% $MeOH/CH_2Cl_2$ with 0.1% $NH_4OH$. The product containing fractions were combined and concentrated under reduced pressure to give the title compound (1.0 g, 51% yield). $R_f$=0.40 (10% $MeOH/CH_2Cl_2$+0.2% $NH_4OH$); LRMS m/z Calcd for $C_{18}H_{25}F\,N2\,O$, 304.4, found, 305.4 (M+1) APCI; 400 MHz $^1H$ NMR ($CDCl_3$) δ 7.10 (t, J=7.8 Hz, 1H), 6.78 (dd, J=1.2, 6.6 Hz, 1H), 6.72 (dd, J=1.7, 11.2 Hz, 1H), 3.4 (s, 2H), 3.48-3.38 (m, 1H), 3.13-3.04 (m, 1H), 2.79 (s, 3H), 2.70 (s, 3H), 2.58-2.50 (m, 2H), 2.37-2.30 (m, 4H), 2.22-2.12 (m, 2H), 1.60-1.52 (m, 4H); 100 MHz $^{13}C$ NMR ($CDCl_3$) δ 174.3, 161.2 (d, $J_{C-F}$=245.7 Hz), 147.0, 131.4, 123.4 (d, $J_{C-F}$=15.0 Hz), 121.9, 113.0 (d, $J_{C-F}$=22.5 Hz), 54.0, 52.5, 36.7, 35.8, 35.5, 33.3, 31.6, 23.5.

Example 40

[3-(3-Fluoro-4-pyrrolidin-1-ylmethyl-phenyl)-cyclobutyl]-pyrrolidin-1-yl-methanone TFA (10.2 ml, 133 mmol) was added to a DCE solution (66 ml) of Example 8, N-{2-fluoro-4-[1-hydroxy-3-(pyrrolidin-1-ylcarbonyl)cyclobutyl]benzyl}-pyrrolidine, (2.3 g, 6.7 mmol) and the mixture was heated to 75° C. for 18 hrs and concentrated down to obtain the TFA salt of intermediate [3-(3-fluoro-4-pyrrolidin-1-ylmethyl-phenyl)-cyclobut-2-enyl]-pyrrolidin-1-yl-methanone. This was redissolved in absolute EtOH (67 ml), Wilkinson's catalyst (308 mg) was then added and the mixture was subjected to hydrogenation at 60° C. using 45 psi $H_2$. After 1 hr 45 min reaction time, it was concentrated down and the residue was redissolved into 1N HCl (50 ml) and extracted twice with EtOAc (2×120 ml). The aqueous layer was then basified with 15% aq. NaOH (40 ml) and extracted with EtOAc (3×200 ml). The combined organic phases were dried over $MgSO_4$, and concentrated down to obtain crude material. This was purified by flash chromatography using a 120 g ISCO™ column and 4% MeOH/$CH_2Cl_2$ with 0.1% $NH_4OH$. The product containing fractions were combined and concentrated under reduced pressure to give the title compound (1.1 g, 50% yield). $R_f$=0.40 (10% MeOH/$CH_2Cl_2$+0.2% $NH_4OH$); LRMS m/z Calcd for $C_{20}H_{27}F$ N2 O, 330.4, found, 331.4 (M+1) APCI; 400 MHz $^1$H NMR ($CDCl_3$) δ 7.30 (t, J=7.6 Hz, 1H), 6.97 (dd, J=1.3, 7.9 Hz, 1H), 6.91 (dd, J=1.3, 11.2 Hz, 1H), 3.66 (s, 2H), 3.73-3.63 (m, 1H), 3.50 (t, J=6.7 Hz, 2H), 3.31 (t, J=6.5 Hz, 2H), 3.22-3.14 (m, 1H), 2.77-2.69 (m, 2H), 2.58-2.51 (m, 4H), 2.38-2.28 (m, 2H), 1.97-1.81 (m, 4H), 1.80-1.74 (m, 4H); 100 MHz $^{13}$C NMR ($CDCl_3$) δ 173.4, 161.4 (d, $J_{C-F}$=246.5 Hz), 147.4, 131.6 (d, $J_{C-F}$=4.50 Hz), 122.1, 113.2 (d, $J_{C-F}$=22.6 Hz), 112.5, 54.1, 52.7, 46.2, 46.1, 36.1, 34.6, 31.5, 26.3, 24.5, 23.6.

Example 41

3-(3-Fluoro-4-pyrrolidin-1-ylmethyl-phenyl)-cyclobutanecarboxylic acid isobutyl-amide TFA (14 ml, 184 mmol) was added to a DCE solution (80 ml) of Example 20, 3-(3-fluoro-4-pyrrolidin-1-ylmethyl-phenyl)-3-hydroxy-cyclobutanecarboxylic acid isobutylamide (3.2 g, 9.2 mmol) and the mixture was heated to 75° C. for 18 hrs and concentrated down to obtain the TFA salt of intermediate 3-(3-Fluoro-4-pyrrolidin-1-ylmethyl-phenyl)-cyclobut-2-enecarboxylic acid isobutyl-amide. This was redissolved in absolute EtOH (90 ml), Wilkinson's catalyst (424 mg) was then added and the mixture was subjected to hydrogenation at 60° C. using 45 psi $H_2$. After 2 hr reaction time, it was concentrated down and the residue was redissolved into 1N HCl (60 ml) and extracted twice with EtOAc (2×120 ml). The aqueous layer was then basified with 15% NaOH (40 ml) and extracted with EtOAc (3×250 ml). The combined organic phases were dried over $MgSO_4$, and concentrated down to obtain crude material. This was purified by flash chromatography using a 120 g ISCO™ column and 4% and 8% MeOH/$CH_2Cl_2$ with 0.1% $NH_4OH$. The product containing fractions were combined and concentrated under reduced pressure to give the title compound (885 mg, 26% yield). $R_f$=0.30 (10% MeOH/$CH_2Cl_2$+0.2% $NH_4OH$); LRMS m/z Calcd for $C_{20}H_{29}F$ N2 O, 332.4, found, 333.5 (M+1) APCI; 400 MHz $^1$H NMR ($CDCl_3$) δ 7.22 (t, J=7.9 Hz, 1H), 6.87 (dd, J=0.8, 8.7 Hz, 1H), 6.82 (dd, J=1.2, 16.2 Hz, 1H), 6.08 (m) 3.72-3.61 (m, 1H), 3.57 (s, 2H), 3.04 (t, J=6.3 Hz, 2H), 3.02-2.82 (m, 1H), 2.65-2.56 (m, 2H), 2.50-2.43 (m, 4H), 2.32-2.22 (m, 2H), 1.78-1.66 (m, 5H), 0.86 (s, 3H), 0.84 (s, 3H); 100 MHz $^{13}$C NMR ($CDCl_3$) δ 175.5, 161.4 (d, $J_{C-F}$=246.4 Hz), 147.1, 131.5, 123.4 (d, $J_{C-F}$=14.3 Hz), 122.1, 113.1 (d, $J_{C-F}$=22.5 Hz), 54.1, 52.7, 47.1, 36.6, 36.3, 32.3, 28.8, 23.6, 20.3.

Example 42

3-(3-Fluoro-4-pyrrolidin-1-ylmethyl-phenyl)-cyclobutanecarboxylic acid ethylamide TFA (13 ml, 169 mmol) was added to a DCE solution (71 ml) of Example 12, 3-(3-Fluoro-4-pyrrolidin-1-ylmethyl-phenyl)-3-hydroxy-cyclobutanecarboxylic acid ethylamide (2.7 g, 8.4 mmol) and the mixture was heated to 75° C. for 18 hrs and concentrated down to obtain the TFA salt of intermediate 3-(3-Fluoro-4-pyrrolidin-1-ylmethyl-phenyl)-cyclobut-2-enecarboxylic acid ethylamide. This was redissolved in absolute EtOH (84 ml). Wilkinson's catalyst (390 mg) was then added and the mixture was subjected to hydrogenation at 60° C. using 45 psi $H_2$.

After 2 hr reaction time, it was concentrated down and the residue was redissolved into 1N HCl (60 ml) and extracted twice with EtOAc (2×120 ml). The aqueous layer was then basified with 15% NaOH (40 ml) and extracted with EtOAc (3×250 ml). The combined organic phases were dried over $MgSO_4$, and concentrated down to obtain crude material. This was purified by flash chromatography using a 120 g ISCO™ column and 4% and 8% MeOH/$CH_2Cl_2$ with 0.1% $NH_4OH$. The product containing fractions were combined and concentrated under reduced pressure to give the title compound (1.0 g, 39% yield). $R_f$=0.30 (10% MeOH/$CH_2Cl_2$+0.2% $NH_4OH$); LRMS m/z Calcd for $C_{18}H_{25}F$ N2 O, 304.4, found, 305.5 (M+1) APCI; 400 MHz $^1$H NMR ($CDCl_3$) δ 7.13 (t, J=7.9 Hz, 1H), 6.79 (dd, J=1.2, 7.9 Hz, 1H), 6.82 (dd, J=11.2, 0.8 Hz, 1H), 6.68 (m, 1H), 3.64-3.53 (m, 1H), 3.48 (s, 2H), 3.20-3.10 (m, 2H), 2.94-2.84 (1H), 2.58-2.50 (m, 2H), 2.44-2.32 (m, 4H), 2.22-2.12 (m, 2H), 1.66-1.56 (m, 4H), 1.00 (t, J=24.5 Hz, 3H); 100 MHz $^{13}$C NMR ($CDCl_3$) δ 175.4, 161.2 (d, $J_{C-F}$=246.5 Hz), 147.1, 131.4, 123.3 (d, $J_{C-F}$=15.0 Hz), 121.9, 113.0 (d, $J_{C-F}$=21.8 Hz), 54.0, 36.5, 36.1, 34.5, 34.2, 32.1, 23.6, 15.0.

Example 43

3-(3-Fluoro-4-pyrrolidin-1-ylmethyl-phenyl)-cyclobutanecarboxylic acid ethyl-methyl-amide TFA (13.5 ml, 175 mmol) was added to a DCE solution (87 ml) of Example 14, 3-(3-Fluoro-4-pyrrolidin-1-ylmethyl-phenyl)-3-hydroxy-cyclobutanecarboxylic acid ethyl-methyl-amide (2.9 g, 8.74 mmol) and the mixture was heated to 75° C. for 18 hrs and concentrated down to obtain the TFA salt of intermediate 3-(3-Fluoro-4-pyrrolidin-1-ylmethyl-phenyl)-cyclobut-2-enecarboxylic acid ethyl-methyl-amide. This was redissolved in absolute EtOH (87 ml), Wilkinson's catalyst (404 mg) was then added and the mixture was subjected to hydrogenation at 60° C. using 45 psi $H_2$. After 2 hr reaction time, it was concentrated down and the residue was redissolved into 1N HCl (60 ml) and extracted twice with EtOAc (2×120 ml). The aqueous layer was then basified with 15% NaOH (40 ml) and extracted with EtOAc (3×250 ml). The combined organic phases were dried over $MgSO_4$, and concentrated down to obtain crude material. This was purified by flash chromatography using a 120 g ISCO™ column and 4% and 8% MeOH/$CH_2Cl_2$ with 0.1% $NH_4OH$. The product containing fractions were combined and concentrated under reduced pressure to give the title compound (1.4 g, 44% yield). $R_f$=0.30 (10% MeOH/$CH_2Cl_2$+0.2% $NH_4OH$); LRMS m/z Calcd for $C_{19}H_{27}F$ N2 O, 318.4, found, 319.5 (M+1) APCI; 400 MHz $^1$H NMR ($CDCl_3$) δ 7.19 (t, J=7.9 Hz, 1H), 6.85 (dd, J=1.3, 7.9 Hz, 1H), 6.79 (dd, J=1.3, 11.2 Hz, 1H), 3.58-3.44 (m, 1H), 3.52 (s, 2H), 3.33 (q J=2.9 Hz, 1H), 3.20-3.07 (m, 2H), 2.83 (s, 3H), 2.76 (s, 3H), 2.66-2.56 (m, 2H), 2.45-2.36 (m, 4H), 2.28-2.18 (m, 2H), 1.68-1.58 (m, 4H), 1.02 (q, J=7.1 Hz, 3H); 100 MHz $^{13}$C NMR ($CDCl_3$) 1:1 mixture of rotomers, δ 174.2, 173.9, 161.2 (d, $J_{C-F}$=246.5 Hz), 147.1, 131.4, 123.3 (d, $J_{C-F}$=15.0 Hz), 121.9, 113.1 (d, $J_{C-F}$=21.8 Hz), 54.0, 52.6, 43.9, 42.6, 36.0, 35.8, 34.1, 33.6, 33.0, 32.7, 31.8, 31.6, 23.6, 13.8, 12.4.

Example 44

[3-(3-Chloro-4-pyrrolidin-1-ylmethyl-phenyl)-3-fluoro-cyclobutyl]-piperidin-1-yl-methanone A solution of example 32, [3-(3-Chloro-4-pyrrolidin-1-ylmethyl-phenyl)-3-hydroxy-cyclobutyl]-piperidin-1-yl-methanone (106 mg, 0.28 mmol) in dichloromethane (5 ml) was chilled to −78° C. and added drop wise to a −78° C. chilled solution of BAST (0.1 ml, 0.31 mmol) in dichloromethane (5 ml) under nitrogen. After 1 hr stirring at −78° C., the reaction mixture was poured into saturated aq. NaHCO$_3$ (15 ml) and stirred for 15 min. The layers were separated and after two more extractions of the aqueous phase with CH$_2$Cl$_2$ (2×20 ml), the combined organic extracts were dried over MgSO$_4$ and concentrated under reduced pressure to obtain a residual oil. This was purified by flash column chromatography using a 12 g ISCO™ column and 2% MeOH/CH$_2$Cl$_2$ to recover the title compound (28 mg, 26% yield). R$_f$=0.30 (5% MeOH/CH$_2$Cl$_2$); LRMS m/z Calcd for C$_{21}$H$_{28}$Cl F N2 O, 378.9, found, 379.4, 359.4 (M+1) & (M+1−HF) APCI; 400 MHz $^1$H NMR (CDCl$_3$) δ 7.50-7.46 (m, 1H), 7.40 (bs, 1H), 7.28 (dd, J=1.3, 7.9 Hz, 1H), 3.74 (s, 2H), 3.70-3.52 (m, 3H), 3.38-3.32 (m, 2H), 2.96-2.80 (m, 2H), 2.78-2.66 (m, 2H), 2.64-2.54 (m, 4H), 1.84-1.74 (m, 4H), 1.68-1.60 (m, 2H), 1.58-1.50 (m, 4H).

Example 45

3-(3-Chloro-4-pyrrolidin-1-ylmethyl-phenyl)-3-fluoro-cyclobutanecarboxylic acid isobutyl-methyl-amide A solution of Example 33, 3-(3-chloro-4-pyrrolidin-1-ylmethyl-phenyl)-3-hydroxy-cyclobutanecarboxylic acid isobutyl-methyl-amide (102 mg, 0.27 mmol) in dichloromethane (5 ml) was chilled to −78° C. and added drop wise to a −78° C. chilled solution of BAST (0.06 ml, 0.30 mmol) in dichloromethane (5 ml) under nitrogen. After 1 hr stirring at −78° C., the reaction mixture was poured into saturated aq. NaHCO$_3$ (15 ml) and stirred for 15 min. The layers were separated and after two more extractions of the aqueous phase with CH$_2$Cl$_2$ (2×20 ml), the combined organic extracts were dried over MgSO$_4$ and concentrated under reduced pressure to obtain a residual oil. This was purified by flash column chromatography using a 12 g ISCO™ column and 2% MeOH/CH$_2$Cl$_2$ to recover the title compound (24 mg, 23% yield).

R$_f$=0.35 (5% MeOH/CH$_2$Cl$_2$); LRMS m/z Calcd for C$_{21}$H$_{30}$Cl F N2 O, 380.9, found, 381.4, 361.4 (M+1) & (M+1−HF) APCI; 400 MHz $^1$H NMR (CDCl$_3$) 1:1 mixture of rotomers, diagnostic peaks, δ 3.74 (s, 2H), 3.56-3.51 (m, 1H), 3.21 (d, J=7.9 Hz, 1H), 3.07 (d, J=7.5 Hz, 1H), 2.62-2.54 (m, 4H), 2.00-1.88 (m, 1H), 1.85-1.75 (m, 4H); 100 MHz $^{13}$C NMR (CDCl$_3$) 1:1 mixture of rotomers, δ 173.7, 173.4, 136.8, 134.0, 130.8, 125.8, 125.8, 123.3, 123.2, 57.2, 56.8, 55.5, 54.4, 35.6, 34.2, 31.0, 39.2, 27.6, 26.9, 23.8, 20.2, 20.1.

Example 46

3-(3-Chloro-4-pyrrolidin-1-ylmethyl-phenyl)-3-fluoro-cyclobutanecarboxylic acid cyclopropylm-ethyl-amide A solution of Example 3-(3-(3-Chloro-4-pyrrolidin-1-ylmethyl-phenyl)-3-hydroxy-cyclobutanecarboxylic acid cyclopropylmethyl-amide (92 mg, 0.25 mmol) in dichloromethane (5 ml) was chilled to −78° C. and added drop wise to a −78° C. chilled solution of BAST (0.05 ml, 0.28 mmol) in dichloromethane (5 ml) under nitrogen. After 1 hr stirring at −78° C., the reaction mixture was poured into saturated aq. NaHCO$_3$ (15 ml) and stirred for 15 min. The layers were separated and after two more extractions of the aqueous phase with CH$_2$Cl$_2$ (2×20 ml), the combined organic extracts were dried over MgSO$_4$ and concentrated under reduced pressure to obtain a residual oil. This was purified by flash column chromatography using a 12 g ISCO™ column and 2% MeOH/CH$_2$Cl$_2$ to recover the title compound (47 mg, 51% yield). R$_f$=0.35 (5% MeOH/CH$_2$Cl$_2$); LRMS m/z Calcd for C$_{20}$H$_{26}$Cl F N2 O, 364.9, found, 365.4, 345.4 (M+1) & (M+1−HF) APCI; 400 MHz $^1$H NMR (CDCl$_3$) δ 7.48 (dd, J=1.2, 7.9 Hz, 1H), 7.43 (bs, 1H), 7.33 (dd, J=1.3, 7.9 Hz, 1H), 5.69 (bs, 1H), 3.73 (s, 2H), 3.32-3.22 (m, 1H), 3.15-3.10 (2H), 2.95-2.80 (m, 2H), 2.78-2.63 (m, 2H), 2.62-2.52 (m, 4H), 1.85-1.75 (m, 4H), 1.00-0.88 (m, 1H), 0.54-0.46 (m, 2H), 0.22-0.15 (m, 2H); 100 MHz $^{13}$C NMR (CDCl$_3$) 1:1 mixture of rotomers, peak list δ 173.6, 142.0, 141.8, 134.0, 130.7, 125.8, 123.3, 56.9, 54.4, 44.8, 38.9, 38.6, 33.4, 23.8, 10.9, 3.6.

Example 47 and Example 48 cis 3-(3-Fluoro-4-pyrrolidin-1-ylmethyl-phenyl)-cyclobutanecarboxylic acid methylamide and trans 3-(3-Fluoro-4-pyrrolidin-1-IA methyl-phenyl)-cyclobutanecarboxylic acid methylamide TFA (34.7 ml, 450 mmol) was added to a DCE solution (150 ml) of example 18, 3-(3-fluoro-4-pyrrolidin-1-ylmethyl-phenyl)-3-hydroxy-cyclobutanecarboxylic acid methylamide (10 g, 31.4 mmol) and the mixture was heated to 75° C. for 18 hrs and concentrated down to obtain the TFA salt of intermediate 3-(3-fluoro-4-(pyrrolidin-1-yl)methyl)phenyl)-cyclobut-2-enecarboxylic acid methylamide. This was redissolved in absolute EtOH (79 ml), Wilkinson's catalyst (1000 mg) was then added and the mixture was subjected to hydrogenation at 60° C. using 45 psi H$_2$. After 2 hr reaction time, it was concentrated down and the residue was redissolved into 1N HCl (100 ml) and extracted twice with EtOAc (2×100 ml). The aqueous layer was then basified with 1N NaOH (100 ml) and extracted with EtOAc (2×500 ml). The combined organic phases were dried over MgSO$_4$, and concentrated down to obtain crude material. This was purified by flash chromatography using a 120 g ISCO™ column and 5%, 10% and 15% MeOH/CH$_2$Cl$_2$ with 0.25% NH$_4$OH. The product containing fractions were combined and concentrated under reduced pressure to give a mixture of cis, trans isomers (4.8 g, 74% yield). The isomers were separated by preparative chromatography on a Chiralcel OD (10 cm×50 cm) column at a flow-rate of 295 ml/min and using Heptane/EtOH (95/5) as eluent to recover trans 3-(3-Fluoro-4-pyrrolidin-1-ylmethyl-phenyl)-cyclobutanecarboxylic acid methylamide (2.5 g) and cis 3-(3-Fluoro-4-pyrrolidin-1-ylmethyl-phenyl)-cyclobutanecarboxylic acid methylamide (0.23 g).

Example 47 cis 3-(3-Fluoro-4-pyrrolidin-1-ylmethyl-phenyl)-cyclobutanecarboxylic acid methylamide: R$_f$=0.50 (25% MeOH/CH$_2$Cl$_2$+0.2% NH$_4$OH); LRMS m/z Calcd for C$_{17}$H$_{23}$F N2 O, 290.4, found, 291.1 (M+1) APCI; 400 MHz $^1$H NMR (CDCl$_3$) δ 7.19 (t, J=7.8 Hz, 1H), 6.89 (dd, J=1.3, 8.2 Hz, 1H), 6.83 (dd, J=1.3, 10.9 Hz, 1H), 3.54 (s, 2H), 3.30-3.19 (m, 1H), 2.94-2.84 (m, 1H), 2.68 (d, J=4.7 Hz, 3H), 2.48-2.36 (m, 6H), 2.34-2.24 (m, 2H), 1.72-1.64 (m, 4H); 100 MHz $^{13}$C NMR (CDCl$_3$) δ 175.1, 161.2 (d, $J_{C-F}$=245.5 Hz), 146.4, 146.2, 131.4, 122.1 (d, $J_{C-F}$=15.0 Hz), 113.4 (d, $J_{C-F}$=22.8 Hz), 54.0, 52.7, 35.7, 35.4, 32.9, 26.4, 23.5.

Example 48 trans 3-(3-Fluoro-4-pyrrolidin-1-ylmethyl-phenyl)-cyclobutanecarboxylic acid methylamide: R$_f$=0.50 (25% MeOH/CH$_2$Cl$_2$+0.2% NH$_4$OH); LRMS m/z Calcd for C$_{17}$H$_{23}$F N2 O, 290.4, found, 291.1 (M+1) APCI; 400 MHz $^1$HNMR (CDCl$_3$) δ 7.16 (t, J=7.8 Hz, 1H), 6.85-6.74 (m, 2H), 4.03 (bs, 1H), 3.62-3.50 (m, 1H), 3.55 (s, 2H), 3.25 (s, 3H), 2.68-2.40 (m, 7H), 2.24-2.13 (m, 2H), 1.70-1.62 (m, 4H); 100 MHz $^{13}$C NMR (CDCl$_3$) δ 176.7, 161.2 (d, $J_{C-F}$=245.5 Hz), 147.7, 147.6, 131.8, 122.1 (d, $J_{C-F}$=15.0 Hz), 113.2 (d, $J_{C-F}$=22.8 Hz), 53.7, 52.3, 50.0, 35.6, 32.0, 26.4, 23.3.

Example 49

3-(3-Chloro-4-pyrrolidin-1-ylmethyl-phenyl)-3-fluoro-cyclobutanecarboxylic acid methyl-(tetrahydro-pyran-4-ylmethyl)-amide A solution of Example 35, 3-(3-Chloro-4-pyrrolidin-1-ylmethyl-phenyl)-3-hydroxy-cyclobutanecarboxylic acid methyl-(tetrahydro-pyran-4-ylmethyl)-amide (70 mg, 0.17 mmol) in dichloromethane (5 mL) was chilled to −78° C. and added drop wise to a −78° C. chilled solution of BAST (0.034 ml, 0.18 mmol) in dichloromethane (5 ml) under nitrogen. After 1 hr stirring at −78° C., the reaction mixture was poured into saturated aq. NaHCO$_3$ (15 ml) and stirred for 15 min. The layers were separated and after two more extractions of the aqueous phase with CH$_2$Cl$_2$ (2×20 ml), the combined organic extracts were dried over MgSO$_4$ and concentrated under reduced pressure to obtain a residual oil. This was purified by flash column chromatography using a 12 g ISCO™ column and 2% MeOH/CH$_2$Cl$_2$ to recover a mixture of cis/trans isomers of the title compound (40 mg, 57% yield).

R$_f$=0.30 (10% MeOH/CH$_2$Cl$_2$); LRMS m/z Calcd for C$_{23}$H$_{32}$Cl F N2 O2, 422.9, found, 423.4 (M+1) & 403.4 (M+1−HF).

Example 50

3-(3-Chloro-4-pyrrolidin-1-ylmethyl-phenyl)-3-fluoro-cyclobutanecarboxylic acid cyclopropylmethyl-methyl-amide A solution of Example 36, 3-(3-chloro-4-pyrrolidin-1-ylmethyl-phenyl)-3-hydroxy-cyclobutanecarboxylic acid cyclopropylmethyl-methyl-amide (75 mg, 0.20 mmol) in dichloromethane (5 ml) was chilled to −78° C. and added drop wise to a −78° C. chilled solution of BAST (0.074 ml, 0.4 mmol) in dichloromethane (5 ml) under nitrogen. After 1 hr stirring at −78° C., the reaction mixture was poured into saturated aq. NaHCO$_3$ (15 ml) and stirred for 15 min. The layers were separated and after two more extractions of the aqueous phase with CH$_2$Cl$_2$ (2×20 ml), the combined organic extracts were dried over MgSO$_4$ and concentrated under reduced pressure to obtain a residual oil. This was purified by flash column chromatography using a 12 g ISCO™ column and 2% MeOH/CH$_2$Cl$_2$ to recover a mixture of cis/trans isomers of the title compound (75 mg, 99% yield). R$_f$=0.60 (15% MeOH/CH$_2$Cl$_2$); LRMS m/z Calcd for C$_{21}$H$_{28}$Cl F N2 O, 378.9, found, 379.4 (M+1) & 359.4 (M+1−HF)

Example 51

[3-(3-Chloro-4-pyrrolidin-1-ylmethyl-phenyl)-3-fluoro-cyclobutyl]-(2,3-dihydro-5H-benzo[f][1,4] oxazepin-4-yl)-methanone A solution of Example 37, [3-(3-chloro-4-pyrrolidin-1-ylmethyl-phenyl)-3-hydroxy-cyclobutyl]-(2,3-dihydro-5H-benzo[f][1,4]oxazepin-4-yl)-methanone (82 mg, 0.19 mmol) in dichloromethane (5 ml) was chilled to −78° C. and added drop wise to a −78° C. chilled solution of BAST (0.069 ml, 0.37 mmol) in dichloromethane (5 ml) under nitrogen. After 1 hr stirring at −78° C., the reaction mixture was poured into saturated aq. NaHCO$_3$ (15 ml) and stirred for 15 min. The layers were separated and after two more extractions of the aqueous phase with CH$_2$Cl$_2$ (2×20 ml), the combined organic extracts were dried over MgSO$_4$ and concentrated under reduced pressure to obtain a residual oil. This was purified by flash column chromatography using a 12 g ISCO™ column and 2% MeOH/CH$_2$Cl$_2$ to recover a mixture of cis/trans isomers of the title compound (80 mg, 99% yield). R$_f$=0.65 (15% MeOH/CH$_2$Cl$_2$); LRMS m/z Calcd for C$_{25}$H$_{28}$Cl F N2 O2, 442.9, found, 443.9 (M+1) & 423.9 (M+1−HF)

Example 52

3-(3-Chloro-4-pyrrolidin-1-ylmethyl-phenyl)-3-fluoro-cyclobutanecarboxylic acid methyl-(3-methyl-pyridin-2-ylmethyl)-amide A solution of example 38, 3-(3-Chloro-4-pyrrolidin-1-ylmethyl-phenyl)-3-hydroxy-cyclobutanecarboxylic acid methyl-(3-methyl-pyridin-2-ylmethyl)-amide (116 mg, 0.27 mmol) in dichloromethane (5 ml) was chilled to −78° C. and added drop wise to a −78° C. chilled solution of BAST (0.1 ml, 0.54 mmol) in dichloromethane (5 ml) under nitrogen. After 1 hr stirring at −78° C., the reaction mixture was poured into saturated aq. NaHCO$_3$ (15 ml) and stirred for 15 min. The layers were separated and after two more extractions of the aqueous phase with CH$_2$Cl$_2$ (2×20 ml), the combined organic extracts were dried over MgSO$_4$ and concentrated under reduced pressure to obtain a residual oil. This was purified by flash column chromatography using a 12 g ISCO™ column and 2% MeOH/CH$_2$Cl$_2$ to recover the title compound (88 mg, 76% yield).

R$_f$=0.45 (15% MeOH/CH$_2$Cl$_2$); LRMS m/z Calcd for C$_{24}$H$_{29}$ClFN$_3$O, 429.96, found, 430.4 (M+H) APCI; representative $^1$H-NMR peaks: (CDCl$_3$) δ 4.70 (s, 2H), 3.75 (s, 2H), 1.78 (s, 4H).

Intermediate 18a

4-Bromo-2,6-difluorobenzaldehyde n-BuLi (2.7M solution in heptane, 134 mL, 0.36 mol) was added drop wise at ~75° C. to a solution of (i-Pr)$_2$NH (51 ml, 0.36 mol) in THF (300 mL) and the mixture was stirred at the same temperature for 5 min. 1-Bromo-3,5-difluorobenzene (CAS 461-91-1) (70 g, 0.36 mol) in THF (100 ml) was added to the mixture at ~80° C., and the mixture was stirred at the same temperature for 2 h. DMF (28 mL, 0.36 mol) was added to the mixture at ~80° C., and the mixture was stirred at the same temperature for 15 min. A solution of AcOH in Et$_2$O (1:1, 100 ml) was added to attain pH ~4-5 at ~80° C., and the reaction mixture was stirred at RT for 15 min. Water (500 mL) was added, and the layers were separated. The aqueous layer was extracted with Et$_2$O (300 mL). The combined organic phases were washed with water, brine, dried with anhydrous Na$_2$SO$_4$ (100 g), evaporated and recrystallized from hexane to give the title compound (53.5 g, 67%, 0.24 mol) as white crystals. GC/MS data: 219 and 221 (M−H)$^+$; 220 and 222 (M)+ (calculated for C$_7$H$_3$BrF$_2$O 221). 1H NMR data (DMSO-d6): δ 10.15 (s, 1H, CHO), 7.71-7.65 (m, 2H, Ar—H).

Intermediate 18

1-(4-Bromo-2,6-difluorobenzyl)pyrrolidine

Pyrrolidine (25 mL, 0.30 mol) and sodium triacetoxyborohydride (64 g, 0.30 mol) were added in portions to a stirred solution of Intermediate 18a, 4-Bromo-2,6-difluorobenzaldehyde (53.5 g, 0.24 mol) in dichloromethane (500 mL) on ice bath. The reaction mixture was intensively stirred for 12 h at RT. Water (400 mL) was added followed by addition of 5M aq. NaNSO$_4$ to attain pH ~2. The organic layer was separated. The aqueous one was extracted with CH$_2$Cl$_2$ (2×200 mL). The organic layers were discarded. The aqueous fraction was alkalized with K$_2$CO$_3$ to pH ~10, and extracted with CHCl$_3$ (2×300 mL). The organic extract was washed with brine, dried over anhydrous Na$_2$SO$_4$ (100 g) and evaporated in vacuo to give the title compound (52.5 g, 79%, 0.19 mol). LC/MS data: 275.9 and 277.9 (M+H)$^+$ (calculated for C$_{11}$H$_{12}$BrF$_2$N, 276.13). $^1$H NMR data (DMSO-d6): 7.40-7.48 (m, 2H, Ar—H), 3.66 (s, 2H, Ar—CH$_2$), 2.38-2.46 (m, 4H pyrrolidine (CH$_2$)$_2$N), 1.61-1.71 (m, 4H, CH$_2$CH$_2$CH$_2$CH$_2$).

Example 53

[3-(3,5-Difluoro-4-pyrrolidin-1-ylmethyl-phenyl)-3-hydroxy-cyclobutyl]-pyrrolidin-1-yl-methanone A 2.5 M solution of n-BuLi in hexanes (4.34 ml, 10.9 mmol) was added over 15 min to a solution of intermediate 18, 1-(4-bromo-2,6-difluoro-benzyl)-pyrrolidine (3.0 g, 10.9 mmol) in absolute THF (20 ml) under a flow of nitrogen at −78° C. The reaction mixture was stirred at −78° C. for 30 min. Then a −78° C. chilled solution of 3-oxocyclobutanecarboxylic acid (0.62 g, 5.43 mmol) in absolute THF (6 ml) was added drop wise at −78° C. The mixture was warmed to RT slowly and left stirring for 18 hrs. Pyrrolidine (0.674 ml, 8.15 mmol) and T$_3$P (3.8 ml, 5.97 mmol, 50% solution in EtOAc) were added and stirred for 30 min and the reaction was then quenched with 1N NaOH (25 ml) and extracted with CH$_2$Cl$_2$ (3×100 ml) to recover 2.8 g of crude product. This was purified by flash column chromatography using a 120 g ISCO™ column and 5% and 8% MeOH/CH$_2$Cl$_2$ with 0.2% NH$_4$OH to obtain the title compound (520 mg, 26% yield). R$_f$=0.75 (20% MeOH/CH$_2$Cl$_2$+0.2% NH$_4$OH); LRMS m/z Calcd for C$_{20}$H$_{26}$F$_2$N$_2$O$_2$, 364.2, found, 365.4 (M+H) APCI; $^1$H-NMR (CDCl$_3$) δ 7.03 (ddd, J=8.7, 3.7, 2.5 Hz, 2H), 3.76 (s, 2H), 3.51 (t, J=6.8 Hz, 2H), 3.47-3.40 (m, 4H), 3.13-3.06 (m, 1H), 2.80-2.73 (m, 2H), 2.60-2.50 (m, 5H), 2.00-1.90 (m, 2H), 1.90-1.83 (m, 2H), 1.76-1.72 (m, 4H).

Example 54

[3-(3,5-Difluoro-4-pyrrolidin-1-ylmethyl-phenyl)-3-fluoro-cyclobutyl]-pyrrolidin-1-yl-methanone A solution of Example 53, [3-(3,5-Difluoro-4-pyrrolidin-1-ylmethyl-phenyl)-3-hydroxy-cyclobutyl]-pyrrolidin-1-yl-methanone (250 mg, 0.68 mmol) in dichloromethane (5 ml) was chilled to −78° C. and added drop wise to a −78° C. chilled solution of BAST (0.25 ml, 1.37 mmol) in dichloromethane (5 ml) under nitrogen. After 1 hr stirring at −78° C., the reaction mixture was poured into saturated aq. NaHCO$_3$ (20 ml) and stirred for 15 min. The layers were separated and after two more extractions of the aqueous phase with CH$_2$Cl$_2$ (2×50 ml), the combined organic extracts were dried over MgSO$_4$ and concentrated under reduced pressure to obtain a residual oil. This was purified by flash column chromatography using a 12 g ISCO™ column and 2% MeOH/CH$_2$Cl$_2$ to give the title compound (130 mg, 52% yield). R$_f$=0.50 (15% MeOH/CH$_2$Cl$_2$); LRMS m/z Calcd for C$_{20}$H$_{25}$F$_3$N$_2$O, 366.2, found, 367.4 (M+H) APCI; $^1$H-NMR (CDCl$_3$) δ 6.94 (ddd, J=7.9, 4.6, 2.5 Hz, 2H), 3.68 (s, 2H), 3.51-3.25 (m, 5H), 2.84-2.59 (m, 4H), 2.47 (br s, 4H), 1.93-1.84 (m, 2H), 1.83-1.75 (m, 2H), 1.69-1.54 (m, 4H); $^{13}$C-NMR (CDCl$_3$) δ 171.2, 161.9 (dd, J$_{C-F}$=248.7, 9.0 Hz), 144.4-143.9 (multiplet), 113.7-113.4 (multiplet), 107.8 (dd, J$_{C-F}$=27.8, 8.7 Hz), 96.7 (d, J$_{C-F}$=196.1 Hz), 53.4, 46.3, 46.1, 38.4 (d, J$_{C-F}$=24.8 Hz), 31.2, 26.2, 24.4, 23.6.

Example 20

Alternative Preparation 3-(3-Fluoro-4-pyrrolidin-1-ylmethyl-phenyl)-3-hydroxy-cyclobutanecarboxylic acid isobutyl-amide A 2.5 M solution of n-BuLi in hexanes (155 ml, 388 mmol) was added over 30 min to a solution of 1-(4-bromo-2-fluorobenzyl)-pyrrolidine (100 g, 388 mmol) in THF (600 ml) in a 2 L round bottomed flask under a flow of nitrogen at −78° C. The reaction mixture was stirred at −78° C. for 60 min. Then a −78° C. chilled solution of 3-oxocyclobutanecarboxylic acid (22 g, 194 mmol) in THF (264 ml) was cannulated under nitrogen and at −78° C. The mixture was warmed to RT slowly and left stirring for 18 h. Isobutylamine (38.5 mL 388 mmol) and T$_3$P (148 ml, 233 mmol, 50 wt % solution in EtOAc) were added. The mixture was stirred for 60 min and then quenched with 1N NaOH (800 ml) and diluted with another 800 ml of EtOAc. The layers were separated and the aqueous phase was extracted with EtOAc (2×1 L) to recover crude product. This was purified by flash column chromatography using a 75 L Biotage™ column eluting with 100% EtOAc, followed with 25%, 30%, and 40% MeOH/EtOAc. The fractions containing the product were combined and concentrated under reduced pressure to obtain a semi solid which was triturated in Et$_2$O and filtered to obtain the title compound as a white solid (43 g, 61% yield).

Example 55

3-Fluoro-3-(3-fluoro-4-pyrrolidin-1-ylmethyl-phenyl)-cyclobutanecarboxylic acid isobutyl-amide A slurry of Example 20, 3-(3-fluoro-4-pyrrolidin-1-ylmethyl-phenyl)-3-hydroxy-cyclobutanecarboxylic acid isobutyl-amide (32.0 g, 91.8 mmol) in anhydrous THF (1.2 L) was chilled to −78° C. and cannulated into a 2 L round bottomed flask containing a −78° C. chilled solution of BAST (33.8 ml, 183.5 mmol) in anhydrous THF (500 mL) under nitrogen. The resulting reaction slurry was slowly warmed to RT and left stirring for 18 hrs when it turned clear. The reaction mixture was poured into saturated aq. NaHCO$_3$ (1 L) and diluted with 1.5 L of EtOAc and stirred for 30 min. The layers were separated and after two more extractions of the aqueous phase with EtOAc (2×1 L), the combined organic extracts were dried over MgSO$_4$ and concentrated under reduced pressure to obtain a residual oil (35 g). This was purified by flash column chromatography using a 75 L Biotage™ column and CH$_2$Cl$_2$, 5% and 10% MeOH/CH$_2$Cl$_2$ to recover a cis:trans mixture of the title compound (32 g, 91% yield). Cis:trans isomers were separated using Chiralpak™ AS column (10 cm×50 cm) and 90/10 Heptane/IPA with 0.2% diethylamine as an eluent and at a flow rate of 450 ml/min to obtain the title compound (27 g, 85% yield): R$_f$=0.25 (10% MeOH/CH$_2$Cl$_2$); LRMS m/z Calcd for C$_{20}$H$_{28}$F$_2$N$_2$O, 350.2, found, 351.4 (M+H) & 331.4 (M+H−HF) APCI; $^1$H-NMR (CDCl$_3$) δ 7.35 (t, J=7.7 Hz, 1H), 7.18 (d, J=7.9 Hz, 1H), 7.11 (d, J=10.8 Hz, 1H), 5.96 (br s, 1H), 3.63 (s, 2H), 3.27 (p, J=8.5 Hz, 1H), 3.05 (t, J=6.4 Hz, 2H), 2.90-2.77 (m, 2H), 2.72-2.61 (m, 2H), 2.49 (br s, 4H), 1.80-1.67 (m, 5H), 0.86 (d, J=6.6 Hz, 6H); $^{13}$C-NMR (CDCl$_3$) δ 173.9, 161.1, (d, J$_{C-F}$=246.5 Hz), 143.0 (dd, J$_{C-F}$=24.1, 7.1 Hz), 131.5 (d, J=4.5 Hz), 125.9 (d, J$_{C-F}$=14.3 Hz), 120.3 (dd, J$_{C-F}$=7.5, 3.0 Hz), 111.9 (dd, J$_{C-F}$=24.0, 9.0 Hz), 97.2 (d, J$_{C-F}$=193.9 Hz), 54.1, 52.7, 47.22, 38.8 (d, J$_{C-F}$=25.6 Hz), 33.24, 28.7, 23.6, 20.3.

Example 9

Alternative Preparation

[3-Fluoro-3-(3-fluoro-4-pyrrolidin-1-ylmethyl-phenyl)-cyclobutyl]-pyrrolidin-1-yl-methanone Example 56

[3-Fluoro-3-(3-fluoro-4-pyrrolidin-1-ylmethyl-phenyl)-cyclobutyl]-pyrrolidin-1-yl-methanone A solution of Example 8, [3-(3-Fluoro-4-pyrrolidin-1-ylmethyl-phenyl)-3-hydroxy-cyclobutyl]-pyrrolidin-1-yl-methanone (1.2 g, 3.5 mmol) in dichloromethane (10 ml) was chilled to −78° C. and added drop wise to a −78° C. chilled solution of BAST (0.96 ml, 5.2 mmol) in dichloromethane (7.5 ml) under nitrogen. After 1 hr stirring at −78° C., the reaction mixture was poured into saturated aq. NaHCO$_3$ (50 mL) and stirred for 15 min. The layers were separated and after two more extractions of the aqueous phase with CH$_2$Cl$_2$ (2×75 ml), the combined organic extracts were dried over MgSO$_4$ and concentrated under reduced pressure to obtain a residual oil. This was purified by flash column chromatography using a 220 g ISCO™ column and 20% MeOH/EtOAc to recover a mixture of cis/trans isomers of the title compound (660 mg, 54% yield). This was purified using chromatography on a Chiralcel™ OJ (2.1 cm×25 cm) column using 95/5 Heptane/EtOH with 0.1% DEA as an eluent at a flow rate of 20 ml/min to obtain 370 mg of the Example 9 and 45 mg of Example 56.

Example 56

[3-Fluoro-3-(3-fluoro-4-pyrrolidin-1-ylmethyl-phenyl)-cyclobutyl]-pyrrolidin-1-yl-methanone: R$_f$=0.30 (20% MeOH/EtOAc); LRMS m/z Calcd for C$_{20}$H$_{26}$F$_2$N$_2$O, 348.2, found, 349.4 (M+H) & 329.4 (M+H−HF) APCI; $^1$H-NMR (CDCl$_3$) δ 7.43 (t, J=7.7 Hz, 1H), 7.20 (d, J=7.9 Hz, 1H), 7.13 (d, J=10.8 Hz, 1H), 3.68 (s, 2H), 3.46 (t, J=6.8 Hz, 2H), 3.32 (t, J=6.8 Hz, 2H), 3.04-2.93 (m, 2H), 2.79-2.65 (m, 3H), 2.55 (br s, 4H), 1.95-1.88 (m, 2H), 1.86-1.80 (m, 2H), 1.79-1.72 (m, 4H); $^{13}$C-NMR (CDCl$_3$) δ 171.2, 161.26 (d, J$_{C-F}$=247.2 Hz), 143.1-142.8 (multiplet), 131.8 (d, J$_{C-F}$=4.5 Hz), 126.06, 120.4, 112.2 (dd, J$_{C-F}$=24.1, 6.8 Hz), 91.6 (d, J$_{C-F}$=159.3 Hz), 54.19, 52.61, 46.2, 38.5, 38.3, 28.2 (d, J$_{C-F}$=13.5 Hz), 26.2, 24.4, 23.7.

Intermediate 19

(4-Bromo-2-chloro-phenyl)-pyrrolidin-1-yl-methanone

4-Bromo-2-chloro-benzoic acid (30 g, 127.4 mmol) was placed in a 3 L round bottom flask and 1.5 L of EtOAc was transferred into it. Triethylamine (25.8 g, 255 mmol), pyrrolidine (18 g, 255 mmol), and T$_3$P (48.6 g, 152.9 mmol, 50 wt % in EtOAc) were then added. After 1 hr, the reaction was quenched with 200 mL of 1N NaOH and stirred for 10 min. The layers were separated and after 2 more extractions of the aqueous phase with EtOAc (2×500 ml), the combined organic extracts were dried over MgSO$_4$ and filtered. The filtrate was concentrated under reduced pressure to obtain a viscous oil. Flash chromatography using a 330 g ISCO™ column and 50%, 80% EtOAc/Hexanes yielded the title compound as a light yellow colored viscous oil (35.4 g, 96% yield). Rf=0.25 (50% EtOAc/Hexanes), LRMS m/z Calcd for C$_{11}$H$_{11}$BrClNO, 288.6, found, 289.9 (M+H) APCI; $^1$H-NMR (CDCl$_3$) δ 7.56 (d, J=1.7 Hz, 1H), 7.43 (dd, J=1.7, 8.3 Hz, 1H), 7.17 (d, J=8.3 Hz, 1H), 3.63 (b apt t, J=6.6 Hz, 2H), 3.17 (B apt t, J=6.6 Hz, 2H), 2.00-1.84 (m, 4H). $^{13}$C-NMR (CDCl$_3$) δ 166.0, 136.6, 132.6, 131.3, 130.7, 128.9, 123.3, 48.0, 45.8, 26.1, 24.7.

Intermediate 20

1-(4-bromo-2-chlorobenzyl)pyrrolidine

To a dry THF solution (120 ml) of 4-Bromo-2-chlorophenyl)-pyrrolidin-1-yl-methanone (35.3 g, 122.3 mmol) was added drop wise 1.0M BH$_3$/THF (367 ml, 376 mmol) under nitrogen and the resulted reaction mixture was left stirring at rt for 21 hrs. The reaction was quenched with 120 ml of MeOH and heated to 80° C. for 18 hrs. It was then cooled to rt and concentrated under reduced pressure to obtain a residual which was purified by flash chromatography using a 330 g ISCO™ column and 50% EtOAc/hexanes to recover the title compound as a colorless viscous oil (24.4 g, 74% yield). Rf=0.25 (60% EtOAc/Hexanes), LRMS m/z Calcd for C$_{11}$H$_{13}$BrClN, 274.6, found, 276.0 (M+H) APCI; $^1$H-NMR (CDCl$_3$) δ 7.47 (bs, 1H), 7.38-7.33 (m, 2H), 3.66 (s, 2H), 2.58-2.54 (m, 4H), 1.80-1.76 (m, 4H); $^{13}$C-NMR (CDCl$_3$) δ 136.4, 134.8, 132.0, 131.9, 130.0, 120.7, 56.6, 54.4, 23.8.

Intermediate 17

3-(3-chloro-4-((pyrrolidin-1-yl)methyl)phenyl)-3-hydroxycyclobutanecarboxylic acid A 2.5 M solution of n-BuLi in hexanes (60 ml, 150 mmol) was added over 15 min to a solution of intermediate 20, 1-(4-bromo-2-chlorobenzyl)pyrrolidine (41.2 g, 150 mmol) in THF (350 ml) under a flow of nitrogen at −78° C. The reaction mixture was stirred at −78° C. for 30 min. Then a −78° C. chilled solution of 3-oxocyclobutanecarboxylic acid (8.6 g, 75 mmol) in THF (100 ml) was added drop wise for 10 min at −78° C. The mixture was warmed to RT slowly and left stirring for 18 hrs and the resulting solution was used as an intermediate.

Example 57

3-(3-Chloro-4-pyrrolidin-1-ylmethyl-phenyl)-3-hydroxy-cyclobutanecarboxylic acid ethylamide To a crude solution of intermediate 17, 3-(3-chloro-4-((pyrrolidin-1-yl)methyl)phenyl)-3-hydroxycyclobutanecarboxylic acid (~30 mL, ~34.5 mmol) was added 2.0M ethylamine in THF (34.5 mL, 69 mmol) and $T_3P$ (50% solution in EtOAc, 33 ml, 51.8 mmol). The resulting reaction mixture was stirred at RT for 1 hr and then 300 ml of 1N NaOH and 400 ml of EtOAc were added and the layers were separated. The aqueous layer was subjected to EtOAc extraction (2×500 ml) again and the combined organic layers were dried over $MgSO_4$ and evaporated. The residue was purified by flash column chromatography using a 75M Biotage™ column, eluting with a gradient of 5%, 8%, 10%, 15% MeOH/$CH_2Cl_2$ with 0.25% $NH_4OH$. The product containing fractions were collected and concentrated under reduced pressure to give the title compound (4.0 g, 35% yield). Rf=0.40 (15% MeOH/$CH_2Cl_2$+0.2% $NH_4OH$), LRMS m/z Calcd for $C_{18}H_{25}ClN_2O_2$, 336.9, found, 337.4 (M+H) APCI; $^1$H-NMR (CDCl$_3$) δ 7.54 (dd, J=8.3, 2.7 Hz, 1H), 7.49-7.45 (m, 1H), 7.33 (d, J=7.9 Hz, 1H), 6.52-6.35 (br m, 1H), 3.86 (s, 2H), 3.29-3.22 (m, 2H), 2.81-2.60 (m, 7H), 2.48 (d, J=8.3 Hz, 2H), 1.83 (br s, 4H), 1.11 (dt, J=7.3, 2.9 Hz, 3H); $^{13}$C-NMR (CDCl$_3$) δ 176.7, 147.0, 134.2, 133.3, 131.4, 126.5, 123.8, 73.8, 73.9, 56.1, 54.1, 41.2, 35.0, 33.0, 23.6, 14.9.

Example 58

3-(3-Chloro-4-pyrrolidin-1-ylmethyl-phenyl)-3-fluoro-cyclobutanecarboxylic acid ethylamide A solution of Example 57, 3-(3-Chloro-4-pyrrolidin-1-ylmethyl-phenyl)-3-hydroxy-cyclobutanecarboxylic acid ethylamide (52.2 g, 155 mmol) in dichloromethane (400 ml) was chilled to −78° C. and added drop wise to a −78° C. solution of BAST (43 ml, 233 mmol) in dichloromethane (150 ml) under nitrogen. This was slowly warmed to rt and left stirring for 18 hrs after which the reaction mixture was poured into saturated aq. $NaHCO_3$ (1 L) and stirred for 15 min. The layers were separated and after two more extractions of the aqueous phase with $CH_2Cl_2$ (2×1 L), the combined organic extracts were dried over $MgSO_4$ and concentrated under reduced pressure to obtain a residual oil. This was purified by flash column chromatography using a 75 L BiotageBiotage™ column and 5%, 10%, 20% MeOH/EtOAc to recover a mixture of cis/trans isomers of the title compound. This was further purified by chromatography using a Chiralcel™ OD (10 cm×50 cm) column with 93/7 Heptane/IPA as an eluent at a flow rate of 435 ml/min to obtain the title compound (31.7 g, 60% yield): Rf=0.30, (15% MeOH/EtOAc), LRMS m/z Calcd for $C_{18}H_{24}ClFN_2O$, 338.9, found, 339.4 (M+H) APCI; $^1$H-NMR (CDCl$_3$) δ 7.46 (d, J=7.9 Hz, 1H), 7.42 9 s, 1H), 7.32 (dd, J=7.1, 1.5 Hz, 1H), 5.76 (br s, 1H), 3.71 (s, 2H), 3.32-3.20 (m, 3H), 2.92-2.77 (m, 2H), 2.73-2.62 (m, 2H), 2.57-2.52 (m, 4H), 1.80-1.73 (m, 4H), 1.12 (t, J=7.3 Hz, 3H); $^{13}$C-NMR (CDCl$_3$) δ 173.7, 141.8 (d, $J_{C-F}$=23.3 Hz), 137.0, 134.0, 130.7, 125.8 (d, $J_{C-F}$=9.0 Hz), 123.2 (d, $J_{C-F}$=7.5 Hz), 97.2 (d, $J_{C-F}$=194.6 Hz), 56.9, 54.4, 38.7 (d, $J_{C-F}$=24.8 Hz), 34.8, 33.4, 23.8, 15.1. The structure was confirmed by x-ray crystallography and determined to be (1S,3R)—N-ethyl-3-fluoro-3-(3-fluoro-4-(((S)-2-methylpyrrolidin-1-yl)methyl)phenyl)cyclobutanecarboxamide.

Intermediate 21 trans-3-[4-(chloromethyl)-3-fluorophenyl]-N-ethyl-3-fluorocyclobutanecarboxamide Ethylchloroformate (0.505 ml, 5.28 mmol) was added to a solution of Example 16, 3-fluoro-3-(3-fluoro-4-pyrrolidin-1-ylmethyl-phenyl)-cyclobutanecarboxylic acid ethylamide (1.7 g, 5.28 mmol) in DCE (50 ml) After 1 hr stirring at rt, the reaction was quenched with saturated aq.$NaHCO_3$ (150 ml) and extracted with $CH_2Cl_2$ (3×100 ml) to recover a residual oil. This was purified by flash column chromatography using a 120 g ISCO™ cartridge and 35% and 40% EtOAc/hexanes to obtain an intermediate 3-(4-chloromethyl-3-fluoro-phenyl)-3-fluoro-cyclobutanecarboxylic acid ethylamide (1.1 g, 75% yield).

Rf=0.50, (EtOAc/hexanes), LRMS m/z Calcd for $C_{14}H_{16}ClF_2NO$, 287.7, found, 288.3 (M+H) APCI; $^1$H-NMR (CDCl$_3$) δ 7.30 (t, J=7.9 Hz, 1H), 7.18 (d, 1H), 7.12 (dd, J=10.8, 1.2 Hz, 1H), 6.85 (br s, 1H), 4.49 (s, 2H), 3.35-3.26 (m, 1H), 3.25-3.15 (m, 2H), 2.85-2.70 (m, 2H), 2.68-2.52 (m, 2H), 1.03 (t, J=10.9 Hz, 3H); $^{13}$C-NMR (CDCl$_3$) δ 173.9, 160.2 (d, $J_{C-F}$=241.2 Hz), 145.2 (dd, $J_{C-F}$=24.0, 7.8 Hz), 131.1, 124.5, 120.9, 112.4, (dd, $J_{C-F}$=23.3, 9.4 Hz), 96.2 (d, $J_{C-F}$=196.0 Hz), 60.6, 38.8, 34.7, 32.8, 14.8.

Example 59

3-Fluoro-3-[3-fluoro-4-((S)-2-methyl-pyrrolidin-1-ylmethyl)-phenyl]-cyclobutanecarboxylic acid ethylamide To Intermediate 21, trans-3-[4-(chloromethyl)-3-fluorophenyl]-N-ethyl-3-fluorocyclobutanecarboxamide (0.482 g, 1.67 mmol) in DCE (16 ml) was added triethylamine (0.69 ml, 5.01 mmol) and 2-S-methylpyrrolidine hydrobromide (0.56 g, 3.35 mmol). This mixture was heated to 50° C. for 3 hrs. The reaction was cooled to rt and quenched with saturated aq. NaHCO3 (200 ml) and extracted with $CH_2Cl_2$ (3×200 ml) to recover 600 mg of crude material. This was purified by flash column chromatography using a 40 g ISCO™ column and 5% and 10% MeOH/EtOAc to obtain the title compound (400 mg, 71% yield). Rf=0.50 (15% MeOH//EtOAc); LRMS m/z Calcd for $C_{19}H_{26}F_2N_2O$, 336.4, found, 337.2 (M+H) APCI; $^1$H-NMR (CDCl$_3$) δ 7.29 (t, J=7.7 Hz, 1H), 7.13 (d, J=7.9 Hz, 1H), 7.06 (d, J=10.8 Hz, 1H), 6.46 (br s, 1H), 3.86 (d, J=13.3 Hz, 1H), 3.29-3.15 (m, 4H), 2.86-2.71 (m, 3H), 2.66-2.54 (m, 2H), 2.36-2.27 (m, 1H), 2.06 (q, J=8.9 Hz, 1H), 1.87-1.78 (m, 1H), 1.67-1.40 (m, 2H), 1.39-1.29 (m, 1H), 1.09-1.03 (m, 6H); $^{13}$C-NMR (CDCl$_3$) δ 173.9, 161.2 (d, $J_{C-F}$=246.5 Hz), 142.8 (dd, $J_{C-F}$=24.0, 7.5 Hz), 131.7 (d, $J_{C-F}$=4.5 Hz), 126.0 (d, $J_{C-F}$=15.0 Hz), 120.2 (dd, $J_{C-F}$=7.5, 3.0 Hz), 111.8 (dd, $J_{C-F}$=24.0, 9.0 Hz) 97.1 (d, $J_{C-F}$=193.9 Hz), 59.4, 54.0, 50.2, 38.6 (dd, $J_{C-F}$=24.9, 6.4 Hz), 34.7, 33.1, 32.9, 21.7, 19.3, 14.9.

Example 60

3-Fluoro-3-[3-fluoro-4-((R)-2-methyl-pyrrolidin-1-ylmethyl)-phenyl]-cyclobutanecarboxylic acid ethylamide To Intermediate 21, trans-3-[4-(chloromethyl)-3-fluorophenyl]-N-ethyl-3-fluorocyclobutanecarboxamide (0.48 g, 1.67 mmol) in DCE (16 ml) was added triethylamine (0.69 ml, 5.01 mmol) and 2-R-methylpyrrolidine hydrobromide (0.56 g, 3.35 mmol). This mixture was heated to 50° C. for 3 hrs. The reaction was cooled to rt and quenched with saturated aq. NaHCO$_3$ (200 ml) and extracted with CH$_2$Cl$_2$ (3×200 ml) to recover 610 mg of crude material. This was purified by flash column chromatography using a 40 g ISCO™ column and 5% and 10% MeOH/EtOAc to obtain the title compound (406 mg, 72% yield): Rf=0.50 (15% MeOH//EtOAc); LRMS m/z Calcd for C$_{19}$H$_{26}$F$_2$N$_2$O, 336.4, found, 337.2 (M+H) APCI; $^1$H-NMR (CDCl$_3$) δ 7.29 (t, J=7.7 Hz, 1H), 7.12 (d, J=7.9 Hz, 1H), 7.05 (dd, J=10.8, 1.3 Hz, 1H), 6.49 (br t, J=5.0 Hz, 1H), 3.86 (d, J=13.2 Hz, 1H), 3.48-3.15 (m, 4H), 2.86-2.71 (m, 3H), 2.65-2.54 (m, 2H), 2.36-2.27 (m, 1H), 2.05 (q, J=8.7 Hz, 1H), 1.86-1.78 (m, 1H), 1.67-1.40 (m, 2H), 1.38-1.27 (m, 1H), 1.10-1.00 (m, 6H); $^{13}$C-NMR (CDCl$_3$) δ 173.9, 161.2 (d, J$_{C-F}$=246.5 Hz), 142.8 (dd, J$_{C-F}$=23.3, 7.5 Hz), 131.7 (d, J$_{C-F}$=4.5 Hz), 126.0 (d, J$_{C-F}$=15.0 Hz), 120.2 (dd, J$_{C-F}$=7.5, 3.0 Hz), 111.8 (dd, J$_{C-F}$=24.0, 9.0 Hz) 97.1 (d, J$_{C-F}$=194.6 Hz), 59.4, 54.0, 50.2, 38.6 (dd, J$_{C-F}$=25.6, 6.4 Hz), 34.7, 33.0, 32.9, 21.7, 19.3, 14.9.

Example 61

3-(3-Chloro-4-pyrrolidin-1-ylmethyl-phenyl)-3-fluoro-cyclobutanecarboxylic acid dimethylamide To a stirring solution of BAST (0.072 g, 0.327 mmol) at −78° C. in dry CH$_2$Cl$_2$ (2 ml) was added a solution of Example 31, 3-(3-Chloro-4-pyrrolidin-1-ylmethyl-phenyl)-3-hydroxy-cyclobutanecarboxylic acid dimethylamide (0.1 g, 0.296 mmol) in dry CH$_2$Cl$_2$ (5 ml) drop wise. After 1 hr, the reaction was quenched cold with sat. aq. NaHCO$_3$ (10 ml) and diluted with CH$_2$Cl$_2$. The layers were separated and the aqueous phase was once again extracted with CH$_2$Cl$_2$ (25 ml) and the combined organic phases were dried over MgSO$_4$ and concentrated under reduced pressure to obtain a residual oil. This was purified by flash chromatography using a 10 g ISCO™ column and 2.5% MeOH/CH$_2$Cl$_2$ to obtain the title compound (56 mg, 56% yield). Rf=0.30, (10% MeOH/CH$_2$Cl$_2$); LRMS m/z Calcd for C$_{18}$H$_{24}$ClFN$_2$O, 338.9, found, 339.4 (M+H), 319.4 (M+H–HF) APCI; $^1$H-NMR (CDCl$_3$) δ 7.46 (d, J=7.9 Hz, 1H), 7.39 (bs, 1H), 7.28 (m, 1H), 3.72 (s, 2H), 3.68-3.57 (m, 1H), 2.97 (s, 3H), 2.95 (s, 3H), 2.96-2.66 (m, 4H), 2.60-2.52 (m, 4H), 1.82-1.74 (m, 4H); $^{13}$C-NMR (CDCl$_3$) δ 173.3, 141.8 (d, J$_{C-F}$=23.5 Hz), 137.0, 134.0, 130.7, 125.8 (d, J$_{C-F}$=8.3 Hz), 123.2 (d, J$_{C-F}$=8.0 Hz), 97.5 (d, J$_{C-F}$=194.0 Hz), 56.9, 54.4, 38.6, 38.4 36.9, 35.8, 30.1 23.8.

Where cis and trans isomers are possible for an embodiment of the inventive compound of formula I, both cis and trans isomers are within the scope of the invention. Rotomers are possible for an embodiment of the inventive compound of formula I and are within the scope of the invention.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula I contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E. L. Eliel (Wiley, New York, 1994).

The composition of the present invention may be formulated in a conventional manner using one or more pharmaceutically acceptable carriers. The composition may be formulated for oral, buccal, intranasal, parenteral (e.g., intravenous, intramuscular, intraperitoneal, or subcutaneous or through an implant) nasal, vaginal, sublingual, rectal or topical administration or in a form suitable for administration by inhalation or insufflation.

Pharmaceutically acceptable salts of compounds of formula I may be prepared by one or more of three methods: (i) by reacting the compound of formula I with the desired acid or base; (ii) by removing an acid- or base-labile protecting group from a suitable precursor of the compound of formula I or by ring-opening a suitable cyclic precursor, for example, a lactone or lactam, using the desired acid or base; or (iii) by converting one salt of the compound of formula I to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

Also included within the scope of the invention are metabolites of compounds of formula I, that is, compounds formed in vivo upon administration of the drug. Some examples of metabolites in accordance with the invention include: (i) where the compound of formula (I) contains a methyl group, an hydroxymethyl derivative thereof (—CH$_3$→—CH$_2$OH); (ii) where the compound of formula (I) contains an alkoxy group, an hydroxy derivative thereof (—OR→—OH); (iii) where the compound of formula (I) contains a tertiary amino group, a secondary amino derivative thereof (—NR$^a$R$^b$→—NHR$^a$ or —NHR$^b$); (iv) where the compound of formula (I) contains a secondary amino group, a primary derivative thereof (—NHR$^a$→—NH$_2$); (v) where the compound of formula (I) contains an amide group, a carboxylic acid derivative thereof (—CONR$^c$R$^d$→COOH).

Isotopically labeled compounds of formula I of this invention can generally be prepared by carrying out the procedures disclosed in the preceeding Schemes and/or in the Examples and Preparations, by substituting a readily available isotopically labeled reagent for a non-isotopically labeled reagent.

For oral administration, the pharmaceutical composition may take the form of, for example, tablets or capsules prepared by conventional means with pharmaceutically acceptable excipients such as binding agents such as pregelatinized maize starch, polyvinylpyrrolidone or hydroxypropyl methylcellulose; fillers such as lactose, microcrystalline cellulose or calcium phosphate; lubricants such as magnesium stearate, talc or silica; disintegrants such as potato starch or sodium starch glycolate; or wetting agents such as sodium lauryl sulphate. The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents such as sorbitol syrup, methyl cellulose or hydrogenated edible fats; emulsifying agents such as lecithin or acacia, non-aqueous vehicles such as almond oil, oily esters or ethyl alcohol; and preservatives such as methyl or propyl p-hydroxybenzoates or sorbic acid.

For buccal administration, the composition may take the form of tablets or lozenges formulated in conventional manner.

The composition of the invention may be formulated for parenteral administration by injection, including using conventional catheterization techniques or infusion. Formulations for injection may be presented in unit dosage form, for example, in ampoules or in multi-dose containers, with an added preservative. The composition may take such forms as suspensions, solutions or emulsions in oily or aqueous vehicles, and may contain formulating agents such as suspending, stabilizing and/or dispersing agents. Alternatively, the active ingredient or ingredients in a composition may be in powder form for reconstitution with a suitable vehicle, for example, sterile pyrogen-free water, before use. The term "active ingredient" as used herein refers to a compound of the formula I, a histamine $H_1$ antagonist, or a neurotransmitter re-uptake blocker.

The composition of the invention may also be formulated in a rectal composition such as suppositories or retention enemas, for example, containing conventional suppository bases such as cocoa butter or other glycerides. A composition for vaginal administration is preferably a suppository that may contain, in addition to the active ingredient or ingredients, excipients such as cocoa butter or a suppository wax. A composition for nasal or sublingual administration is also prepared with standard excipients well known in the art.

For intranasal administration or administration by inhalation, the composition may be conveniently delivered in the form of a solution or suspension from a pump spray container that is squeezed or pumped by the patient or as an aerosol spray presentation from a pressurized container or a nebulizer, with the use of a suitable propellant, for example, dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active ingredient or ingredients. Capsules and cartridges, made, for example, from gelatin, for use in an inhaler or insufflator may be formulated containing a powder mix of an active ingredient or ingredients and a suitable powder base such as lactose or starch. The active ingredient or ingredients in the composition may range in size from nanoparticles to microparticles.

An exemplary dose of the composition of the invention comprising a compound of formula I for oral, parenteral or buccal administration to the average adult human for the treatment of the conditions referred to herein is about 0.01 to about 1000 mg of the compound of formula I per unit dose which could be administered, for example, 1 to 3 times per day.

An exemplary dose of the composition of the invention comprising a compound of formula I and a histamine $H_1$ antagonist or a neurotransmitter re-uptake blocker for oral, parenteral or buccal administration to the average adult human for the treatment of the conditions referred to herein is about 0.01 to about 500 mg of the compound of formula I and of about 0.01 mg to about 500 mg of the histamine $H_1$ antagonist or the neurotransmitter re-uptake blocker per unit dose which could be administered, for example, 1 to 3 times per day.

Aerosol formulations for treatment of the conditions referred to herein in the average adult human are preferably arranged so that each metered dose or "puff" of aerosol contains about 20 µg to about 1000 µg of the compound of formula I. The overall daily dose with an aerosol will be within the range about 100 µg to about 10 mg. Administration may be several times daily, for example 2, 3, 4 or 8 times, giving for example, 1, 2 or 3 doses each time. Aerosol formulations containing a compound of formula I and a histamine $H_1$ antagonist or a neurotransmitter re-uptake blocker are preferably arranged so that each metered dose or "puff" of aerosol contains about 100 µg to about 10,000 µg of the compound of formula I and about 100 µg to about 30,000 µg of the histamine $H_1$ antagonist or the neurotransmitter re-uptake blocker. Administration may be several times daily, for example 1, 3, 4 or 8 times, giving for example, 1, 2 or 3 doses each time. The composition of the invention comprising a compound of formula I and a histamine $H_1$ antagonist or a neurotransmitter re-uptake blocker may optionally contain a pharmaceutically acceptable carrier and may be administered in both single and multiple dosages as a variety of different dosage forms, such as tablets, capsules, lozenges, troches, hard candies, powders, sprays, aqueous suspension, injectable solutions, elixirs, syrups, and the like. The pharmaceutically acceptable carriers include solid diluents or fillers, sterile aqueous media and various non-toxic organic solvents, etc. Oral pharmaceutical formulations can be suitably sweetened and/or flavored by means of various agents of the type commonly employed for such purposes. In general, the compound of formula I is present in such dosage forms at concentration levels ranging from about 0.1% to about 99.9% by weight of the total composition, i.e., in amounts which are sufficient to provide the desired unit dosage, and the histamine $H_1$ antagonist or the neurotransmitter re-uptake blocker is present in such dosage forms at concentration levels ranging from about 0.1% to about 99.9% by weight of the total composition, i.e., in amounts which are sufficient to provide the desired unit dosage.

The compound of formula I and the histamine $H_1$ antagonist may be administered together or separately. When administered separately, the compound of formula I and the histamine $H_1$ antagonist may be administered in either order, provided that after administration of the first of the two active ingredients, the second active ingredient is administered within 24 hours or less, preferably 12 hours or less.

The compound of formula I and the neurotransmitter re-uptake blocker may be administered together or separately. When administered separately, the compound of formula I and the neurotransmitter re-uptake blocker may be administered in either order, provided that after administration of the first of the two active ingredients, the second active ingredient is administered within 24 hours or less, preferably 12 hours or less.

A preferred dose ratio of compound of formula I to the histamine $H_1$ antagonist or to the neurotransmitter re-uptake blocker for oral, parenteral or buccal administration to the average adult human for the treatment of the conditions referred to herein is from about 0.001 to about 1000, preferably from about 0.01 to about 100.

The composition may be homogeneous, wherein by homogeneous it is meant that the active ingredient or ingredients are dispersed evenly throughout the composition so that the composition may be readily subdivided into equally effective unit dosage forms such as tablets, pills and capsules. This solid composition is then subdivided into unit dosage forms of the type described herein containing from about 0.1 to about 1000 mg of the active ingredient or ingredients. Typical unit dosage forms contain from about 1 to about 300 mg, for example about 1, 2, 5, 10, 25, 50 or 100 mg, of the active ingredient or ingredients. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The dosage of the active ingredient or ingredients in the composition and methods of this invention may be varied; however, it is necessary that the amount of the active ingredient or ingredients in such a composition be such that a suitable dosage form is obtained. The selected dosage depends upon the desired therapeutic effect, on the route of administration, the particular compounds administered, the duration of the treatment, and other factors. All dosage ranges and dosage levels mentioned herein refer to each active ingredient present in the pharmaceutical composition of the present invention, as well as those used in the methods of the present invention. Generally, dosage levels of between about 0.01 and about 100 mg/kg of body weight daily are administered to humans and other mammals. A preferred dosage range in humans is about 0.1 to about 50 mg/kg of body weight daily which can be administered as a single dose or divided into multiple doses. A preferred dosage range in mammals other than humans is about 0.01 to about 10.0 mg/kg of body weight daily which can be administered as a single dose or divided into multiple doses. A more preferred dosage range in mammals other than humans is about 0.1 to about 5.0 mg/kg of body weight daily which can be administered as a single dose or divided into multiple doses.

The pharmaceutical composition comprising the compound of formula I and the histamine $H_1$ antagonist or the neurotransmitter re-uptake blocker may be administered at dosages of a therapeutically effective amount of the compound of formula I and of the second active ingredient in single or divided doses.

The specific therapeutically effective dose level for any particular patient will depend upon a variety of factors including the disorder being treated and the severity of the disorder; activity of the specific compound employed; the specific composition employed; the age. However, some variation in dosage will necessarily occur depending upon the condition of the subject being treated. The person responsible for administration will, in any event, determine the appropriate dose for the individual subject.

The dosage amounts set forth in this description and in the appended claims may be used, for example, for an average human subject having a weight of about 65 kg to about 70 kg. The skilled practitioner will readily be able to determine any variation in the dosage amount that may be required for a subject whose weight falls outside the about 65 kg to about 70 kg range, based upon the medical history of the subject. The pharmaceutical combinations may be administered on a regimen of up to 6 times per day, preferably 1 to 3 times per day, such as 2 times per day or once daily.

Determination of Biological Activity

The in vitro affinity of the compounds in the present invention at the rat or human histamine H3 receptors can be determined according to the following procedure. Frozen rat frontal brain or frozen human post-mortem frontal brain is homogenized in 20 volumes of cold 50 mM Tris HCl containing 2 mM $MgCl_2$ (pH to 7.4 at 4° C.). The homogenate is then centrifuged at 45,000 G for 10 minutes. The supernatant is decanted and the membrane pellet resuspended by Polytron in cold 50 mM Tris HCl containing 2 mM MgCl2 (pH to 7.4 at 4° C.) and centrifuged again. The final pellet is resuspended in 50 mM Tris HCl containing 2 mM MgCl2 (pH to 7.4 at 25° C.) at a concentration of 12 mg/mL. Dilutions of compounds are made in 10% DMSO/50 mM Tris buffer (pH 7.4) (at 10× final concentration, so that the final DMSO concentration is 1%). Incubations are initiated by the addition of membranes (200 microliters) to 96 well V-bottom polypropylene plates containing 25 microliters of drug dilutions and 25 microliters of radioligand (1 nM final concentration 3H—N-methyl-histamine). After a 1 hour incubation, assay samples are rapidly filtered through Whatman GF/B filters and rinsed with ice-cold 50 mM Tris buffer (pH 7.4) using a Skatron cell harvester. Radioactivity is quantified using a BetaPlate scintillation counter. The percent inhibition of specific binding can then be calculated.

A person of ordinary skill in the art could adapt the above procedure to other assays.

TABLE 1

| Rat Histamine H3 Receptor Binding | |
|---|---|
| Example # | rH3 $K_i$ (nM) |
| 9 | 18.9 |
| 11 | 24.1 |
| 13 | 10.1 |
| 15 | 44.1 |
| 16 | 20.7 |
| 23 | 28.8 |
| 46 | 10.9 |
| 50 | 32.3 |
| 55 | 10.1 |
| 59 | 21.4 |

We claim:
1. A compound of formula I

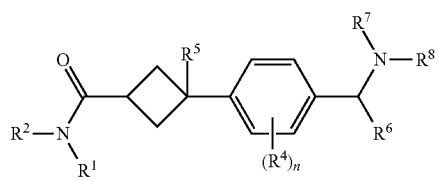

the stereoisomers, geometric isomers, or tautomeric forms of the compound of Formula I thereof, or a pharmaceutically acceptable salt thereof,
wherein:
$R^1$ and $R^2$ are each independently selected from the group consisting of hydrogen;
$C_1$-$C_8$ alkyl optionally substituted with 1 to 4 halogens;
$C_1$-$C_4$ alkyl group optionally substituted with a substituent selected from the group consisting of OH, one to four $C_1$-$C_4$ alkyl, $C_3$-$C_7$ cycloalkyl, $C_1$-$C_4$ dialkylamino, $C_6$-$C_{14}$ aryl optionally substituted with a halogen and optionally substituted with $C_6$-$C_{10}$ aryloxy optionally substituted with one to two halogens, and 5-10-membered heteroaryl optionally substituted with a $C_6$-$C_{10}$ aryl group and optionally substituted with one to three $C_1$-$C_4$ alkyl groups;

$C_3$-$C_7$ cycloalkyl;

$C_6$-$C_{14}$ aryl;

-($C_0$-$C_3$)alkyl-O-($C_1$-$C_3$)alkyl optionally substituted with ($C_1$-$C_3$)alkyl;

-($C_1$-$C_3$)alkyl-C(=O)O—($C_1$-$C_3$)alkyl;

3-8-membered heterocycloalkyl optionally substituted with one or more $C_1$-$C_4$ alkyl-carbonyl groups;

$C_6$-$C_{10}$ arylsulfonyl optionally substituted with one or more $C_1$-$C_2$ alkyl;

5-10-membered heteroaryl; and $C_6$-$C_{14}$ aryl-$C_0$-$C_4$ alkylene-O-$C_0$-$C_4$ alkyl, wherein each $C_0$-$C_4$ alkyl and each $C_0$-$C_4$ alkylene is optionally substituted with one to four $C_1$-$C_4$ alkyl;

or optionally $R^1$ and $R^2$, together with the nitrogen to which they are attached, form a 4-, 5-, 6-, or 7-membered saturated or unsaturated aliphatic ring, wherein one of the carbons in said aliphatic ring is optionally replaced by O, S, $NR^3$, or CO, and wherein said ring is optionally fused to a $C_6$-$C_{10}$ arylene and is optionally substituted at a ring carbon with a substituent selected from the group consisting of —OH, 5-10-membered heteroaryl optionally substituted with one or more halogens and optionally substituted with one or more $C_1$-$C_2$ alkyl, $C_1$-$C_4$ alkoxy optionally substituted with one or more $C_1$-$C_2$ alkoxy and optionally substituted with one or more $C_1$-$C_4$ dialkylaminocarbonyl, and one or two $C_1$-$C_4$ alkyl optionally and independently substituted with one or more $C_1$-$C_2$ alkoxy;

wherein $R^3$ is hydrogen;

$C_1$-$C_8$ alkyl optionally substituted with 1 to 4 halogens;

5-10-membered heteroaryl optionally substituted with a substituent selected from the group consisting of halogen, $C_1$-$C_4$ alkyl, $C_1$-$C_2$ alkoxy, $C_6$-$C_{10}$ aryl, $C_1$-$C_4$ alkylaminocarbonyl, and cyano;

$C_1$-$C_4$ alkyl group optionally substituted with a substituent selected from the group consisting of $C_1$-$C_2$ alkoxycarbonyl, 5-10-membered heteroaryl optionally substituted with one or more $C_1$-$C_2$ alkyl, one to four $C_1$-$C_4$ alkyl, $C_3$-$C_7$ cycloalkyl, and $C_6$-$C_{14}$ aryl;

$C_6$-$C_{10}$ aryl optionally substituted with one or two $C_1$-$C_2$ alkyl;

$C_1$-$C_4$ alkylcarbonyl;

or $C_6$-$C_{14}$ aryl-$C_0$-$C_4$ alkylene-O-$C_0$-$C_4$ alkyl, wherein each $C_0$-$C_4$ alkyl and each $C_0$-$C_4$ alkylene is optionally substituted with one to four $C_1$-$C_4$ alkyl;

$R^4$ is independently selected from the group consisting of hydrogen, $C_1$-$C_4$ alkyl, $C_1$-$C_4$ alkoxyl, halogen, nitrile, —$SO_2C_1$-$C_4$, —$SO_2NHC_1$-$C_4$, and —C(=O)$NHC_1$-$C_4$;

n is 0, 1, 2, 3, or 4;

$R^5$ is OH, —O($C_1$-$C_3$)alkyl, halogen or hydrogen;

$R^6$ is hydrogen, $C_1$-$C_4$ alkyl optionally substituted with 1 to 4 halogens, or $C_3$-$C_7$ cycloalkyl-$C_0$-$C_4$ alkyl;

$R^7$ is hydrogen, $C_1$-$C_8$ alkyl optionally substituted with 1 to 4 halogens, or $C_3$-$C_7$ cycloalkyl-$C_0$-$C_4$ alkyl, wherein each $C_0$-$C_4$ is optionally substituted with one to four $C_1$-$C_4$ alkyl and;

$R^8$ is hydrogen, $C_1$-$C_8$ alkyl optionally substituted with 1 to 4 halogens, or $C_3$-$C_7$ cycloalkyl-$C_0$-$C_4$ alkyl;

or optionally $R^7$ and $R^8$, together with the nitrogen to which they are attached, form a 4-, 5-, 6-, or 7-membered heterocyclic ring, wherein said heterocyclic ring is optionally substituted with one or two $C_1$-$C_4$ alkyl; and wherein one of the carbons of said heterocyclic ring that is separated by at least two atoms from said nitrogen in said heterocyclic ring is optionally replaced by O, S, $NR^9$, or C=O, wherein $R^9$ is hydrogen, $C_1$-$C_8$ alkyl optionally substituted with 1 to 4 halogens, or $C_3$-$C_7$ cycloalkyl-$C_0$-$C_4$ alkyl, and wherein each $C_0$-$C_4$ alkyl is optionally substituted with one to four $C_1$-$C_4$ alkyl.

2. A compound of formula I, according to claim 1, or a pharmaceutically acceptable salt thereof wherein $R^7$ and $R^8$, together with the nitrogen to which they are attached, form a 4-, 5-, 6- or 7-membered heterocyclic ring, wherein said heterocyclic ring is optionally substituted with one or two $C_1$-$C_4$ alkyl; and wherein one of the carbons of said heterocyclic ring that is separated by at least two atoms from said nitrogen in said heterocyclic ring is optionally replaced by O, S, $NR^9$, or C=O, wherein $R^9$ is hydrogen, $C_1$-$C_8$ alkyl optionally substituted with 1 to 4 halogens, or $C_3$-$C_7$ cycloalkyl-$C_0$-$C_4$ alkyl, and wherein each $C_0$-$C_4$ alkyl is optionally substituted with one to four $C_1$-$C_4$ alkyl.

3. A compound of formula I, according to claim 2, or a pharmaceutically acceptable salt thereof wherein $R^7$ and $R^8$, together with the nitrogen to which they are attached, form a 5- or 6-membered saturated heterocycle.

4. A compound of formula I, according to claim 3, or a pharmaceutically acceptable salt thereof wherein said saturated heterocycle is a pyrrolidinyl group.

5. A compound of formula I, according to claim 2, or a pharmaceutically acceptable salt thereof wherein $R^1$ is hydrogen; $R^4$ and $R^5$ are independently hydrogen or F; $R^6$ is hydrogen or $C_1$-$C_6$ alkyl.

6. A compound of formula I, according to claim 1, or a pharmaceutically acceptable salt thereof wherein $R^5$ is H.

7. A compound of formula I, according to claim 1, or a pharmaceutically acceptable salt thereof wherein $R^5$ is F.

8. A compound of formula I, according to claim 2, or a pharmaceutically acceptable salt thereof wherein $R^5$ is H.

9. A compound of formula I, according to claim 2, or a pharmaceutically acceptable salt thereof wherein $R^5$ is F.

10. A cis cyclobutyl isomer of formula I, according to claim 1, or a pharmaceutically acceptable salt thereof.

11. A trans cyclobutyl isomer of formula I, according to claim 1, or a pharmaceutically acceptable salt thereof.

12. A cis cyclobutyl isomer of formula I, according to claim 2, or a pharmaceutically acceptable salt thereof.

13. A trans cyclobutyl isomer of formula I, according to claim 2, or a pharmaceutically acceptable salt thereof.

14. A compound of formula I, or a pharmaceutically acceptable salt thereof, according to claim 1, wherein the compound is selected from the group consisting of:

cis-3-(3-Fluoro-4-pyrrolidin-1-ylmethyl-phenyl)-cyclobutanecarboxylic acid dimethylamide;

cis-[3-(3-Fluoro-4-pyrrolidin-1-ylmethyl-phenyl)-cyclobutyl]-pyrrolidin-1-yl-methanone;

cis-3-(3-Fluoro-4-pyrrolidin-1-ylmethyl-phenyl)-cyclobutanecarboxylic acid ethyl-methyl-amide;

cis-3-(3-Chloro-4-pyrrolidin-1-ylmethyl-phenyl)-cyclobutanecarboxylic acid methylamide;

cis-3-(3-Fluoro-4-pyrrolidin-1-ylmethyl-phenyl)-cyclobutanecarboxylic acid methylamide;

cis-{3-[3-Chloro-4-((R)-2-methyl-pyrrolidin-1-ylmethyl)-phenyl]-cyclobutyl}-pyrrolidin-1-yl-methanone;

cis-3-(2,3-Dichloro-4-pyrrolidin-1-ylmethyl-phenyl)-cyclobutanecarboxylic acid dimethylamide;

cis-3-(3-Fluoro-4-pyrrolidin-1-ylmethyl-phenyl)-cyclobutanecarboxylic acid ethylamide;
cis-3-(3-Fluoro-4-pyrrolidin-1-ylmethyl-phenyl)-cyclobutanecarboxylic acid isobutyl-amide;
cis-(3-Aza-bicyclo[3.2.2]non-3-yl)-[3-(3-fluoro-4-pyrrolidin-1-ylmethyl-phenyl)-cyclobutyl]-methanone;
trans-3-(3-Fluoro-4-pyrrolidin-1-ylmethyl-phenyl)-cyclobutanecarboxylic acid dimethylamide;
trans-[3-(3-Fluoro-4-pyrrolidin-1-ylmethyl-phenyl)-cyclobutyl]-pyrrolidin-1-yl-methanone;
trans-3-(3-Fluoro-4-pyrrolidin-1-ylmethyl-phenyl)-cyclobutanecarboxylic acid ethyl-methyl-amide;
trans-3-(3-Chloro-4-pyrrolidin-1-ylmethyl-phenyl)-cyclobutanecarboxylic acid methylamide;
trans-3-(3-Fluoro-4-pyrrolidin-1-ylmethyl-phenyl)-cyclobutanecarboxylic acid methylamide;
trans-{3-[3-Chloro-4-((R)-2-methyl-pyrrolidin-1-ylmethyl)-phenyl]-cyclobutyl}-pyrrolidin-1-yl-methanone;
trans-3-(2,3-Dichloro-4-pyrrolidin-1-ylmethyl-phenyl)-cyclobutanecarboxylic acid dimethylamide;
trans-3-(3-Fluoro-4-pyrrolidin-1-ylmethyl-phenyl)-cyclobutanecarboxylic acid ethylamide;
trans-3-(3-Fluoro-4-pyrrolidin-1-ylmethyl-phenyl)-cyclobutanecarboxylic acid isobutyl-amide; and
trans-(3-Aza-bicyclo[3.2.2]non-3-yl)-[3-(3-fluoro-4-pyrrolidin-1-ylmethyl-phenyl)-cyclobutyl]-methanone.

15. A compound of formula I, or a pharmaceutically acceptable salt thereof, according to claim 1, wherein the compound is selected from the group consisting of:
cis-[3-Fluoro-3-(3-fluoro-4-pyrrolidin-1-ylmethyl-phenyl)-cyclobutyl]-pyrrolidin-1-yl-methanone;
cis-3-(3-Chloro-4-pyrrolidin-1-ylmethyl-phenyl)-3-fluoro-cyclobutanecarboxylic acid dimethylamide;
cis-[3-(3-Chloro-4-pyrrolidin-1-ylmethyl-phenyl)-3-fluoro-cyclobutyl]-piperidin-1-yl-methanone;
cis-3-(3-Chloro-4-pyrrolidin-1-ylmethyl-phenyl)-3-fluoro-cyclobutanecarboxylic acid isobutyl-methyl-amide;
cis-3-(3-Chloro-4-pyrrolidin-1-ylmethyl-phenyl)-3-fluoro-cyclobutanecarboxylic acid cyclopropylmethyl-amide;
cis-[3-(3,5-Difluoro-4-pyrrolidin-1-ylmethyl-phenyl)-3-fluoro-cyclobutyl]-pyrrolidin-1-yl-methanone;
cis-3-(2,6-Difluoro-4-pyrrolidin-1-ylmethyl-phenyl)-3-fluoro-cyclobutanecarboxylic acid methylamide;
cis-3-(5-Chloro-2-fluoro-4-pyrrolidin-1-ylmethyl-phenyl)-3-fluoro-cyclobutanecarboxylic acid isobutyl-amide;
cis-3-(3-Chloro-4-pyrrolidin-1-ylmethyl-phenyl)-3-fluoro-cyclobutanecarboxylic acid ethylamide;
cis-3-(3-Chloro-4-pyrrolidin-1-ylmethyl-phenyl)-3-fluoro-cyclobutanecarboxylic acid methyl-(tetrahydropyran-4-ylmethyl)-amide;
cis-3-Fluoro-3-(3-fluoro-4-pyrrolidin-1-ylmethyl-phenyl)-cyclobutanecarboxylic acid methylamide;
cis-{3-[3-Chloro-4-((R)-2-methyl-pyrrolidin-1-ylmethyl)-phenyl]-3-fluoro-cyclobutyl}-pyrrolidin-1-yl-methanone;
cis-3-(3-Chloro-4-pyrrolidin-1-ylmethyl-phenyl)-3-fluoro-cyclobutanecarboxylic acid cyclopropylmethyl-methyl-amide;
cis-3-Fluoro-3-(3-fluoro-4-pyrrolidin-1-ylmethyl-phenyl)-cyclobutanecarboxylic acid dimethylamide;
cis-3-Fluoro-3-[3-fluoro-4-((S)-2-methyl-pyrrolidin-1-ylmethyl)-phenyl]-cyclobutanecarboxylic acid ethylamide;
cis-[3-(3-Chloro-4-pyrrolidin-1-ylmethyl-phenyl)-3-fluoro-cyclobutyl]-(2,3-dihydro-5H-benzo[f][1,4]oxazepin-4-yl)-methanone;
cis-3-Fluoro-3-(3-fluoro-4-pyrrolidin-1-ylmethyl-phenyl)-cyclobutanecarboxylic acid ethylamide;
cis-3-Fluoro-3-(3-fluoro-4-pyrrolidin-1-ylmethyl-phenyl)-cyclobutanecarboxylic acid ethyl-methyl-amide;
cis-3-(3-Chloro-4-pyrrolidin-1-ylmethyl-phenyl)-3-fluoro-cyclobutanecarboxylic acid methyl-(3-methyl-pyridin-2-ylmethyl)-amide;
cis-3-Fluoro-3-[3-fluoro-4-((R)-2-methyl-pyrrolidin-1-ylmethyl)-phenyl]-cyclobutanecarboxylic acid ethylamide;
cis-3-Fluoro-3-(3-fluoro-4-pyrrolidin-1-ylmethyl-phenyl)-cyclobutanecarboxylic acid isobutyl-amide;
cis-[3-Fluoro-3-(3-fluoro-4-pyrrolidin-1-ylmethyl-phenyl)-cyclobutyl]-pyrrolidin-1-yl-methanone;
cis-[3-Fluoro-3-(3-fluoro-4-pyrrolidin-1-ylmethyl-phenyl)-cyclobutyl]-pyrrolidin-1-yl-methanone;
cis-3-(2,3-Dichloro-4-pyrrolidin-1-ylmethyl-phenyl)-3-fluoro-cyclobutanecarboxylic acid dimethylamide;
trans-[3-Fluoro-3-(3-fluoro-4-pyrrolidin-1-ylmethyl-phenyl)-cyclobutyl]-pyrrolidin-1-yl-methanone;
trans-3-(3-Chloro-4-pyrrolidin-1-ylmethyl-phenyl)-3-fluoro-cyclobutanecarboxylic acid dimethylamide;
trans-[3-(3-Chloro-4-pyrrolidin-1-ylmethyl-phenyl)-3-fluoro-cyclobutyl]-piperidin-1-yl-methanone;
trans-3-(3-Chloro-4-pyrrolidin-1-ylmethyl-phenyl)-3-fluoro-cyclobutanecarboxylic acid isobutyl-methyl-amide;
trans-3-(3-Chloro-4-pyrrolidin-1-ylmethyl-phenyl)-3-fluoro-cyclobutanecarboxylic acid cyclopropylmethyl-amide;
trans-[3-(3,5-Difluoro-4-pyrrolidin-1-ylmethyl-phenyl)-3-fluoro-cyclobutyl]-pyrrolidin-1-yl-methanone;
trans-3-(2,6-Difluoro-4-pyrrolidin-1-ylmethyl-phenyl)-3-fluoro-cyclobutanecarboxylic acid methylamide;
trans-3-(5-Chloro-2-fluoro-4-pyrrolidin-1-ylmethyl-phenyl)-3-fluoro-cyclobutanecarboxylic acid isobutyl-amide;
trans-3-(3-Chloro-4-pyrrolidin-1-ylmethyl-phenyl)-3-fluoro-cyclobutanecarboxylic acid ethylamide;
trans-3-(3-Chloro-4-pyrrolidin-1-ylmethyl-phenyl)-3-fluoro-cyclobutanecarboxylic acid methyl-(tetrahydropyran-4-ylmethyl)-amide;
trans-3-Fluoro-3-(3-fluoro-4-pyrrolidin-1-ylmethyl-phenyl)-cyclobutanecarboxylic acid methylamide;
trans-{3-[3-Chloro-4-((R)-2-methyl-pyrrolidin-1-ylmethyl)-phenyl]-3-fluoro-cyclobutyl}-pyrrolidin-1-yl-methanone;
trans-3-(3-Chloro-4-pyrrolidin-1-ylmethyl-phenyl)-3-fluoro-cyclobutanecarboxylic acid cyclopropylmethyl-methyl-amide;
trans-3-Fluoro-3-(3-fluoro-4-pyrrolidin-1-ylmethyl-phenyl)-cyclobutanecarboxylic acid dimethylamide;
trans-3-Fluoro-3-[3-fluoro-4-((S)-2-methyl-pyrrolidin-1-ylmethyl)-phenyl]-cyclobutanecarboxylic acid ethylamide;
trans-[3-(3-Chloro-4-pyrrolidin-1-ylmethyl-phenyl)-3-fluoro-cyclobutyl]-(2,3-dihydro-5H-benzo[f][1,4]oxazepin-4-yl)-methanone;
trans-3-Fluoro-3-(3-fluoro-4-pyrrolidin-1-ylmethyl-phenyl)-cyclobutanecarboxylic acid ethylamide;
trans-3-Fluoro-3-(3-fluoro-4-pyrrolidin-1-ylmethyl-phenyl)-cyclobutanecarboxylic acid ethyl-methyl-amide;

trans-3-(3-Chloro-4-pyrrolidin-1-ylmethyl-phenyl)-3-fluoro-cyclobutanecarboxylic acid methyl-(3-methyl-pyridin-2-ylmethyl)-amide;

trans-3-Fluoro-3-[3-fluoro-4-((R)-2-methyl-pyrrolidin-1-ylmethyl)-phenyl]-cyclobutanecarboxylic acid ethylamide;

trans-3-Fluoro-3-(3-fluoro-4-pyrrolidin-1-ylmethyl-phenyl)-cyclobutanecarboxylic acid isobutyl-amide;

trans-[3-Fluoro-3-(3-fluoro-4-pyrrolidin-1-ylmethyl-phenyl)-cyclobutyl]-pyrrolidin-1-yl-methanone;

trans-[3-Fluoro-3-(3-fluoro-4-pyrrolidin-1-ylmethyl-phenyl)-cyclobutyl]-pyrrolidin-1-yl-methanone; and trans-3-(2,3-Dichloro-4-pyrrolidin-1-ylmethyl-phenyl)-3-fluoro-cyclobutanecarboxylic acid dimethylamide.

16. A pharmaceutical composition comprising a compound of formula I according to claim 1, or a pharmaceutically acceptable salt thereof and a pharmaceutically acceptable carrier.

17. A pharmaceutical composition for treating allergic rhinitis, nasal congestion or allergic congestion comprising:
    (a) an H3 receptor antagonist compound of formula I; or a pharmaceutically acceptable salt thereof, according to claim 1;
    (b) an H1 receptor antagonist or a pharmaceutically acceptable salt thereof; and
    (c) a pharmaceutically acceptable carrier;
wherein the active ingredients (a) and (b) above are present in amounts that render the composition effective in treating allergy rhinitis, nasal congestion or allergic congestion.

18. The pharmaceutical composition according to claim 17, wherein said H1 receptor antagonist is selected from the group consisting of cetirizine chlorpheniramine, loratidine, fexofenadine, and desloradine.

19. A pharmaceutical composition for treating attention-deficit disorder, attention-deficit hyperactivity disorder, or depression comprising:
    (a) an H3 receptor antagonist compound of Formula I or a pharmaceutically acceptable salt thereof, according to claim 1;
    (b) a neurotransmitter re-uptake blocker or a pharmaceutically acceptable salt thereof; and
    (c) a pharmaceutically acceptable carrier;
wherein the active ingredients (a) and (b) above are present in amounts that render the composition effective in treating attention-deficit disorders, attention-deficit hyperactivity disorder, or depression.

20. The pharmaceutical composition according to claim 19, wherein the neurotransmitter re-uptake blocker is selected from the group consisting of sertraline, fluoxetine and paroxetine.

21. A process for the preparation of a compound according to formula I in claim 1, wherein the process comprises the step of reacting a compound of the formula 4,

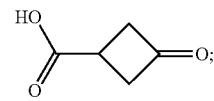

with an organo metallic reagent derived from a compound of formula 2,

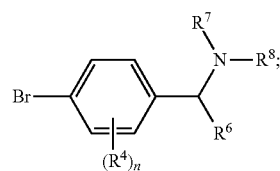

followed by the direct amide formation to yield a compound of the formula I.

22. The compound 3-Fluoro-3-(3-fluoro-4-pyrrolidin-1-ylmethyl-phenyl)cyclobutane carboxylic acid isobutyl amide or a pharmaceutically acceptable salt thereof.

23. The compound trans-3-Fluoro-3-(3-fluoro-4-pyrrolidin-1-ylmethyl-phenyl)cyclobutane carboxylic acid isobutyl amide or a pharmaceutically acceptable salt thereof.

24. The compound cis-3-Fluoro-3-(3-fluoro-4-pyrrolidin-1-ylmethyl-phenyl)cyclobutane carboxylic acid isobutyl amide or a pharmaceutically acceptable salt thereof.

* * * * *